(12) United States Patent
Piehl et al.

(10) Patent No.: US 11,970,786 B2
(45) Date of Patent: Apr. 30, 2024

(54) METHODS AND KITS FOR DETECTING CONTAMINATION AND SAMPLE MISIDENTIFICATION

(71) Applicant: BIOO Scientific Corporation, Austin, TX (US)

(72) Inventors: Shannon Piehl, Austin, TX (US); Josh Kinman, Austin, TX (US)

(73) Assignee: BIOO Scientific Corporation, Austin, TX (US)

( * ) Notice: Subject to any disclaimer, the term of this patent is extended or adjusted under 35 U.S.C. 154(b) by 302 days.

(21) Appl. No.: 16/277,757

(22) Filed: Feb. 15, 2019

(65) Prior Publication Data

US 2019/0249334 A1    Aug. 15, 2019

Related U.S. Application Data

(60) Provisional application No. 62/630,942, filed on Feb. 15, 2018.

(51) Int. Cl.
| | |
|---|---|
| *C40B 40/08* | (2006.01) |
| *C12Q 1/6869* | (2018.01) |
| *C40B 20/04* | (2006.01) |
| *C40B 30/00* | (2006.01) |
| *C12Q 1/686* | (2018.01) |

(52) U.S. Cl.
CPC ............ *C40B 40/08* (2013.01); *C12Q 1/6869* (2013.01); *C40B 20/04* (2013.01); *C40B 30/00* (2013.01); *C12Q 1/686* (2013.01)

(58) Field of Classification Search
CPC .... C12Q 1/686; C12Q 1/6869; C12Q 1/6848; C12Q 2525/191; C12Q 2535/122; C12Q 2563/17; C40B 20/04; C40B 30/00; C40B 40/08

See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis et al. |
| 4,800,159 A | 1/1989 | Mullis et al. |
| 4,965,188 A | 10/1990 | Mullis et al. |
| 5,512,462 A | 4/1996 | Cheng et al. |
| 10,465,232 B1 * | 11/2019 | Wu ................... C12Q 1/6806 |
| 2017/0275691 A1* | 9/2017 | Christians .............. G16B 30/10 |

FOREIGN PATENT DOCUMENTS

| | | | | |
|---|---|---|---|---|
| WO | WO-2017048993 A1 * | 3/2017 | ......... | C12N 15/1093 |
| WO | WO 2017/165864 A1 * | 9/2017 | | |

* cited by examiner

*Primary Examiner* — Sahana S Kaup
(74) *Attorney, Agent, or Firm* — Fish & Richardson P.C.

(57) ABSTRACT

The disclosed methods and kits are useful in processing and analyzing a multiplicity of samples in molecular biology workflows where there is an increased chance for sample cross-contamination or misidentification. Some embodiments of the methods and kits utilize at least one spike in control and at least one barcode per sample.

11 Claims, 6 Drawing Sheets

Specification includes a Sequence Listing.

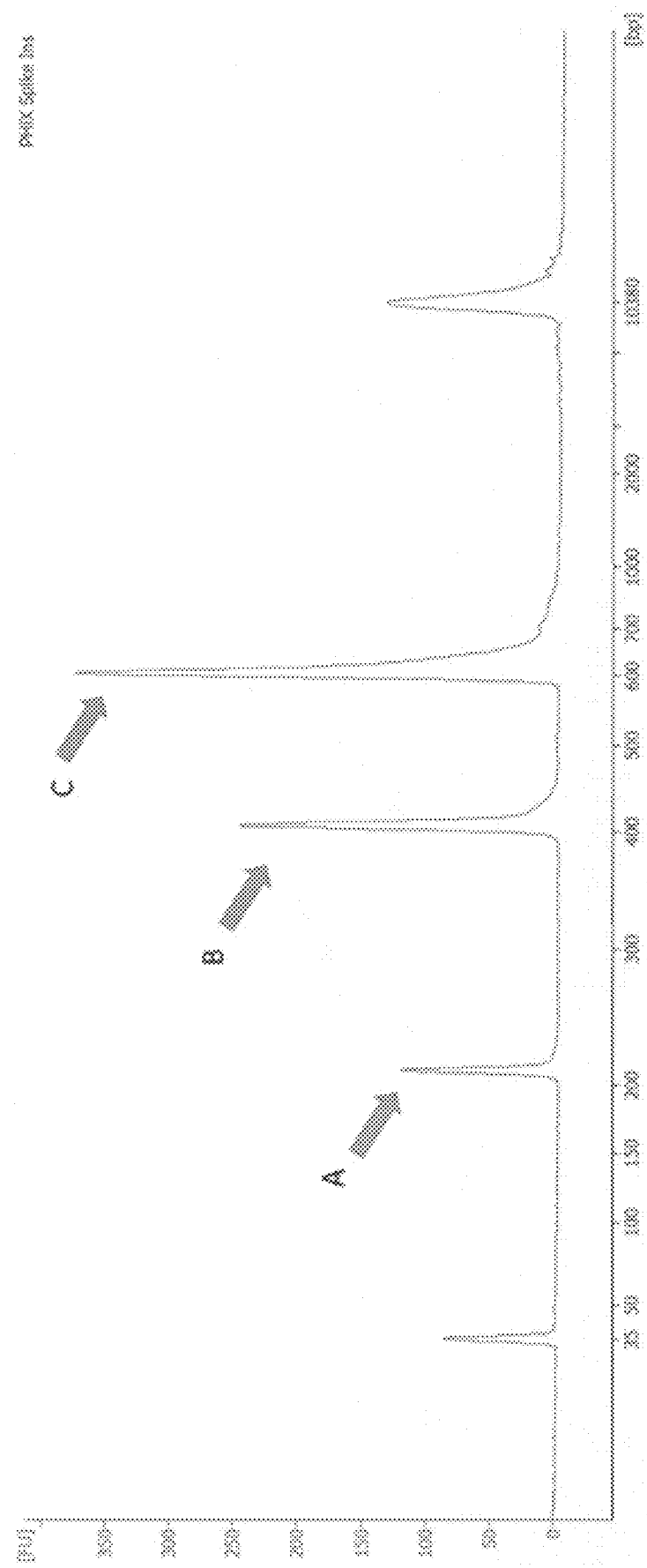
FIG. 2: SPIKED SAMPLE PROFILE PRIOR TO DNA SHEARING

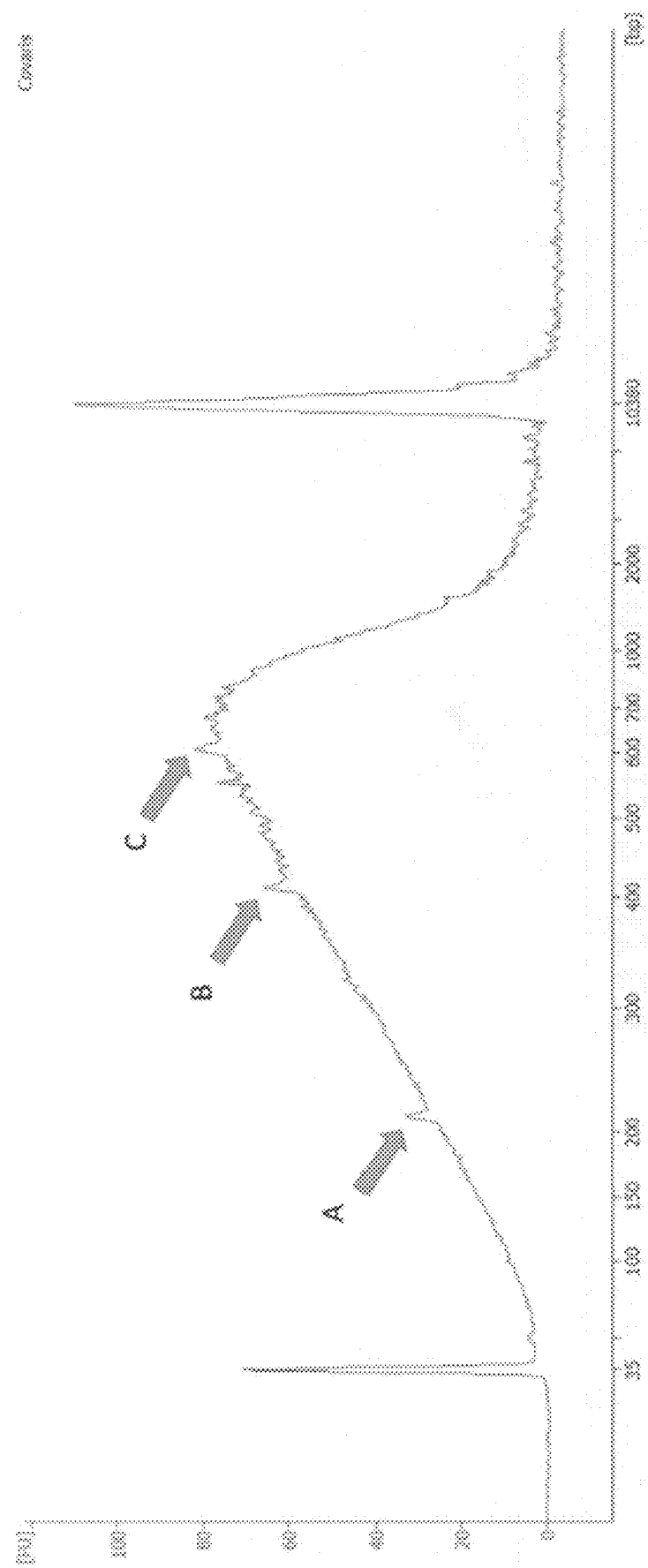
FIG. 3: SPIKED SAMPLE PROFILE FOLLOWING DNA SHEARING

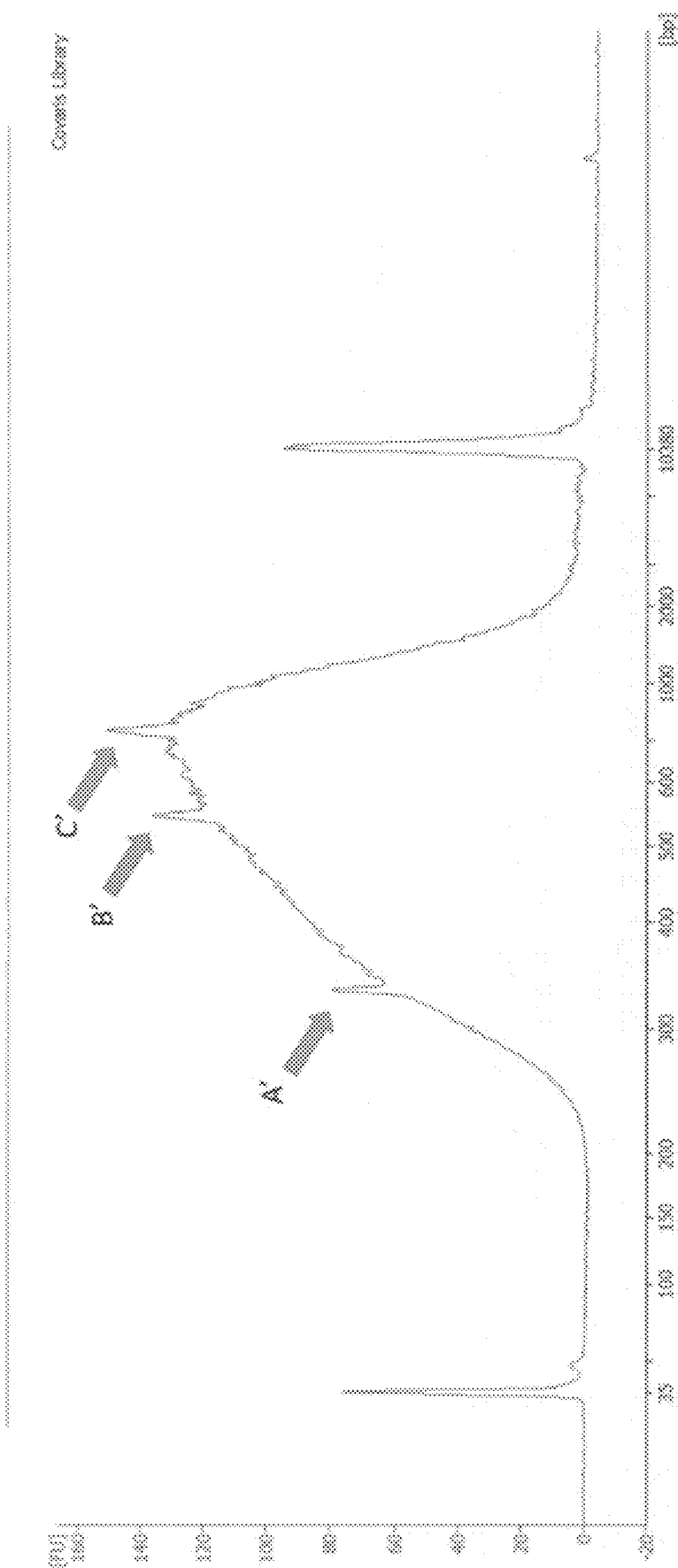

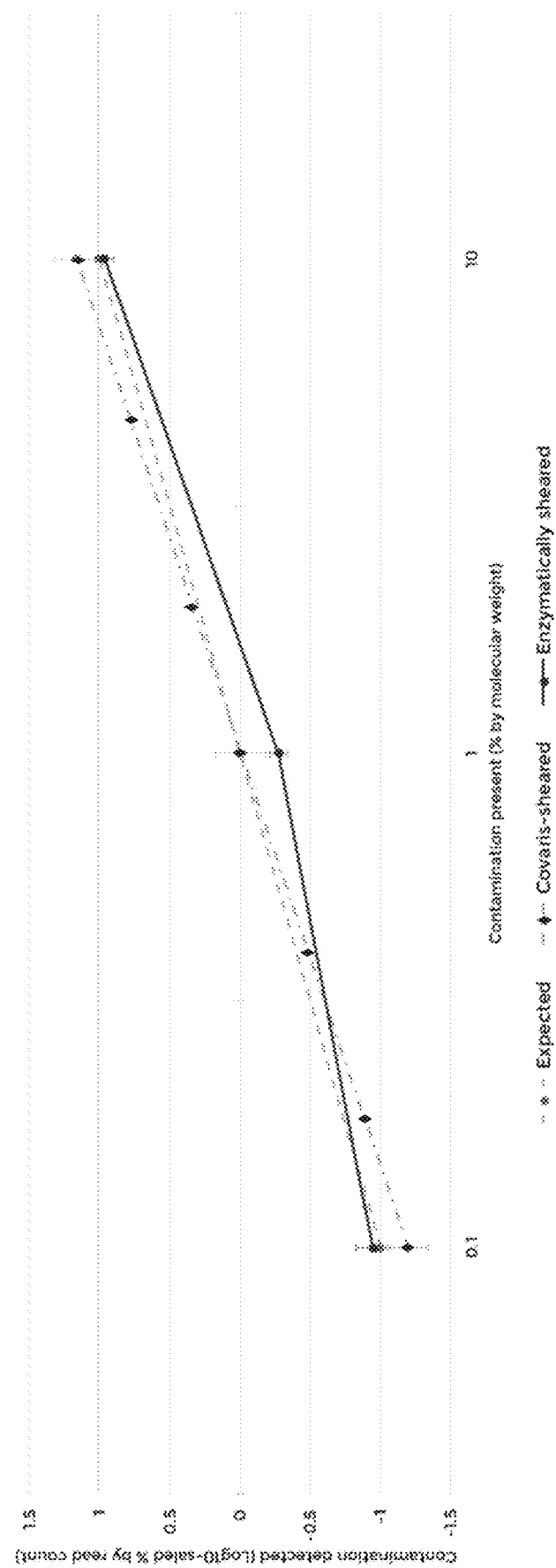
FIG. 5A: Sample-to-sample Cross Contamination in Covaris®-sheared and Enzymatically-sheared Libraries

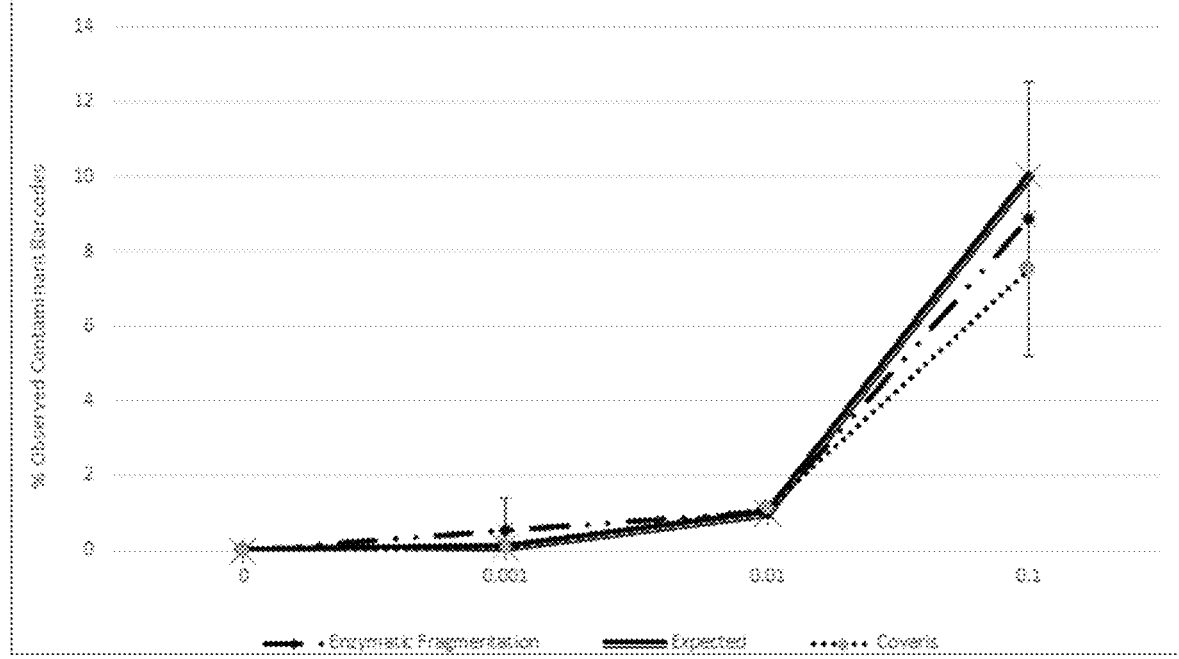

SEQUENCE LISTING

```
<160> NUMBER OF SEQ ID NOS: 384

<210> SEQ ID NO 1
<211> LENGTH: 32
<212> TYPE: DNA
<213> ORGANISM: Artificial
<220> FEATURE:
<223> OTHER INFORMATION: synthetic primer

<400> SEQUENCE: 1
ggcgcgcatc ggggcttgcg tttatggtac gc                                     32

<210> SEQ ID NO 2
<211> LENGTH: 32
<212> TYPE: DNA
<213> ORGANISM: Artificial
<220> FEATURE:
<223> OTHER INFORMATION: synthetic primer

<400> SEQUENCE: 2
cctagctgac aaggcttgcg tttatggtac gc                                     32

<210> SEQ ID NO 3
<211> LENGTH: 32
<212> TYPE: DNA
<213> ORGANISM: Artificial
<220> FEATURE:
<223> OTHER INFORMATION: synthetic primer

<400> SEQUENCE: 3
acaccataga ggggcttgcg tttatggtac gc                                     32

<210> SEQ ID NO 4
<211> LENGTH: 32
<212> TYPE: DNA
<213> ORGANISM: Artificial
<220> FEATURE:
<223> OTHER INFORMATION: synthetic primer

<400> SEQUENCE: 4
ggtcacatgc ggggcttgcg tttatggtac gc                                     32

<210> SEQ ID NO 5
<211> LENGTH: 32
<212> TYPE: DNA
<213> ORGANISM: Artificial
<220> FEATURE:
<223> OTHER INFORMATION: synthetic primer

<400> SEQUENCE: 5
```
ctactcttcc aaggcttgcg tttatggtac gc                     32

<210> SEQ ID NO 6
<211> LENGTH: 32
<212> TYPE: DNA
<213> ORGANISM: Artificial
<220> FEATURE:
<223> OTHER INFORMATION: synthetic primer

<400> SEQUENCE: 6
tgccacacac ttggcttgcg tttatggtac gc                     32

<210> SEQ ID NO 7
<211> LENGTH: 32
<212> TYPE: DNA
<213> ORGANISM: Artificial
<220> FEATURE:
<223> OTHER INFORMATION: synthetic primer

<400> SEQUENCE: 7
tacctagctc ttggcttgcg tttatggtac gc                     32

<210> SEQ ID NO 8
<211> LENGTH: 32
<212> TYPE: DNA
<213> ORGANISM: Artificial
<220> FEATURE:
<223> OTHER INFORMATION: synthetic primer

<400> SEQUENCE: 8
cctaggtgga ggggcttgcg tttatggtac gc                     32

<210> SEQ ID NO 9
<211> LENGTH: 32
<212> TYPE: DNA
<213> ORGANISM: Artificial
<220> FEATURE:
<223> OTHER INFORMATION: synthetic primer

<400> SEQUENCE: 9
gtcctgtgga ccggcttgcg tttatggtac gc                     32

<210> SEQ ID NO 10
<211> LENGTH: 32
<212> TYPE: DNA
<213> ORGANISM: Artificial
<220> FEATURE:
<223> OTHER INFORMATION: synthetic primer

<400> SEQUENCE: 10
tgcgacttcc ggggcttgcg tttatggtac gc                     32

<210> SEQ ID NO 11
<211> LENGTH: 32
<212> TYPE: DNA
<213> ORGANISM: Artificial
<220> FEATURE:
<223> OTHER INFORMATION: synthetic primer

<400> SEQUENCE: 11
gagctccgcg ttggcttgcg tttatggtac gc                     32

<210> SEQ ID NO 12
<211> LENGTH: 32
<212> TYPE: DNA

```
<213> ORGANISM: Artificial
<220> FEATURE:
<223> OTHER INFORMATION: synthetic primer

<400> SEQUENCE: 12
tacaaccaac ggggcttgcg tttatggtac gc                                    32

<210> SEQ ID NO 13
<211> LENGTH: 32
<212> TYPE: DNA
<213> ORGANISM: Artificial
<220> FEATURE:
<223> OTHER INFORMATION: synthetic primer

<400> SEQUENCE: 13
tgagtcgaag aaggcttgcg tttatggtac gc                                    32

<210> SEQ ID NO 14
<211> LENGTH: 32
<212> TYPE: DNA
<213> ORGANISM: Artificial
<220> FEATURE:
<223> OTHER INFORMATION: synthetic primer

<400> SEQUENCE: 14
gacgtgataa ccggcttgcg tttatggtac gc                                    32

<210> SEQ ID NO 15
<211> LENGTH: 32
<212> TYPE: DNA
<213> ORGANISM: Artificial
<220> FEATURE:
<223> OTHER INFORMATION: synthetic primer

<400> SEQUENCE: 15
tggagagagc ttggcttgcg tttatggtac gc                                    32

<210> SEQ ID NO 16
<211> LENGTH: 32
<212> TYPE: DNA
<213> ORGANISM: Artificial
<220> FEATURE:
<223> OTHER INFORMATION: synthetic primer

<400> SEQUENCE: 16
gatcgccaca ccggcttgcg tttatggtac gc                                    32

<210> SEQ ID NO 17
<211> LENGTH: 32
<212> TYPE: DNA
<213> ORGANISM: Artificial
<220> FEATURE:
<223> OTHER INFORMATION: synthetic primer

<400> SEQUENCE: 17
gttcagagca ggggcttgcg tttatggtac gc                                    32

<210> SEQ ID NO 18
<211> LENGTH: 32
<212> TYPE: DNA
<213> ORGANISM: Artificial
<220> FEATURE:
<223> OTHER INFORMATION: synthetic primer

<400> SEQUENCE: 18
caatgaggca ccggcttgcg tttatggtac gc                                    32
```

<210> SEQ ID NO 19
<211> LENGTH: 32
<212> TYPE: DNA
<213> ORGANISM: Artificial
<220> FEATURE:
<223> OTHER INFORMATION: synthetic primer

<400> SEQUENCE: 19
atggatgcca ccggcttgcg tttatggtac gc                                    32

<210> SEQ ID NO 20
<211> LENGTH: 32
<212> TYPE: DNA
<213> ORGANISM: Artificial
<220> FEATURE:
<223> OTHER INFORMATION: synthetic primer

<400> SEQUENCE: 20
tatacgtcac ttggcttgcg tttatggtac gc                                    32

<210> SEQ ID NO 21
<211> LENGTH: 32
<212> TYPE: DNA
<213> ORGANISM: Artificial
<220> FEATURE:
<223> OTHER INFORMATION: synthetic primer

<400> SEQUENCE: 21
cataacggaa ggggcttgcg tttatggtac gc                                    32

<210> SEQ ID NO 22
<211> LENGTH: 32
<212> TYPE: DNA
<213> ORGANISM: Artificial
<220> FEATURE:
<223> OTHER INFORMATION: synthetic primer

<400> SEQUENCE: 22
acttcgtgga ccggcttgcg tttatggtac gc                                    32

<210> SEQ ID NO 23
<211> LENGTH: 32
<212> TYPE: DNA
<213> ORGANISM: Artificial
<220> FEATURE:
<223> OTHER INFORMATION: synthetic primer

<400> SEQUENCE: 23
tgctggtcac ggggcttgcg tttatggtac gc                                    32

<210> SEQ ID NO 24
<211> LENGTH: 32
<212> TYPE: DNA
<213> ORGANISM: Artificial
<220> FEATURE:
<223> OTHER INFORMATION: synthetic primer

<400> SEQUENCE: 24
acgtcgatcc ttggcttgcg tttatggtac gc                                    32

<210> SEQ ID NO 25
<211> LENGTH: 32
<212> TYPE: DNA
<213> ORGANISM: Artificial
<220> FEATURE:

<223> OTHER INFORMATION: synthetic primer

<400> SEQUENCE: 25
gcaggtaaga ggggcttgcg tttatggtac gc                           32

<210> SEQ ID NO 26
<211> LENGTH: 32
<212> TYPE: DNA
<213> ORGANISM: Artificial
<220> FEATURE:
<223> OTHER INFORMATION: synthetic primer

<400> SEQUENCE: 26
gctctaggac aaggcttgcg tttatggtac gc                           32

<210> SEQ ID NO 27
<211> LENGTH: 32
<212> TYPE: DNA
<213> ORGANISM: Artificial
<220> FEATURE:
<223> OTHER INFORMATION: synthetic primer

<400> SEQUENCE: 27
agcgcatatc aaggcttgcg tttatggtac gc                           32

<210> SEQ ID NO 28
<211> LENGTH: 32
<212> TYPE: DNA
<213> ORGANISM: Artificial
<220> FEATURE:
<223> OTHER INFORMATION: synthetic primer

<400> SEQUENCE: 28
acaccttaac aaggcttgcg tttatggtac gc                           32

<210> SEQ ID NO 29
<211> LENGTH: 32
<212> TYPE: DNA
<213> ORGANISM: Artificial
<220> FEATURE:
<223> OTHER INFORMATION: synthetic primer

<400> SEQUENCE: 29
gattcactta ccggcttgcg tttatggtac gc                           32

<210> SEQ ID NO 30
<211> LENGTH: 32
<212> TYPE: DNA
<213> ORGANISM: Artificial
<220> FEATURE:
<223> OTHER INFORMATION: synthetic primer

<400> SEQUENCE: 30
ggtccataga ccggcttgcg tttatggtac gc                           32

<210> SEQ ID NO 31
<211> LENGTH: 32
<212> TYPE: DNA
<213> ORGANISM: Artificial
<220> FEATURE:
<223> OTHER INFORMATION: synthetic primer

<400> SEQUENCE: 31
tctaagatgg ccggcttgcg tttatggtac gc                           32

-continued

```
<210> SEQ ID NO 32
<211> LENGTH: 32
<212> TYPE: DNA
<213> ORGANISM: Artificial
<220> FEATURE:
<223> OTHER INFORMATION: synthetic primer

<400> SEQUENCE: 32
aatgccgatc ttggcttgcg tttatggtac gc                                32

<210> SEQ ID NO 33
<211> LENGTH: 32
<212> TYPE: DNA
<213> ORGANISM: Artificial
<220> FEATURE:
<223> OTHER INFORMATION: synthetic primer

<400> SEQUENCE: 33
ccaggataga ccggcttgcg tttatggtac gc                                32

<210> SEQ ID NO 34
<211> LENGTH: 32
<212> TYPE: DNA
<213> ORGANISM: Artificial
<220> FEATURE:
<223> OTHER INFORMATION: synthetic primer

<400> SEQUENCE: 34
gttatgttcg aaggcttgcg tttatggtac gc                                32

<210> SEQ ID NO 35
<211> LENGTH: 32
<212> TYPE: DNA
<213> ORGANISM: Artificial
<220> FEATURE:
<223> OTHER INFORMATION: synthetic primer

<400> SEQUENCE: 35
ggctagtagg aaggcttgcg tttatggtac gc                                32

<210> SEQ ID NO 36
<211> LENGTH: 32
<212> TYPE: DNA
<213> ORGANISM: Artificial
<220> FEATURE:
<223> OTHER INFORMATION: synthetic primer

<400> SEQUENCE: 36
gtacgatatc ggggcttgcg tttatggtac gc                                32

<210> SEQ ID NO 37
<211> LENGTH: 32
<212> TYPE: DNA
<213> ORGANISM: Artificial
<220> FEATURE:
<223> OTHER INFORMATION: synthetic primer

<400> SEQUENCE: 37
aaccacttaa ccggcttgcg tttatggtac gc                                32

<210> SEQ ID NO 38
<211> LENGTH: 32
<212> TYPE: DNA
<213> ORGANISM: Artificial
<220> FEATURE:
<223> OTHER INFORMATION: synthetic primer
```

<400> SEQUENCE: 38
tccgctatac ggggcttgcg tttatggtac gc        32

<210> SEQ ID NO 39
<211> LENGTH: 32
<212> TYPE: DNA
<213> ORGANISM: Artificial
<220> FEATURE:
<223> OTHER INFORMATION: synthetic primer

<400> SEQUENCE: 39
actctgagac ggggcttgcg tttatggtac gc        32

<210> SEQ ID NO 40
<211> LENGTH: 32
<212> TYPE: DNA
<213> ORGANISM: Artificial
<220> FEATURE:
<223> OTHER INFORMATION: synthetic primer

<400> SEQUENCE: 40
gcgtcggtag aaggcttgcg tttatggtac gc        32

<210> SEQ ID NO 41
<211> LENGTH: 32
<212> TYPE: DNA
<213> ORGANISM: Artificial
<220> FEATURE:
<223> OTHER INFORMATION: synthetic primer

<400> SEQUENCE: 41
atatggtcac ttggcttgcg tttatggtac gc        32

<210> SEQ ID NO 42
<211> LENGTH: 32
<212> TYPE: DNA
<213> ORGANISM: Artificial
<220> FEATURE:
<223> OTHER INFORMATION: synthetic primer

<400> SEQUENCE: 42
ttaattaatc aaggcttgcg tttatggtac gc        32

<210> SEQ ID NO 43
<211> LENGTH: 32
<212> TYPE: DNA
<213> ORGANISM: Artificial
<220> FEATURE:
<223> OTHER INFORMATION: synthetic primer

<400> SEQUENCE: 43
aagttgctca ccggcttgcg tttatggtac gc        32

<210> SEQ ID NO 44
<211> LENGTH: 32
<212> TYPE: DNA
<213> ORGANISM: Artificial
<220> FEATURE:
<223> OTHER INFORMATION: synthetic primer

<400> SEQUENCE: 44
ggttatggag aaggcttgcg tttatggtac gc        32

<210> SEQ ID NO 45
<211> LENGTH: 32

```
<212> TYPE: DNA
<213> ORGANISM: Artificial
<220> FEATURE:
<223> OTHER INFORMATION: synthetic primer

<400> SEQUENCE: 45
tagacgaata ccggcttgcg tttatggtac gc                                   32

<210> SEQ ID NO 46
<211> LENGTH: 32
<212> TYPE: DNA
<213> ORGANISM: Artificial
<220> FEATURE:
<223> OTHER INFORMATION: synthetic primer

<400> SEQUENCE: 46
tctacataag aaggcttgcg tttatggtac gc                                   32

<210> SEQ ID NO 47
<211> LENGTH: 32
<212> TYPE: DNA
<213> ORGANISM: Artificial
<220> FEATURE:
<223> OTHER INFORMATION: synthetic primer

<400> SEQUENCE: 47
cagaaccttc aaggcttgcg tttatggtac gc                                   32

<210> SEQ ID NO 48
<211> LENGTH: 32
<212> TYPE: DNA
<213> ORGANISM: Artificial
<220> FEATURE:
<223> OTHER INFORMATION: synthetic primer

<400> SEQUENCE: 48
caaggctcag aaggcttgcg tttatggtac gc                                   32

<210> SEQ ID NO 49
<211> LENGTH: 32
<212> TYPE: DNA
<213> ORGANISM: Artificial
<220> FEATURE:
<223> OTHER INFORMATION: synthetic primer

<400> SEQUENCE: 49
gactccacca ccggcttgcg tttatggtac gc                                   32

<210> SEQ ID NO 50
<211> LENGTH: 32
<212> TYPE: DNA
<213> ORGANISM: Artificial
<220> FEATURE:
<223> OTHER INFORMATION: synthetic primer

<400> SEQUENCE: 50
aaccgtggag aaggcttgcg tttatggtac gc                                   32

<210> SEQ ID NO 51
<211> LENGTH: 32
<212> TYPE: DNA
<213> ORGANISM: Artificial
<220> FEATURE:
<223> OTHER INFORMATION: synthetic primer

<400> SEQUENCE: 51
```
ggtccttaac ttggcttgcg tttatggtac gc        32

<210> SEQ ID NO 52
<211> LENGTH: 32
<212> TYPE: DNA
<213> ORGANISM: Artificial
<220> FEATURE:
<223> OTHER INFORMATION: synthetic primer

<400> SEQUENCE: 52
cgccacgccg aaggcttgcg tttatggtac gc        32

<210> SEQ ID NO 53
<211> LENGTH: 32
<212> TYPE: DNA
<213> ORGANISM: Artificial
<220> FEATURE:
<223> OTHER INFORMATION: synthetic primer

<400> SEQUENCE: 53
acttatacgc ggggcttgcg tttatggtac gc        32

<210> SEQ ID NO 54
<211> LENGTH: 32
<212> TYPE: DNA
<213> ORGANISM: Artificial
<220> FEATURE:
<223> OTHER INFORMATION: synthetic primer

<400> SEQUENCE: 54
ctcctcagga ggggcttgcg tttatggtac gc        32

<210> SEQ ID NO 55
<211> LENGTH: 32
<212> TYPE: DNA
<213> ORGANISM: Artificial
<220> FEATURE:
<223> OTHER INFORMATION: synthetic primer

<400> SEQUENCE: 55
gtgaggtcca ggggcttgcg tttatggtac gc        32

<210> SEQ ID NO 56
<211> LENGTH: 32
<212> TYPE: DNA
<213> ORGANISM: Artificial
<220> FEATURE:
<223> OTHER INFORMATION: synthetic primer

<400> SEQUENCE: 56
cacatgcgcc ttggcttgcg tttatggtac gc        32

<210> SEQ ID NO 57
<211> LENGTH: 32
<212> TYPE: DNA
<213> ORGANISM: Artificial
<220> FEATURE:
<223> OTHER INFORMATION: synthetic primer

<400> SEQUENCE: 57
gtgcacttaa ggggcttgcg tttatggtac gc        32

<210> SEQ ID NO 58
<211> LENGTH: 32
<212> TYPE: DNA
<213> ORGANISM: Artificial

```
<220> FEATURE:
<223> OTHER INFORMATION: synthetic primer

<400> SEQUENCE: 58
ggcgtgacga ggggcttgcg tttatggtac gc                              32

<210> SEQ ID NO 59
<211> LENGTH: 32
<212> TYPE: DNA
<213> ORGANISM: Artificial
<220> FEATURE:
<223> OTHER INFORMATION: synthetic primer

<400> SEQUENCE: 59
aatagtgtta ccggcttgcg tttatggtac gc                              32

<210> SEQ ID NO 60
<211> LENGTH: 32
<212> TYPE: DNA
<213> ORGANISM: Artificial
<220> FEATURE:
<223> OTHER INFORMATION: synthetic primer

<400> SEQUENCE: 60
cagaagctca ggggcttgcg tttatggtac gc                              32

<210> SEQ ID NO 61
<211> LENGTH: 32
<212> TYPE: DNA
<213> ORGANISM: Artificial
<220> FEATURE:
<223> OTHER INFORMATION: synthetic primer

<400> SEQUENCE: 61
tagtggcaag aaggcttgcg tttatggtac gc                              32

<210> SEQ ID NO 62
<211> LENGTH: 32
<212> TYPE: DNA
<213> ORGANISM: Artificial
<220> FEATURE:
<223> OTHER INFORMATION: synthetic primer

<400> SEQUENCE: 62
acagactctc aaggcttgcg tttatggtac gc                              32

<210> SEQ ID NO 63
<211> LENGTH: 32
<212> TYPE: DNA
<213> ORGANISM: Artificial
<220> FEATURE:
<223> OTHER INFORMATION: synthetic primer

<400> SEQUENCE: 63
ggatgacacc ttggcttgcg tttatggtac gc                              32

<210> SEQ ID NO 64
<211> LENGTH: 32
<212> TYPE: DNA
<213> ORGANISM: Artificial
<220> FEATURE:
<223> OTHER INFORMATION: synthetic primer

<400> SEQUENCE: 64
gtgagctctc aaggcttgcg tttatggtac gc                              32
```

<210> SEQ ID NO 65
<211> LENGTH: 32
<212> TYPE: DNA
<213> ORGANISM: Artificial
<220> FEATURE:
<223> OTHER INFORMATION: synthetic primer

<400> SEQUENCE: 65
actccgctca ggggcttgcg tttatggtac gc                                      32

<210> SEQ ID NO 66
<211> LENGTH: 32
<212> TYPE: DNA
<213> ORGANISM: Artificial
<220> FEATURE:
<223> OTHER INFORMATION: synthetic primer

<400> SEQUENCE: 66
atcgttgacc aaggcttgcg tttatggtac gc                                      32

<210> SEQ ID NO 67
<211> LENGTH: 32
<212> TYPE: DNA
<213> ORGANISM: Artificial
<220> FEATURE:
<223> OTHER INFORMATION: synthetic primer

<400> SEQUENCE: 67
cagtgctata ccggcttgcg tttatggtac gc                                      32

<210> SEQ ID NO 68
<211> LENGTH: 32
<212> TYPE: DNA
<213> ORGANISM: Artificial
<220> FEATURE:
<223> OTHER INFORMATION: synthetic primer

<400> SEQUENCE: 68
cagtcacgga ggggcttgcg tttatggtac gc                                      32

<210> SEQ ID NO 69
<211> LENGTH: 32
<212> TYPE: DNA
<213> ORGANISM: Artificial
<220> FEATURE:
<223> OTHER INFORMATION: synthetic primer

<400> SEQUENCE: 69
atacggcatc aaggcttgcg tttatggtac gc                                      32

<210> SEQ ID NO 70
<211> LENGTH: 32
<212> TYPE: DNA
<213> ORGANISM: Artificial
<220> FEATURE:
<223> OTHER INFORMATION: synthetic primer

<400> SEQUENCE: 70
tgtaagaacg aaggcttgcg tttatggtac gc                                      32

<210> SEQ ID NO 71
<211> LENGTH: 32
<212> TYPE: DNA
<213> ORGANISM: Artificial
<220> FEATURE:
<223> OTHER INFORMATION: synthetic primer

```
<400> SEQUENCE: 71
agctagcatc ttggcttgcg tttatggtac gc                                    32

<210> SEQ ID NO 72
<211> LENGTH: 32
<212> TYPE: DNA
<213> ORGANISM: Artificial
<220> FEATURE:
<223> OTHER INFORMATION: synthetic primer

<400> SEQUENCE: 72
ccaagtcctc aaggcttgcg tttatggtac gc                                    32

<210> SEQ ID NO 73
<211> LENGTH: 32
<212> TYPE: DNA
<213> ORGANISM: Artificial
<220> FEATURE:
<223> OTHER INFORMATION: synthetic primer

<400> SEQUENCE: 73
caagtcagtc aaggcttgcg tttatggtac gc                                    32

<210> SEQ ID NO 74
<211> LENGTH: 32
<212> TYPE: DNA
<213> ORGANISM: Artificial
<220> FEATURE:
<223> OTHER INFORMATION: synthetic primer

<400> SEQUENCE: 74
tgcggcggaa ggggcttgcg tttatggtac gc                                    32

<210> SEQ ID NO 75
<211> LENGTH: 32
<212> TYPE: DNA
<213> ORGANISM: Artificial
<220> FEATURE:
<223> OTHER INFORMATION: synthetic primer

<400> SEQUENCE: 75
ctcgcggcaa ccggcttgcg tttatggtac gc                                    32

<210> SEQ ID NO 76
<211> LENGTH: 32
<212> TYPE: DNA
<213> ORGANISM: Artificial
<220> FEATURE:
<223> OTHER INFORMATION: synthetic primer

<400> SEQUENCE: 76
tcacctaaga ccggcttgcg tttatggtac gc                                    32

<210> SEQ ID NO 77
<211> LENGTH: 32
<212> TYPE: DNA
<213> ORGANISM: Artificial
<220> FEATURE:
<223> OTHER INFORMATION: synthetic primer

<400> SEQUENCE: 77
ccgctagtcc ttggcttgcg tttatggtac gc                                    32

<210> SEQ ID NO 78
```

```
<211> LENGTH: 32
<212> TYPE: DNA
<213> ORGANISM: Artificial
<220> FEATURE:
<223> OTHER INFORMATION: synthetic primer

<400> SEQUENCE: 78
agcggccggc ttggcttgcg tttatggtac gc                                   32

<210> SEQ ID NO 79
<211> LENGTH: 32
<212> TYPE: DNA
<213> ORGANISM: Artificial
<220> FEATURE:
<223> OTHER INFORMATION: synthetic primer

<400> SEQUENCE: 79
tccgttcgca ggggcttgcg tttatggtac gc                                   32

<210> SEQ ID NO 80
<211> LENGTH: 32
<212> TYPE: DNA
<213> ORGANISM: Artificial
<220> FEATURE:
<223> OTHER INFORMATION: synthetic primer

<400> SEQUENCE: 80
ccgacagcga ccggcttgcg tttatggtac gc                                   32

<210> SEQ ID NO 81
<211> LENGTH: 32
<212> TYPE: DNA
<213> ORGANISM: Artificial
<220> FEATURE:
<223> OTHER INFORMATION: synthetic primer

<400> SEQUENCE: 81
ccaacgttgc ttggcttgcg tttatggtac gc                                   32

<210> SEQ ID NO 82
<211> LENGTH: 32
<212> TYPE: DNA
<213> ORGANISM: Artificial
<220> FEATURE:
<223> OTHER INFORMATION: synthetic primer

<400> SEQUENCE: 82
ctgaatcacg aaggcttgcg tttatggtac gc                                   32

<210> SEQ ID NO 83
<211> LENGTH: 32
<212> TYPE: DNA
<213> ORGANISM: Artificial
<220> FEATURE:
<223> OTHER INFORMATION: synthetic primer

<400> SEQUENCE: 83
aggacgtgtc ttggcttgcg tttatggtac gc                                   32

<210> SEQ ID NO 84
<211> LENGTH: 32
<212> TYPE: DNA
<213> ORGANISM: Artificial
<220> FEATURE:
<223> OTHER INFORMATION: synthetic primer

<400> SEQUENCE: 84
```
taatagctac ttggcttgcg tttatggtac gc　　　　　　　　　　　　　　32

<210> SEQ ID NO 85
<211> LENGTH: 32
<212> TYPE: DNA
<213> ORGANISM: Artificial
<220> FEATURE:
<223> OTHER INFORMATION: synthetic primer

<400> SEQUENCE: 85
gtaggaaggc ttggcttgcg tttatggtac gc　　　　　　　　　　　　　　32

<210> SEQ ID NO 86
<211> LENGTH: 32
<212> TYPE: DNA
<213> ORGANISM: Artificial
<220> FEATURE:
<223> OTHER INFORMATION: synthetic primer

<400> SEQUENCE: 86
gtaatacagg aaggcttgcg tttatggtac gc　　　　　　　　　　　　　　32

<210> SEQ ID NO 87
<211> LENGTH: 32
<212> TYPE: DNA
<213> ORGANISM: Artificial
<220> FEATURE:
<223> OTHER INFORMATION: synthetic primer

<400> SEQUENCE: 87
gccgcgctac ttggcttgcg tttatggtac gc　　　　　　　　　　　　　　32

<210> SEQ ID NO 88
<211> LENGTH: 32
<212> TYPE: DNA
<213> ORGANISM: Artificial
<220> FEATURE:
<223> OTHER INFORMATION: synthetic primer

<400> SEQUENCE: 88
cgactctgac ggggcttgcg tttatggtac gc　　　　　　　　　　　　　　32

<210> SEQ ID NO 89
<211> LENGTH: 32
<212> TYPE: DNA
<213> ORGANISM: Artificial
<220> FEATURE:
<223> OTHER INFORMATION: synthetic primer

<400> SEQUENCE: 89
ctcatgccgc ggggcttgcg tttatggtac gc　　　　　　　　　　　　　　32

<210> SEQ ID NO 90
<211> LENGTH: 32
<212> TYPE: DNA
<213> ORGANISM: Artificial
<220> FEATURE:
<223> OTHER INFORMATION: synthetic primer

<400> SEQUENCE: 90
tcctggtgtc ttggcttgcg tttatggtac gc　　　　　　　　　　　　　　32

<210> SEQ ID NO 91
<211> LENGTH: 32
<212> TYPE: DNA

<213> ORGANISM: Artificial
<220> FEATURE:
<223> OTHER INFORMATION: synthetic primer

<400> SEQUENCE: 91
cagcggccgc aaggcttgcg tttatggtac gc                              32

<210> SEQ ID NO 92
<211> LENGTH: 32
<212> TYPE: DNA
<213> ORGANISM: Artificial
<220> FEATURE:
<223> OTHER INFORMATION: synthetic primer

<400> SEQUENCE: 92
taacgcgtac ggggcttgcg tttatggtac gc                              32

<210> SEQ ID NO 93
<211> LENGTH: 32
<212> TYPE: DNA
<213> ORGANISM: Artificial
<220> FEATURE:
<223> OTHER INFORMATION: synthetic primer

<400> SEQUENCE: 93
ctaggatgaa ggggcttgcg tttatggtac gc                              32

<210> SEQ ID NO 94
<211> LENGTH: 32
<212> TYPE: DNA
<213> ORGANISM: Artificial
<220> FEATURE:
<223> OTHER INFORMATION: synthetic primer

<400> SEQUENCE: 94
gcattcgaga ccggcttgcg tttatggtac gc                              32

<210> SEQ ID NO 95
<211> LENGTH: 32
<212> TYPE: DNA
<213> ORGANISM: Artificial
<220> FEATURE:
<223> OTHER INFORMATION: synthetic primer

<400> SEQUENCE: 95
tatcgtaatc ggggcttgcg tttatggtac gc                              32

<210> SEQ ID NO 96
<211> LENGTH: 32
<212> TYPE: DNA
<213> ORGANISM: Artificial
<220> FEATURE:
<223> OTHER INFORMATION: synthetic primer

<400> SEQUENCE: 96
agtcatgtgc aaggcttgcg tttatggtac gc                              32

<210> SEQ ID NO 97
<211> LENGTH: 30
<212> TYPE: DNA
<213> ORGANISM: Artificial
<220> FEATURE:
<223> OTHER INFORMATION: synthetic primer

<400> SEQUENCE: 97
ggcgcgcatc gggctttaac cggacgctcg                                 30

<210> SEQ ID NO 98
<211> LENGTH: 30
<212> TYPE: DNA
<213> ORGANISM: Artificial
<220> FEATURE:
<223> OTHER INFORMATION: synthetic primer

<400> SEQUENCE: 98
cctagctgac aagctttaac cggacgctcg        30

<210> SEQ ID NO 99
<211> LENGTH: 30
<212> TYPE: DNA
<213> ORGANISM: Artificial
<220> FEATURE:
<223> OTHER INFORMATION: synthetic primer

<400> SEQUENCE: 99
acaccataga gggctttaac cggacgctcg        30

<210> SEQ ID NO 100
<211> LENGTH: 30
<212> TYPE: DNA
<213> ORGANISM: Artificial
<220> FEATURE:
<223> OTHER INFORMATION: synthetic primer

<400> SEQUENCE: 100
ggtcacatgc gggctttaac cggacgctcg        30

<210> SEQ ID NO 101
<211> LENGTH: 30
<212> TYPE: DNA
<213> ORGANISM: Artificial
<220> FEATURE:
<223> OTHER INFORMATION: synthetic primer

<400> SEQUENCE: 101
ctactcttcc aagctttaac cggacgctcg        30

<210> SEQ ID NO 102
<211> LENGTH: 30
<212> TYPE: DNA
<213> ORGANISM: Artificial
<220> FEATURE:
<223> OTHER INFORMATION: synthetic primer

<400> SEQUENCE: 102
tgccacacac ttgctttaac cggacgctcg        30

<210> SEQ ID NO 103
<211> LENGTH: 30
<212> TYPE: DNA
<213> ORGANISM: Artificial
<220> FEATURE:
<223> OTHER INFORMATION: synthetic primer

<400> SEQUENCE: 103
tacctagctc ttgctttaac cggacgctcg        30

<210> SEQ ID NO 104
<211> LENGTH: 30
<212> TYPE: DNA
<213> ORGANISM: Artificial
<220> FEATURE:

<223> OTHER INFORMATION: synthetic primer

<400> SEQUENCE: 104
cctaggtgga gggctttaac cggacgctcg                              30

<210> SEQ ID NO 105
<211> LENGTH: 30
<212> TYPE: DNA
<213> ORGANISM: Artificial
<220> FEATURE:
<223> OTHER INFORMATION: synthetic primer

<400> SEQUENCE: 105
gtcctgtgga ccgctttaac cggacgctcg                              30

<210> SEQ ID NO 106
<211> LENGTH: 30
<212> TYPE: DNA
<213> ORGANISM: Artificial
<220> FEATURE:
<223> OTHER INFORMATION: synthetic primer

<400> SEQUENCE: 106
tgcgacttcc gggctttaac cggacgctcg                              30

<210> SEQ ID NO 107
<211> LENGTH: 30
<212> TYPE: DNA
<213> ORGANISM: Artificial
<220> FEATURE:
<223> OTHER INFORMATION: synthetic primer

<400> SEQUENCE: 107
gagctccgcg ttgctttaac cggacgctcg                              30

<210> SEQ ID NO 108
<211> LENGTH: 30
<212> TYPE: DNA
<213> ORGANISM: Artificial
<220> FEATURE:
<223> OTHER INFORMATION: synthetic primer

<400> SEQUENCE: 108
tacaaccaac gggctttaac cggacgctcg                              30

<210> SEQ ID NO 109
<211> LENGTH: 30
<212> TYPE: DNA
<213> ORGANISM: Artificial
<220> FEATURE:
<223> OTHER INFORMATION: synthetic primer

<400> SEQUENCE: 109
tgagtcgaag aagctttaac cggacgctcg                              30

<210> SEQ ID NO 110
<211> LENGTH: 30
<212> TYPE: DNA
<213> ORGANISM: Artificial
<220> FEATURE:
<223> OTHER INFORMATION: synthetic primer

<400> SEQUENCE: 110
gacgtgataa ccgctttaac cggacgctcg                              30

<210> SEQ ID NO 111
<211> LENGTH: 30
<212> TYPE: DNA
<213> ORGANISM: Artificial
<220> FEATURE:
<223> OTHER INFORMATION: synthetic primer

<400> SEQUENCE: 111
tggagagagc ttgctttaac cggacgctcg                                    30

<210> SEQ ID NO 112
<211> LENGTH: 30
<212> TYPE: DNA
<213> ORGANISM: Artificial
<220> FEATURE:
<223> OTHER INFORMATION: synthetic primer

<400> SEQUENCE: 112
gatcgccaca ccgctttaac cggacgctcg                                    30

<210> SEQ ID NO 113
<211> LENGTH: 30
<212> TYPE: DNA
<213> ORGANISM: Artificial
<220> FEATURE:
<223> OTHER INFORMATION: synthetic primer

<400> SEQUENCE: 113
gttcagagca gggctttaac cggacgctcg                                    30

<210> SEQ ID NO 114
<211> LENGTH: 30
<212> TYPE: DNA
<213> ORGANISM: Artificial
<220> FEATURE:
<223> OTHER INFORMATION: synthetic primer

<400> SEQUENCE: 114
caatgaggca ccgctttaac cggacgctcg                                    30

<210> SEQ ID NO 115
<211> LENGTH: 30
<212> TYPE: DNA
<213> ORGANISM: Artificial
<220> FEATURE:
<223> OTHER INFORMATION: synthetic primer

<400> SEQUENCE: 115
atggatgcca ccgctttaac cggacgctcg                                    30

<210> SEQ ID NO 116
<211> LENGTH: 30
<212> TYPE: DNA
<213> ORGANISM: Artificial
<220> FEATURE:
<223> OTHER INFORMATION: synthetic primer

<400> SEQUENCE: 116
tatacgtcac ttgctttaac cggacgctcg                                    30

<210> SEQ ID NO 117
<211> LENGTH: 30
<212> TYPE: DNA
<213> ORGANISM: Artificial
<220> FEATURE:
<223> OTHER INFORMATION: synthetic primer

<400> SEQUENCE: 117
cataacggaa gggctttaac cggacgctcg                                          30

<210> SEQ ID NO 118
<211> LENGTH: 30
<212> TYPE: DNA
<213> ORGANISM: Artificial
<220> FEATURE:
<223> OTHER INFORMATION: synthetic primer

<400> SEQUENCE: 118
acttcgtgga ccgctttaac cggacgctcg                                          30

<210> SEQ ID NO 119
<211> LENGTH: 30
<212> TYPE: DNA
<213> ORGANISM: Artificial
<220> FEATURE:
<223> OTHER INFORMATION: synthetic primer

<400> SEQUENCE: 119
tgctggtcac gggctttaac cggacgctcg                                          30

<210> SEQ ID NO 120
<211> LENGTH: 30
<212> TYPE: DNA
<213> ORGANISM: Artificial
<220> FEATURE:
<223> OTHER INFORMATION: synthetic primer

<400> SEQUENCE: 120
acgtcgatcc ttgctttaac cggacgctcg                                          30

<210> SEQ ID NO 121
<211> LENGTH: 30
<212> TYPE: DNA
<213> ORGANISM: Artificial
<220> FEATURE:
<223> OTHER INFORMATION: synthetic primer

<400> SEQUENCE: 121
gcaggtaaga gggctttaac cggacgctcg                                          30

<210> SEQ ID NO 122
<211> LENGTH: 30
<212> TYPE: DNA
<213> ORGANISM: Artificial
<220> FEATURE:
<223> OTHER INFORMATION: synthetic primer

<400> SEQUENCE: 122
gctctaggac aagctttaac cggacgctcg                                          30

<210> SEQ ID NO 123
<211> LENGTH: 30
<212> TYPE: DNA
<213> ORGANISM: Artificial
<220> FEATURE:
<223> OTHER INFORMATION: synthetic primer

<400> SEQUENCE: 123
agcgcatatc aagctttaac cggacgctcg                                          30

<210> SEQ ID NO 124
<211> LENGTH: 30

```
<212> TYPE: DNA
<213> ORGANISM: Artificial
<220> FEATURE:
<223> OTHER INFORMATION: synthetic primer

<400> SEQUENCE: 124
acaccttaac aagctttaac cggacgctcg                                     30

<210> SEQ ID NO 125
<211> LENGTH: 30
<212> TYPE: DNA
<213> ORGANISM: Artificial
<220> FEATURE:
<223> OTHER INFORMATION: synthetic primer

<400> SEQUENCE: 125
gattcactta ccgctttaac cggacgctcg                                     30

<210> SEQ ID NO 126
<211> LENGTH: 30
<212> TYPE: DNA
<213> ORGANISM: Artificial
<220> FEATURE:
<223> OTHER INFORMATION: synthetic primer

<400> SEQUENCE: 126
ggtccataga ccgctttaac cggacgctcg                                     30

<210> SEQ ID NO 127
<211> LENGTH: 30
<212> TYPE: DNA
<213> ORGANISM: Artificial
<220> FEATURE:
<223> OTHER INFORMATION: synthetic primer

<400> SEQUENCE: 127
tctaagatgg ccgctttaac cggacgctcg                                     30

<210> SEQ ID NO 128
<211> LENGTH: 30
<212> TYPE: DNA
<213> ORGANISM: Artificial
<220> FEATURE:
<223> OTHER INFORMATION: synthetic primer

<400> SEQUENCE: 128
aatgccgatc ttgctttaac cggacgctcg                                     30

<210> SEQ ID NO 129
<211> LENGTH: 30
<212> TYPE: DNA
<213> ORGANISM: Artificial
<220> FEATURE:
<223> OTHER INFORMATION: synthetic primer

<400> SEQUENCE: 129
ccaggataga ccgctttaac cggacgctcg                                     30

<210> SEQ ID NO 130
<211> LENGTH: 30
<212> TYPE: DNA
<213> ORGANISM: Artificial
<220> FEATURE:
<223> OTHER INFORMATION: synthetic primer

<400> SEQUENCE: 130
```

-continued

```
gttatgttcg aagctttaac cggacgctcg                                    30

<210> SEQ ID NO 131
<211> LENGTH: 30
<212> TYPE: DNA
<213> ORGANISM: Artificial
<220> FEATURE:
<223> OTHER INFORMATION: synthetic primer

<400> SEQUENCE: 131
ggctagtagg aagctttaac cggacgctcg                                    30

<210> SEQ ID NO 132
<211> LENGTH: 30
<212> TYPE: DNA
<213> ORGANISM: Artificial
<220> FEATURE:
<223> OTHER INFORMATION: synthetic primer

<400> SEQUENCE: 132
gtacgatatc gggctttaac cggacgctcg                                    30

<210> SEQ ID NO 133
<211> LENGTH: 30
<212> TYPE: DNA
<213> ORGANISM: Artificial
<220> FEATURE:
<223> OTHER INFORMATION: synthetic primer

<400> SEQUENCE: 133
aaccacttaa ccgctttaac cggacgctcg                                    30

<210> SEQ ID NO 134
<211> LENGTH: 30
<212> TYPE: DNA
<213> ORGANISM: Artificial
<220> FEATURE:
<223> OTHER INFORMATION: synthetic primer

<400> SEQUENCE: 134
tccgctatac gggctttaac cggacgctcg                                    30

<210> SEQ ID NO 135
<211> LENGTH: 30
<212> TYPE: DNA
<213> ORGANISM: Artificial
<220> FEATURE:
<223> OTHER INFORMATION: synthetic primer

<400> SEQUENCE: 135
actctgagac gggctttaac cggacgctcg                                    30

<210> SEQ ID NO 136
<211> LENGTH: 30
<212> TYPE: DNA
<213> ORGANISM: Artificial
<220> FEATURE:
<223> OTHER INFORMATION: synthetic primer

<400> SEQUENCE: 136
gcgtcggtag aagctttaac cggacgctcg                                    30

<210> SEQ ID NO 137
<211> LENGTH: 30
<212> TYPE: DNA
<213> ORGANISM: Artificial
```

```
<220> FEATURE:
<223> OTHER INFORMATION: synthetic primer

<400> SEQUENCE: 137
atatggtcac ttgctttaac cggacgctcg                                30

<210> SEQ ID NO 138
<211> LENGTH: 30
<212> TYPE: DNA
<213> ORGANISM: Artificial
<220> FEATURE:
<223> OTHER INFORMATION: synthetic primer

<400> SEQUENCE: 138
ttaattaatc aagctttaac cggacgctcg                                30

<210> SEQ ID NO 139
<211> LENGTH: 30
<212> TYPE: DNA
<213> ORGANISM: Artificial
<220> FEATURE:
<223> OTHER INFORMATION: synthetic primer

<400> SEQUENCE: 139
aagttgctca ccgctttaac cggacgctcg                                30

<210> SEQ ID NO 140
<211> LENGTH: 30
<212> TYPE: DNA
<213> ORGANISM: Artificial
<220> FEATURE:
<223> OTHER INFORMATION: synthetic primer

<400> SEQUENCE: 140
ggttatggag aagctttaac cggacgctcg                                30

<210> SEQ ID NO 141
<211> LENGTH: 30
<212> TYPE: DNA
<213> ORGANISM: Artificial
<220> FEATURE:
<223> OTHER INFORMATION: synthetic primer

<400> SEQUENCE: 141
tagacgaata ccgctttaac cggacgctcg                                30

<210> SEQ ID NO 142
<211> LENGTH: 30
<212> TYPE: DNA
<213> ORGANISM: Artificial
<220> FEATURE:
<223> OTHER INFORMATION: synthetic primer

<400> SEQUENCE: 142
tctacataag aagctttaac cggacgctcg                                30

<210> SEQ ID NO 143
<211> LENGTH: 30
<212> TYPE: DNA
<213> ORGANISM: Artificial
<220> FEATURE:
<223> OTHER INFORMATION: synthetic primer

<400> SEQUENCE: 143
cagaaccttc aagctttaac cggacgctcg                                30
```

```
<210> SEQ ID NO 144
<211> LENGTH: 30
<212> TYPE: DNA
<213> ORGANISM: Artificial
<220> FEATURE:
<223> OTHER INFORMATION: synthetic primer

<400> SEQUENCE: 144
caaggctcag aagctttaac cggacgctcg                              30

<210> SEQ ID NO 145
<211> LENGTH: 30
<212> TYPE: DNA
<213> ORGANISM: Artificial
<220> FEATURE:
<223> OTHER INFORMATION: synthetic primer

<400> SEQUENCE: 145
gactccacca ccgctttaac cggacgctcg                              30

<210> SEQ ID NO 146
<211> LENGTH: 30
<212> TYPE: DNA
<213> ORGANISM: Artificial
<220> FEATURE:
<223> OTHER INFORMATION: synthetic primer

<400> SEQUENCE: 146
aaccgtggag aagctttaac cggacgctcg                              30

<210> SEQ ID NO 147
<211> LENGTH: 30
<212> TYPE: DNA
<213> ORGANISM: Artificial
<220> FEATURE:
<223> OTHER INFORMATION: synthetic primer

<400> SEQUENCE: 147
ggtccttaac ttgctttaac cggacgctcg                              30

<210> SEQ ID NO 148
<211> LENGTH: 30
<212> TYPE: DNA
<213> ORGANISM: Artificial
<220> FEATURE:
<223> OTHER INFORMATION: synthetic primer

<400> SEQUENCE: 148
cgccacgccg aagctttaac cggacgctcg                              30

<210> SEQ ID NO 149
<211> LENGTH: 30
<212> TYPE: DNA
<213> ORGANISM: Artificial
<220> FEATURE:
<223> OTHER INFORMATION: synthetic primer

<400> SEQUENCE: 149
acttatacgc gggctttaac cggacgctcg                              30

<210> SEQ ID NO 150
<211> LENGTH: 30
<212> TYPE: DNA
<213> ORGANISM: Artificial
<220> FEATURE:
<223> OTHER INFORMATION: synthetic primer
```

<400> SEQUENCE: 150
ctcctcagga gggctttaac cggacgctcg                                           30

<210> SEQ ID NO 151
<211> LENGTH: 30
<212> TYPE: DNA
<213> ORGANISM: Artificial
<220> FEATURE:
<223> OTHER INFORMATION: synthetic primer

<400> SEQUENCE: 151
gtgaggtcca gggctttaac cggacgctcg                                           30

<210> SEQ ID NO 152
<211> LENGTH: 30
<212> TYPE: DNA
<213> ORGANISM: Artificial
<220> FEATURE:
<223> OTHER INFORMATION: synthetic primer

<400> SEQUENCE: 152
cacatgcgcc ttgctttaac cggacgctcg                                           30

<210> SEQ ID NO 153
<211> LENGTH: 30
<212> TYPE: DNA
<213> ORGANISM: Artificial
<220> FEATURE:
<223> OTHER INFORMATION: synthetic primer

<400> SEQUENCE: 153
gtgcacttaa gggctttaac cggacgctcg                                           30

<210> SEQ ID NO 154
<211> LENGTH: 30
<212> TYPE: DNA
<213> ORGANISM: Artificial
<220> FEATURE:
<223> OTHER INFORMATION: synthetic primer

<400> SEQUENCE: 154
ggcgtgacga gggctttaac cggacgctcg                                           30

<210> SEQ ID NO 155
<211> LENGTH: 30
<212> TYPE: DNA
<213> ORGANISM: Artificial
<220> FEATURE:
<223> OTHER INFORMATION: synthetic primer

<400> SEQUENCE: 155
aatagtgtta ccgctttaac cggacgctcg                                           30

<210> SEQ ID NO 156
<211> LENGTH: 30
<212> TYPE: DNA
<213> ORGANISM: Artificial
<220> FEATURE:
<223> OTHER INFORMATION: synthetic primer

<400> SEQUENCE: 156
cagaagctca gggctttaac cggacgctcg                                           30

<210> SEQ ID NO 157

```
<211> LENGTH: 30
<212> TYPE: DNA
<213> ORGANISM: Artificial
<220> FEATURE:
<223> OTHER INFORMATION: synthetic primer

<400> SEQUENCE: 157
tagtggcaag aagctttaac cggacgctcg                              30

<210> SEQ ID NO 158
<211> LENGTH: 30
<212> TYPE: DNA
<213> ORGANISM: Artificial
<220> FEATURE:
<223> OTHER INFORMATION: synthetic primer

<400> SEQUENCE: 158
acagactctc aagctttaac cggacgctcg                              30

<210> SEQ ID NO 159
<211> LENGTH: 30
<212> TYPE: DNA
<213> ORGANISM: Artificial
<220> FEATURE:
<223> OTHER INFORMATION: synthetic primer

<400> SEQUENCE: 159
ggatgacacc ttgctttaac cggacgctcg                              30

<210> SEQ ID NO 160
<211> LENGTH: 30
<212> TYPE: DNA
<213> ORGANISM: Artificial
<220> FEATURE:
<223> OTHER INFORMATION: synthetic primer

<400> SEQUENCE: 160
gtgagctctc aagctttaac cggacgctcg                              30

<210> SEQ ID NO 161
<211> LENGTH: 30
<212> TYPE: DNA
<213> ORGANISM: Artificial
<220> FEATURE:
<223> OTHER INFORMATION: synthetic primer

<400> SEQUENCE: 161
actccgctca gggctttaac cggacgctcg                              30

<210> SEQ ID NO 162
<211> LENGTH: 30
<212> TYPE: DNA
<213> ORGANISM: Artificial
<220> FEATURE:
<223> OTHER INFORMATION: synthetic primer

<400> SEQUENCE: 162
atcgttgacc aagctttaac cggacgctcg                              30

<210> SEQ ID NO 163
<211> LENGTH: 30
<212> TYPE: DNA
<213> ORGANISM: Artificial
<220> FEATURE:
<223> OTHER INFORMATION: synthetic primer

<400> SEQUENCE: 163
```
cagtgctata ccgctttaac cggacgctcg                                          30

<210> SEQ ID NO 164
<211> LENGTH: 30
<212> TYPE: DNA
<213> ORGANISM: Artificial
<220> FEATURE:
<223> OTHER INFORMATION: synthetic primer

<400> SEQUENCE: 164
cagtcacgga gggctttaac cggacgctcg                                          30

<210> SEQ ID NO 165
<211> LENGTH: 30
<212> TYPE: DNA
<213> ORGANISM: Artificial
<220> FEATURE:
<223> OTHER INFORMATION: synthetic primer

<400> SEQUENCE: 165
atacggcatc aagctttaac cggacgctcg                                          30

<210> SEQ ID NO 166
<211> LENGTH: 30
<212> TYPE: DNA
<213> ORGANISM: Artificial
<220> FEATURE:
<223> OTHER INFORMATION: synthetic primer

<400> SEQUENCE: 166
tgtaagaacg aagctttaac cggacgctcg                                          30

<210> SEQ ID NO 167
<211> LENGTH: 30
<212> TYPE: DNA
<213> ORGANISM: Artificial
<220> FEATURE:
<223> OTHER INFORMATION: synthetic primer

<400> SEQUENCE: 167
agctagcatc ttgctttaac cggacgctcg                                          30

<210> SEQ ID NO 168
<211> LENGTH: 30
<212> TYPE: DNA
<213> ORGANISM: Artificial
<220> FEATURE:
<223> OTHER INFORMATION: synthetic primer

<400> SEQUENCE: 168
ccaagtcctc aagctttaac cggacgctcg                                          30

<210> SEQ ID NO 169
<211> LENGTH: 30
<212> TYPE: DNA
<213> ORGANISM: Artificial
<220> FEATURE:
<223> OTHER INFORMATION: synthetic primer

<400> SEQUENCE: 169
caagtcagtc aagctttaac cggacgctcg                                          30

<210> SEQ ID NO 170
<211> LENGTH: 30
<212> TYPE: DNA

<213> ORGANISM: Artificial
<220> FEATURE:
<223> OTHER INFORMATION: synthetic primer

<400> SEQUENCE: 170
tgcggcggaa gggctttaac cggacgctcg                     30

<210> SEQ ID NO 171
<211> LENGTH: 30
<212> TYPE: DNA
<213> ORGANISM: Artificial
<220> FEATURE:
<223> OTHER INFORMATION: synthetic primer

<400> SEQUENCE: 171
ctcgcggcaa ccgctttaac cggacgctcg                     30

<210> SEQ ID NO 172
<211> LENGTH: 30
<212> TYPE: DNA
<213> ORGANISM: Artificial
<220> FEATURE:
<223> OTHER INFORMATION: synthetic primer

<400> SEQUENCE: 172
tcacctaaga ccgctttaac cggacgctcg                     30

<210> SEQ ID NO 173
<211> LENGTH: 30
<212> TYPE: DNA
<213> ORGANISM: Artificial
<220> FEATURE:
<223> OTHER INFORMATION: synthetic primer

<400> SEQUENCE: 173
ccgctagtcc ttgctttaac cggacgctcg                     30

<210> SEQ ID NO 174
<211> LENGTH: 30
<212> TYPE: DNA
<213> ORGANISM: Artificial
<220> FEATURE:
<223> OTHER INFORMATION: synthetic primer

<400> SEQUENCE: 174
agcggccggc ttgctttaac cggacgctcg                     30

<210> SEQ ID NO 175
<211> LENGTH: 30
<212> TYPE: DNA
<213> ORGANISM: Artificial
<220> FEATURE:
<223> OTHER INFORMATION: synthetic primer

<400> SEQUENCE: 175
tccgttcgca gggctttaac cggacgctcg                     30

<210> SEQ ID NO 176
<211> LENGTH: 30
<212> TYPE: DNA
<213> ORGANISM: Artificial
<220> FEATURE:
<223> OTHER INFORMATION: synthetic primer

<400> SEQUENCE: 176
ccgacagcga ccgctttaac cggacgctcg                     30

<210> SEQ ID NO 177
<211> LENGTH: 30
<212> TYPE: DNA
<213> ORGANISM: Artificial
<220> FEATURE:
<223> OTHER INFORMATION: synthetic primer

<400> SEQUENCE: 177
ccaacgttgc ttgctttaac cggacgctcg                                30

<210> SEQ ID NO 178
<211> LENGTH: 30
<212> TYPE: DNA
<213> ORGANISM: Artificial
<220> FEATURE:
<223> OTHER INFORMATION: synthetic primer

<400> SEQUENCE: 178
ctgaatcacg aagctttaac cggacgctcg                                30

<210> SEQ ID NO 179
<211> LENGTH: 30
<212> TYPE: DNA
<213> ORGANISM: Artificial
<220> FEATURE:
<223> OTHER INFORMATION: synthetic primer

<400> SEQUENCE: 179
aggacgtgtc ttgctttaac cggacgctcg                                30

<210> SEQ ID NO 180
<211> LENGTH: 30
<212> TYPE: DNA
<213> ORGANISM: Artificial
<220> FEATURE:
<223> OTHER INFORMATION: synthetic primer

<400> SEQUENCE: 180
taatagctac ttgctttaac cggacgctcg                                30

<210> SEQ ID NO 181
<211> LENGTH: 30
<212> TYPE: DNA
<213> ORGANISM: Artificial
<220> FEATURE:
<223> OTHER INFORMATION: synthetic primer

<400> SEQUENCE: 181
gtaggaaggc ttgctttaac cggacgctcg                                30

<210> SEQ ID NO 182
<211> LENGTH: 30
<212> TYPE: DNA
<213> ORGANISM: Artificial
<220> FEATURE:
<223> OTHER INFORMATION: synthetic primer

<400> SEQUENCE: 182
gtaatacagg aagctttaac cggacgctcg                                30

<210> SEQ ID NO 183
<211> LENGTH: 30
<212> TYPE: DNA
<213> ORGANISM: Artificial
<220> FEATURE:

<223> OTHER INFORMATION: synthetic primer

<400> SEQUENCE: 183
gccgcgctac ttgctttaac cggacgctcg                                    30

<210> SEQ ID NO 184
<211> LENGTH: 30
<212> TYPE: DNA
<213> ORGANISM: Artificial
<220> FEATURE:
<223> OTHER INFORMATION: synthetic primer

<400> SEQUENCE: 184
cgactctgac gggctttaac cggacgctcg                                    30

<210> SEQ ID NO 185
<211> LENGTH: 30
<212> TYPE: DNA
<213> ORGANISM: Artificial
<220> FEATURE:
<223> OTHER INFORMATION: synthetic primer

<400> SEQUENCE: 185
ctcatgccgc gggctttaac cggacgctcg                                    30

<210> SEQ ID NO 186
<211> LENGTH: 30
<212> TYPE: DNA
<213> ORGANISM: Artificial
<220> FEATURE:
<223> OTHER INFORMATION: synthetic primer

<400> SEQUENCE: 186
tcctggtgtc ttgctttaac cggacgctcg                                    30

<210> SEQ ID NO 187
<211> LENGTH: 30
<212> TYPE: DNA
<213> ORGANISM: Artificial
<220> FEATURE:
<223> OTHER INFORMATION: synthetic primer

<400> SEQUENCE: 187
cagcggccgc aagctttaac cggacgctcg                                    30

<210> SEQ ID NO 188
<211> LENGTH: 30
<212> TYPE: DNA
<213> ORGANISM: Artificial
<220> FEATURE:
<223> OTHER INFORMATION: synthetic primer

<400> SEQUENCE: 188
taacgcgtac gggctttaac cggacgctcg                                    30

<210> SEQ ID NO 189
<211> LENGTH: 30
<212> TYPE: DNA
<213> ORGANISM: Artificial
<220> FEATURE:
<223> OTHER INFORMATION: synthetic primer

<400> SEQUENCE: 189
ctaggatgaa gggctttaac cggacgctcg                                    30

```
<210> SEQ ID NO 190
<211> LENGTH: 30
<212> TYPE: DNA
<213> ORGANISM: Artificial
<220> FEATURE:
<223> OTHER INFORMATION: synthetic primer

<400> SEQUENCE: 190
gcattcgaga ccgctttaac cggacgctcg                                      30

<210> SEQ ID NO 191
<211> LENGTH: 30
<212> TYPE: DNA
<213> ORGANISM: Artificial
<220> FEATURE:
<223> OTHER INFORMATION: synthetic primer

<400> SEQUENCE: 191
tatcgtaatc gggctttaac cggacgctcg                                      30

<210> SEQ ID NO 192
<211> LENGTH: 30
<212> TYPE: DNA
<213> ORGANISM: Artificial
<220> FEATURE:
<223> OTHER INFORMATION: synthetic primer

<400> SEQUENCE: 192
agtcatgtgc aagctttaac cggacgctcg                                      30

<210> SEQ ID NO 193
<211> LENGTH: 32
<212> TYPE: DNA
<213> ORGANISM: Artificial
<220> FEATURE:
<223> OTHER INFORMATION: synthetic primer

<400> SEQUENCE: 193
ggcgcgcatc ggcaaagacg agcgccttta cg                                   32

<210> SEQ ID NO 194
<211> LENGTH: 32
<212> TYPE: DNA
<213> ORGANISM: Artificial
<220> FEATURE:
<223> OTHER INFORMATION: synthetic primer

<400> SEQUENCE: 194
cctagctgac aacaaagacg agcgccttta cg                                   32

<210> SEQ ID NO 195
<211> LENGTH: 32
<212> TYPE: DNA
<213> ORGANISM: Artificial
<220> FEATURE:
<223> OTHER INFORMATION: synthetic primer

<400> SEQUENCE: 195
acaccataga ggcaaagacg agcgccttta cg                                   32

<210> SEQ ID NO 196
<211> LENGTH: 32
<212> TYPE: DNA
<213> ORGANISM: Artificial
<220> FEATURE:
<223> OTHER INFORMATION: synthetic primer
```

```
<400> SEQUENCE: 196
ggtcacatgc ggcaaagacg agcgccttta cg                                  32

<210> SEQ ID NO 197
<211> LENGTH: 32
<212> TYPE: DNA
<213> ORGANISM: Artificial
<220> FEATURE:
<223> OTHER INFORMATION: synthetic primer

<400> SEQUENCE: 197
ctactcttcc aacaaagacg agcgccttta cg                                  32

<210> SEQ ID NO 198
<211> LENGTH: 32
<212> TYPE: DNA
<213> ORGANISM: Artificial
<220> FEATURE:
<223> OTHER INFORMATION: synthetic primer

<400> SEQUENCE: 198
tgccacacac ttcaaagacg agcgccttta cg                                  32

<210> SEQ ID NO 199
<211> LENGTH: 32
<212> TYPE: DNA
<213> ORGANISM: Artificial
<220> FEATURE:
<223> OTHER INFORMATION: synthetic primer

<400> SEQUENCE: 199
tacctagctc ttcaaagacg agcgccttta cg                                  32

<210> SEQ ID NO 200
<211> LENGTH: 32
<212> TYPE: DNA
<213> ORGANISM: Artificial
<220> FEATURE:
<223> OTHER INFORMATION: synthetic primer

<400> SEQUENCE: 200
cctaggtgga ggcaaagacg agcgccttta cg                                  32

<210> SEQ ID NO 201
<211> LENGTH: 32
<212> TYPE: DNA
<213> ORGANISM: Artificial
<220> FEATURE:
<223> OTHER INFORMATION: synthetic primer

<400> SEQUENCE: 201
gtcctgtgga cccaaagacg agcgccttta cg                                  32

<210> SEQ ID NO 202
<211> LENGTH: 32
<212> TYPE: DNA
<213> ORGANISM: Artificial
<220> FEATURE:
<223> OTHER INFORMATION: synthetic primer

<400> SEQUENCE: 202
tgcgacttcc ggcaaagacg agcgccttta cg                                  32

<210> SEQ ID NO 203
<211> LENGTH: 32
```

```
<212> TYPE: DNA
<213> ORGANISM: Artificial
<220> FEATURE:
<223> OTHER INFORMATION: synthetic primer

<400> SEQUENCE: 203
gagctccgcg ttcaaagacg agcgccttta cg                                    32

<210> SEQ ID NO 204
<211> LENGTH: 32
<212> TYPE: DNA
<213> ORGANISM: Artificial
<220> FEATURE:
<223> OTHER INFORMATION: synthetic primer

<400> SEQUENCE: 204
tacaaccaac ggcaaagacg agcgccttta cg                                    32

<210> SEQ ID NO 205
<211> LENGTH: 32
<212> TYPE: DNA
<213> ORGANISM: Artificial
<220> FEATURE:
<223> OTHER INFORMATION: synthetic primer

<400> SEQUENCE: 205
tgagtcgaag aacaaagacg agcgccttta cg                                    32

<210> SEQ ID NO 206
<211> LENGTH: 32
<212> TYPE: DNA
<213> ORGANISM: Artificial
<220> FEATURE:
<223> OTHER INFORMATION: synthetic primer

<400> SEQUENCE: 206
gacgtgataa cccaaagacg agcgccttta cg                                    32

<210> SEQ ID NO 207
<211> LENGTH: 32
<212> TYPE: DNA
<213> ORGANISM: Artificial
<220> FEATURE:
<223> OTHER INFORMATION: synthetic primer

<400> SEQUENCE: 207
tggagagagc ttcaaagacg agcgccttta cg                                    32

<210> SEQ ID NO 208
<211> LENGTH: 32
<212> TYPE: DNA
<213> ORGANISM: Artificial
<220> FEATURE:
<223> OTHER INFORMATION: synthetic primer

<400> SEQUENCE: 208
gatcgccaca cccaaagacg agcgccttta cg                                    32

<210> SEQ ID NO 209
<211> LENGTH: 32
<212> TYPE: DNA
<213> ORGANISM: Artificial
<220> FEATURE:
<223> OTHER INFORMATION: synthetic primer

<400> SEQUENCE: 209
```
gttcagagca ggcaaagacg agcgccttta cg        32

<210> SEQ ID NO 210
<211> LENGTH: 32
<212> TYPE: DNA
<213> ORGANISM: Artificial
<220> FEATURE:
<223> OTHER INFORMATION: synthetic primer

<400> SEQUENCE: 210
caatgaggca cccaaagacg agcgccttta cg        32

<210> SEQ ID NO 211
<211> LENGTH: 32
<212> TYPE: DNA
<213> ORGANISM: Artificial
<220> FEATURE:
<223> OTHER INFORMATION: synthetic primer

<400> SEQUENCE: 211
atggatgcca cccaaagacg agcgccttta cg        32

<210> SEQ ID NO 212
<211> LENGTH: 32
<212> TYPE: DNA
<213> ORGANISM: Artificial
<220> FEATURE:
<223> OTHER INFORMATION: synthetic primer

<400> SEQUENCE: 212
tatacgtcac ttcaaagacg agcgccttta cg        32

<210> SEQ ID NO 213
<211> LENGTH: 32
<212> TYPE: DNA
<213> ORGANISM: Artificial
<220> FEATURE:
<223> OTHER INFORMATION: synthetic primer

<400> SEQUENCE: 213
cataacggaa ggcaaagacg agcgccttta cg        32

<210> SEQ ID NO 214
<211> LENGTH: 32
<212> TYPE: DNA
<213> ORGANISM: Artificial
<220> FEATURE:
<223> OTHER INFORMATION: synthetic primer

<400> SEQUENCE: 214
acttcgtgga cccaaagacg agcgccttta cg        32

<210> SEQ ID NO 215
<211> LENGTH: 32
<212> TYPE: DNA
<213> ORGANISM: Artificial
<220> FEATURE:
<223> OTHER INFORMATION: synthetic primer

<400> SEQUENCE: 215
tgctggtcac ggcaaagacg agcgccttta cg        32

<210> SEQ ID NO 216
<211> LENGTH: 32
<212> TYPE: DNA
<213> ORGANISM: Artificial

```
<220> FEATURE:
<223> OTHER INFORMATION: synthetic primer

<400> SEQUENCE: 216
acgtcgatcc ttcaaagacg agcgccttta cg                                  32

<210> SEQ ID NO 217
<211> LENGTH: 32
<212> TYPE: DNA
<213> ORGANISM: Artificial
<220> FEATURE:
<223> OTHER INFORMATION: synthetic primer

<400> SEQUENCE: 217
gcaggtaaga ggcaaagacg agcgccttta cg                                  32

<210> SEQ ID NO 218
<211> LENGTH: 32
<212> TYPE: DNA
<213> ORGANISM: Artificial
<220> FEATURE:
<223> OTHER INFORMATION: synthetic primer

<400> SEQUENCE: 218
gctctaggac aacaaagacg agcgccttta cg                                  32

<210> SEQ ID NO 219
<211> LENGTH: 32
<212> TYPE: DNA
<213> ORGANISM: Artificial
<220> FEATURE:
<223> OTHER INFORMATION: synthetic primer

<400> SEQUENCE: 219
agcgcatatc aacaaagacg agcgccttta cg                                  32

<210> SEQ ID NO 220
<211> LENGTH: 32
<212> TYPE: DNA
<213> ORGANISM: Artificial
<220> FEATURE:
<223> OTHER INFORMATION: synthetic primer

<400> SEQUENCE: 220
acaccttaac aacaaagacg agcgccttta cg                                  32

<210> SEQ ID NO 221
<211> LENGTH: 32
<212> TYPE: DNA
<213> ORGANISM: Artificial
<220> FEATURE:
<223> OTHER INFORMATION: synthetic primer

<400> SEQUENCE: 221
gattcactta cccaaagacg agcgccttta cg                                  32

<210> SEQ ID NO 222
<211> LENGTH: 32
<212> TYPE: DNA
<213> ORGANISM: Artificial
<220> FEATURE:
<223> OTHER INFORMATION: synthetic primer

<400> SEQUENCE: 222
ggtccataga cccaaagacg agcgccttta cg                                  32
```

```
<210> SEQ ID NO 223
<211> LENGTH: 32
<212> TYPE: DNA
<213> ORGANISM: Artificial
<220> FEATURE:
<223> OTHER INFORMATION: synthetic primer

<400> SEQUENCE: 223
tctaagatgg cccaaagacg agcgccttta cg                                        32

<210> SEQ ID NO 224
<211> LENGTH: 32
<212> TYPE: DNA
<213> ORGANISM: Artificial
<220> FEATURE:
<223> OTHER INFORMATION: synthetic primer

<400> SEQUENCE: 224
aatgccgatc ttcaaagacg agcgccttta cg                                        32

<210> SEQ ID NO 225
<211> LENGTH: 32
<212> TYPE: DNA
<213> ORGANISM: Artificial
<220> FEATURE:
<223> OTHER INFORMATION: synthetic primer

<400> SEQUENCE: 225
ccaggataga cccaaagacg agcgccttta cg                                        32

<210> SEQ ID NO 226
<211> LENGTH: 32
<212> TYPE: DNA
<213> ORGANISM: Artificial
<220> FEATURE:
<223> OTHER INFORMATION: synthetic primer

<400> SEQUENCE: 226
gttatgttcg aacaaagacg agcgccttta cg                                        32

<210> SEQ ID NO 227
<211> LENGTH: 32
<212> TYPE: DNA
<213> ORGANISM: Artificial
<220> FEATURE:
<223> OTHER INFORMATION: synthetic primer

<400> SEQUENCE: 227
ggctagtagg aacaaagacg agcgccttta cg                                        32

<210> SEQ ID NO 228
<211> LENGTH: 32
<212> TYPE: DNA
<213> ORGANISM: Artificial
<220> FEATURE:
<223> OTHER INFORMATION: synthetic primer

<400> SEQUENCE: 228
gtacgatatc ggcaaagacg agcgccttta cg                                        32

<210> SEQ ID NO 229
<211> LENGTH: 32
<212> TYPE: DNA
<213> ORGANISM: Artificial
<220> FEATURE:
<223> OTHER INFORMATION: synthetic primer
```

<400> SEQUENCE: 229
aaccacttaa cccaaagacg agcgccttta cg                                    32

<210> SEQ ID NO 230
<211> LENGTH: 32
<212> TYPE: DNA
<213> ORGANISM: Artificial
<220> FEATURE:
<223> OTHER INFORMATION: synthetic primer

<400> SEQUENCE: 230
tccgctatac ggcaaagacg agcgccttta cg                                    32

<210> SEQ ID NO 231
<211> LENGTH: 32
<212> TYPE: DNA
<213> ORGANISM: Artificial
<220> FEATURE:
<223> OTHER INFORMATION: synthetic primer

<400> SEQUENCE: 231
actctgagac ggcaaagacg agcgccttta cg                                    32

<210> SEQ ID NO 232
<211> LENGTH: 32
<212> TYPE: DNA
<213> ORGANISM: Artificial
<220> FEATURE:
<223> OTHER INFORMATION: synthetic primer

<400> SEQUENCE: 232
gcgtcggtag aacaaagacg agcgccttta cg                                    32

<210> SEQ ID NO 233
<211> LENGTH: 32
<212> TYPE: DNA
<213> ORGANISM: Artificial
<220> FEATURE:
<223> OTHER INFORMATION: synthetic primer

<400> SEQUENCE: 233
atatggtcac ttcaaagacg agcgccttta cg                                    32

<210> SEQ ID NO 234
<211> LENGTH: 32
<212> TYPE: DNA
<213> ORGANISM: Artificial
<220> FEATURE:
<223> OTHER INFORMATION: synthetic primer

<400> SEQUENCE: 234
ttaattaatc aacaaagacg agcgccttta cg                                    32

<210> SEQ ID NO 235
<211> LENGTH: 32
<212> TYPE: DNA
<213> ORGANISM: Artificial
<220> FEATURE:
<223> OTHER INFORMATION: synthetic primer

<400> SEQUENCE: 235
aagttgctca cccaaagacg agcgccttta cg                                    32

<210> SEQ ID NO 236

```
<211> LENGTH: 32
<212> TYPE: DNA
<213> ORGANISM: Artificial
<220> FEATURE:
<223> OTHER INFORMATION: synthetic primer

<400> SEQUENCE: 236
ggttatggag aacaaagacg agcgccttta cg                            32

<210> SEQ ID NO 237
<211> LENGTH: 32
<212> TYPE: DNA
<213> ORGANISM: Artificial
<220> FEATURE:
<223> OTHER INFORMATION: synthetic primer

<400> SEQUENCE: 237
tagacgaata cccaaagacg agcgccttta cg                            32

<210> SEQ ID NO 238
<211> LENGTH: 32
<212> TYPE: DNA
<213> ORGANISM: Artificial
<220> FEATURE:
<223> OTHER INFORMATION: synthetic primer

<400> SEQUENCE: 238
tctacataag aacaaagacg agcgccttta cg                            32

<210> SEQ ID NO 239
<211> LENGTH: 32
<212> TYPE: DNA
<213> ORGANISM: Artificial
<220> FEATURE:
<223> OTHER INFORMATION: synthetic primer

<400> SEQUENCE: 239
cagaaccttc aacaaagacg agcgccttta cg                            32

<210> SEQ ID NO 240
<211> LENGTH: 32
<212> TYPE: DNA
<213> ORGANISM: Artificial
<220> FEATURE:
<223> OTHER INFORMATION: synthetic primer

<400> SEQUENCE: 240
caaggctcag aacaaagacg agcgccttta cg                            32

<210> SEQ ID NO 241
<211> LENGTH: 32
<212> TYPE: DNA
<213> ORGANISM: Artificial
<220> FEATURE:
<223> OTHER INFORMATION: synthetic primer

<400> SEQUENCE: 241
gactccacca cccaaagacg agcgccttta cg                            32

<210> SEQ ID NO 242
<211> LENGTH: 32
<212> TYPE: DNA
<213> ORGANISM: Artificial
<220> FEATURE:
<223> OTHER INFORMATION: synthetic primer

<400> SEQUENCE: 242
```
aaccgtggag aacaaagacg agcgccttta cg                32

<210> SEQ ID NO 243
<211> LENGTH: 32
<212> TYPE: DNA
<213> ORGANISM: Artificial
<220> FEATURE:
<223> OTHER INFORMATION: synthetic primer

<400> SEQUENCE: 243
ggtccttaac ttcaaagacg agcgccttta cg                32

<210> SEQ ID NO 244
<211> LENGTH: 32
<212> TYPE: DNA
<213> ORGANISM: Artificial
<220> FEATURE:
<223> OTHER INFORMATION: synthetic primer

<400> SEQUENCE: 244
cgccacgccg aacaaagacg agcgccttta cg                32

<210> SEQ ID NO 245
<211> LENGTH: 32
<212> TYPE: DNA
<213> ORGANISM: Artificial
<220> FEATURE:
<223> OTHER INFORMATION: synthetic primer

<400> SEQUENCE: 245
acttatacgc ggcaaagacg agcgccttta cg                32

<210> SEQ ID NO 246
<211> LENGTH: 32
<212> TYPE: DNA
<213> ORGANISM: Artificial
<220> FEATURE:
<223> OTHER INFORMATION: synthetic primer

<400> SEQUENCE: 246
ctcctcagga ggcaaagacg agcgccttta cg                32

<210> SEQ ID NO 247
<211> LENGTH: 32
<212> TYPE: DNA
<213> ORGANISM: Artificial
<220> FEATURE:
<223> OTHER INFORMATION: synthetic primer

<400> SEQUENCE: 247
gtgaggtcca ggcaaagacg agcgccttta cg                32

<210> SEQ ID NO 248
<211> LENGTH: 32
<212> TYPE: DNA
<213> ORGANISM: Artificial
<220> FEATURE:
<223> OTHER INFORMATION: synthetic primer

<400> SEQUENCE: 248
cacatgcgcc ttcaaagacg agcgccttta cg                32

<210> SEQ ID NO 249
<211> LENGTH: 32
<212> TYPE: DNA

<213> ORGANISM: Artificial
<220> FEATURE:
<223> OTHER INFORMATION: synthetic primer

<400> SEQUENCE: 249
gtgcacttaa ggcaaagacg agcgccttta cg                                    32

<210> SEQ ID NO 250
<211> LENGTH: 32
<212> TYPE: DNA
<213> ORGANISM: Artificial
<220> FEATURE:
<223> OTHER INFORMATION: synthetic primer

<400> SEQUENCE: 250
ggcgtgacga ggcaaagacg agcgccttta cg                                    32

<210> SEQ ID NO 251
<211> LENGTH: 32
<212> TYPE: DNA
<213> ORGANISM: Artificial
<220> FEATURE:
<223> OTHER INFORMATION: synthetic primer

<400> SEQUENCE: 251
aatagtgtta cccaaagacg agcgccttta cg                                    32

<210> SEQ ID NO 252
<211> LENGTH: 32
<212> TYPE: DNA
<213> ORGANISM: Artificial
<220> FEATURE:
<223> OTHER INFORMATION: synthetic primer

<400> SEQUENCE: 252
cagaagctca ggcaaagacg agcgccttta cg                                    32

<210> SEQ ID NO 253
<211> LENGTH: 32
<212> TYPE: DNA
<213> ORGANISM: Artificial
<220> FEATURE:
<223> OTHER INFORMATION: synthetic primer

<400> SEQUENCE: 253
tagtggcaag aacaaagacg agcgccttta cg                                    32

<210> SEQ ID NO 254
<211> LENGTH: 32
<212> TYPE: DNA
<213> ORGANISM: Artificial
<220> FEATURE:
<223> OTHER INFORMATION: synthetic primer

<400> SEQUENCE: 254
acagactctc aacaaagacg agcgccttta cg                                    32

<210> SEQ ID NO 255
<211> LENGTH: 32
<212> TYPE: DNA
<213> ORGANISM: Artificial
<220> FEATURE:
<223> OTHER INFORMATION: synthetic primer

<400> SEQUENCE: 255
ggatgacacc ttcaaagacg agcgccttta cg                                    32

<210> SEQ ID NO 256
<211> LENGTH: 32
<212> TYPE: DNA
<213> ORGANISM: Artificial
<220> FEATURE:
<223> OTHER INFORMATION: synthetic primer

<400> SEQUENCE: 256
gtgagctctc aacaaagacg agcgccttta cg                                    32

<210> SEQ ID NO 257
<211> LENGTH: 32
<212> TYPE: DNA
<213> ORGANISM: Artificial
<220> FEATURE:
<223> OTHER INFORMATION: synthetic primer

<400> SEQUENCE: 257
actccgctca ggcaaagacg agcgccttta cg                                    32

<210> SEQ ID NO 258
<211> LENGTH: 32
<212> TYPE: DNA
<213> ORGANISM: Artificial
<220> FEATURE:
<223> OTHER INFORMATION: synthetic primer

<400> SEQUENCE: 258
atcgttgacc aacaaagacg agcgccttta cg                                    32

<210> SEQ ID NO 259
<211> LENGTH: 32
<212> TYPE: DNA
<213> ORGANISM: Artificial
<220> FEATURE:
<223> OTHER INFORMATION: synthetic primer

<400> SEQUENCE: 259
cagtgctata cccaaagacg agcgccttta cg                                    32

<210> SEQ ID NO 260
<211> LENGTH: 32
<212> TYPE: DNA
<213> ORGANISM: Artificial
<220> FEATURE:
<223> OTHER INFORMATION: synthetic primer

<400> SEQUENCE: 260
cagtcacgga ggcaaagacg agcgccttta cg                                    32

<210> SEQ ID NO 261
<211> LENGTH: 32
<212> TYPE: DNA
<213> ORGANISM: Artificial
<220> FEATURE:
<223> OTHER INFORMATION: synthetic primer

<400> SEQUENCE: 261
atacggcatc aacaaagacg agcgccttta cg                                    32

<210> SEQ ID NO 262
<211> LENGTH: 32
<212> TYPE: DNA
<213> ORGANISM: Artificial
<220> FEATURE:

<223> OTHER INFORMATION: synthetic primer

<400> SEQUENCE: 262
tgtaagaacg aacaaagacg agcgccttta cg                              32

<210> SEQ ID NO 263
<211> LENGTH: 32
<212> TYPE: DNA
<213> ORGANISM: Artificial
<220> FEATURE:
<223> OTHER INFORMATION: synthetic primer

<400> SEQUENCE: 263
agctagcatc ttcaaagacg agcgccttta cg                              32

<210> SEQ ID NO 264
<211> LENGTH: 32
<212> TYPE: DNA
<213> ORGANISM: Artificial
<220> FEATURE:
<223> OTHER INFORMATION: synthetic primer

<400> SEQUENCE: 264
ccaagtcctc aacaaagacg agcgccttta cg                              32

<210> SEQ ID NO 265
<211> LENGTH: 32
<212> TYPE: DNA
<213> ORGANISM: Artificial
<220> FEATURE:
<223> OTHER INFORMATION: synthetic primer

<400> SEQUENCE: 265
caagtcagtc aacaaagacg agcgccttta cg                              32

<210> SEQ ID NO 266
<211> LENGTH: 32
<212> TYPE: DNA
<213> ORGANISM: Artificial
<220> FEATURE:
<223> OTHER INFORMATION: synthetic primer

<400> SEQUENCE: 266
tgcggcggaa ggcaaagacg agcgccttta cg                              32

<210> SEQ ID NO 267
<211> LENGTH: 32
<212> TYPE: DNA
<213> ORGANISM: Artificial
<220> FEATURE:
<223> OTHER INFORMATION: synthetic primer

<400> SEQUENCE: 267
ctcgcggcaa cccaaagacg agcgccttta cg                              32

<210> SEQ ID NO 268
<211> LENGTH: 32
<212> TYPE: DNA
<213> ORGANISM: Artificial
<220> FEATURE:
<223> OTHER INFORMATION: synthetic primer

<400> SEQUENCE: 268
tcacctaaga cccaaagacg agcgccttta cg                              32

-continued

<210> SEQ ID NO 269
<211> LENGTH: 32
<212> TYPE: DNA
<213> ORGANISM: Artificial
<220> FEATURE:
<223> OTHER INFORMATION: synthetic primer

<400> SEQUENCE: 269
ccgctagtcc ttcaaagacg agcgccttta cg                                    32

<210> SEQ ID NO 270
<211> LENGTH: 32
<212> TYPE: DNA
<213> ORGANISM: Artificial
<220> FEATURE:
<223> OTHER INFORMATION: synthetic primer

<400> SEQUENCE: 270
agcggccggc ttcaaagacg agcgccttta cg                                    32

<210> SEQ ID NO 271
<211> LENGTH: 32
<212> TYPE: DNA
<213> ORGANISM: Artificial
<220> FEATURE:
<223> OTHER INFORMATION: synthetic primer

<400> SEQUENCE: 271
tccgttcgca ggcaaagacg agcgccttta cg                                    32

<210> SEQ ID NO 272
<211> LENGTH: 32
<212> TYPE: DNA
<213> ORGANISM: Artificial
<220> FEATURE:
<223> OTHER INFORMATION: synthetic primer

<400> SEQUENCE: 272
ccgacagcga cccaaagacg agcgccttta cg                                    32

<210> SEQ ID NO 273
<211> LENGTH: 32
<212> TYPE: DNA
<213> ORGANISM: Artificial
<220> FEATURE:
<223> OTHER INFORMATION: synthetic primer

<400> SEQUENCE: 273
ccaacgttgc ttcaaagacg agcgccttta cg                                    32

<210> SEQ ID NO 274
<211> LENGTH: 32
<212> TYPE: DNA
<213> ORGANISM: Artificial
<220> FEATURE:
<223> OTHER INFORMATION: synthetic primer

<400> SEQUENCE: 274
ctgaatcacg aacaaagacg agcgccttta cg                                    32

<210> SEQ ID NO 275
<211> LENGTH: 32
<212> TYPE: DNA
<213> ORGANISM: Artificial
<220> FEATURE:
<223> OTHER INFORMATION: synthetic primer

```
<400> SEQUENCE: 275
aggacgtgtc ttcaaagacg agcgccttta cg                              32

<210> SEQ ID NO 276
<211> LENGTH: 32
<212> TYPE: DNA
<213> ORGANISM: Artificial
<220> FEATURE:
<223> OTHER INFORMATION: synthetic primer

<400> SEQUENCE: 276
taatagctac ttcaaagacg agcgccttta cg                              32

<210> SEQ ID NO 277
<211> LENGTH: 32
<212> TYPE: DNA
<213> ORGANISM: Artificial
<220> FEATURE:
<223> OTHER INFORMATION: synthetic primer

<400> SEQUENCE: 277
gtaggaaggc ttcaaagacg agcgccttta cg                              32

<210> SEQ ID NO 278
<211> LENGTH: 32
<212> TYPE: DNA
<213> ORGANISM: Artificial
<220> FEATURE:
<223> OTHER INFORMATION: synthetic primer

<400> SEQUENCE: 278
gtaatacagg aacaaagacg agcgccttta cg                              32

<210> SEQ ID NO 279
<211> LENGTH: 32
<212> TYPE: DNA
<213> ORGANISM: Artificial
<220> FEATURE:
<223> OTHER INFORMATION: synthetic primer

<400> SEQUENCE: 279
gccgcgctac ttcaaagacg agcgccttta cg                              32

<210> SEQ ID NO 280
<211> LENGTH: 32
<212> TYPE: DNA
<213> ORGANISM: Artificial
<220> FEATURE:
<223> OTHER INFORMATION: synthetic primer

<400> SEQUENCE: 280
cgactctgac ggcaaagacg agcgccttta cg                              32

<210> SEQ ID NO 281
<211> LENGTH: 32
<212> TYPE: DNA
<213> ORGANISM: Artificial
<220> FEATURE:
<223> OTHER INFORMATION: synthetic primer

<400> SEQUENCE: 281
ctcatgccgc ggcaaagacg agcgccttta cg                              32

<210> SEQ ID NO 282
<211> LENGTH: 32
```

```
<212> TYPE: DNA
<213> ORGANISM: Artificial
<220> FEATURE:
<223> OTHER INFORMATION: synthetic primer

<400> SEQUENCE: 282
tcctggtgtc ttcaaagacg agcgccttta cg                              32

<210> SEQ ID NO 283
<211> LENGTH: 32
<212> TYPE: DNA
<213> ORGANISM: Artificial
<220> FEATURE:
<223> OTHER INFORMATION: synthetic primer

<400> SEQUENCE: 283
cagcggccgc aacaaagacg agcgccttta cg                              32

<210> SEQ ID NO 284
<211> LENGTH: 32
<212> TYPE: DNA
<213> ORGANISM: Artificial
<220> FEATURE:
<223> OTHER INFORMATION: synthetic primer

<400> SEQUENCE: 284
taacgcgtac ggcaaagacg agcgccttta cg                              32

<210> SEQ ID NO 285
<211> LENGTH: 32
<212> TYPE: DNA
<213> ORGANISM: Artificial
<220> FEATURE:
<223> OTHER INFORMATION: synthetic primer

<400> SEQUENCE: 285
ctaggatgaa ggcaaagacg agcgccttta cg                              32

<210> SEQ ID NO 286
<211> LENGTH: 32
<212> TYPE: DNA
<213> ORGANISM: Artificial
<220> FEATURE:
<223> OTHER INFORMATION: synthetic primer

<400> SEQUENCE: 286
gcattcgaga cccaaagacg agcgccttta cg                              32

<210> SEQ ID NO 287
<211> LENGTH: 32
<212> TYPE: DNA
<213> ORGANISM: Artificial
<220> FEATURE:
<223> OTHER INFORMATION: synthetic primer

<400> SEQUENCE: 287
tatcgtaatc ggcaaagacg agcgccttta cg                              32

<210> SEQ ID NO 288
<211> LENGTH: 32
<212> TYPE: DNA
<213> ORGANISM: Artificial
<220> FEATURE:
<223> OTHER INFORMATION: synthetic primer

<400> SEQUENCE: 288
```
agtcatgtgc aacaaagacg agcgccttta cg            32

<210> SEQ ID NO 289
<211> LENGTH: 32
<212> TYPE: DNA
<213> ORGANISM: Artificial
<220> FEATURE:
<223> OTHER INFORMATION: synthetic primer

<400> SEQUENCE: 289
ggcgcgcatc ggcgtccatc tcgaaggagt cg            32

<210> SEQ ID NO 290
<211> LENGTH: 32
<212> TYPE: DNA
<213> ORGANISM: Artificial
<220> FEATURE:
<223> OTHER INFORMATION: synthetic primer

<400> SEQUENCE: 290
cctagctgac aacgtccatc tcgaaggagt cg            32

<210> SEQ ID NO 291
<211> LENGTH: 32
<212> TYPE: DNA
<213> ORGANISM: Artificial
<220> FEATURE:
<223> OTHER INFORMATION: synthetic primer

<400> SEQUENCE: 291
acaccataga ggcgtccatc tcgaaggagt cg            32

<210> SEQ ID NO 292
<211> LENGTH: 32
<212> TYPE: DNA
<213> ORGANISM: Artificial
<220> FEATURE:
<223> OTHER INFORMATION: synthetic primer

<400> SEQUENCE: 292
ggtcacatgc ggcgtccatc tcgaaggagt cg            32

<210> SEQ ID NO 293
<211> LENGTH: 32
<212> TYPE: DNA
<213> ORGANISM: Artificial
<220> FEATURE:
<223> OTHER INFORMATION: synthetic primer

<400> SEQUENCE: 293
ctactcttcc aacgtccatc tcgaaggagt cg            32

<210> SEQ ID NO 294
<211> LENGTH: 32
<212> TYPE: DNA
<213> ORGANISM: Artificial
<220> FEATURE:
<223> OTHER INFORMATION: synthetic primer

<400> SEQUENCE: 294
tgccacacac ttcgtccatc tcgaaggagt cg            32

<210> SEQ ID NO 295
<211> LENGTH: 32
<212> TYPE: DNA
<213> ORGANISM: Artificial

```
<220> FEATURE:
<223> OTHER INFORMATION: synthetic primer

<400> SEQUENCE: 295
tacctagctc ttcgtccatc tcgaaggagt cg                            32

<210> SEQ ID NO 296
<211> LENGTH: 32
<212> TYPE: DNA
<213> ORGANISM: Artificial
<220> FEATURE:
<223> OTHER INFORMATION: synthetic primer

<400> SEQUENCE: 296
cctaggtgga ggcgtccatc tcgaaggagt cg                            32

<210> SEQ ID NO 297
<211> LENGTH: 32
<212> TYPE: DNA
<213> ORGANISM: Artificial
<220> FEATURE:
<223> OTHER INFORMATION: synthetic primer

<400> SEQUENCE: 297
gtcctgtgga cccgtccatc tcgaaggagt cg                            32

<210> SEQ ID NO 298
<211> LENGTH: 32
<212> TYPE: DNA
<213> ORGANISM: Artificial
<220> FEATURE:
<223> OTHER INFORMATION: synthetic primer

<400> SEQUENCE: 298
tgcgacttcc ggcgtccatc tcgaaggagt cg                            32

<210> SEQ ID NO 299
<211> LENGTH: 32
<212> TYPE: DNA
<213> ORGANISM: Artificial
<220> FEATURE:
<223> OTHER INFORMATION: synthetic primer

<400> SEQUENCE: 299
gagctccgcg ttcgtccatc tcgaaggagt cg                            32

<210> SEQ ID NO 300
<211> LENGTH: 32
<212> TYPE: DNA
<213> ORGANISM: Artificial
<220> FEATURE:
<223> OTHER INFORMATION: synthetic primer

<400> SEQUENCE: 300
tacaaccaac ggcgtccatc tcgaaggagt cg                            32

<210> SEQ ID NO 301
<211> LENGTH: 32
<212> TYPE: DNA
<213> ORGANISM: Artificial
<220> FEATURE:
<223> OTHER INFORMATION: synthetic primer

<400> SEQUENCE: 301
tgagtcgaag aacgtccatc tcgaaggagt cg                            32
```

```
<210> SEQ ID NO 302
<211> LENGTH: 32
<212> TYPE: DNA
<213> ORGANISM: Artificial
<220> FEATURE:
<223> OTHER INFORMATION: synthetic primer

<400> SEQUENCE: 302
gacgtgataa cccgtccatc tcgaaggagt cg                                    32

<210> SEQ ID NO 303
<211> LENGTH: 32
<212> TYPE: DNA
<213> ORGANISM: Artificial
<220> FEATURE:
<223> OTHER INFORMATION: synthetic primer

<400> SEQUENCE: 303
tggagagagc ttcgtccatc tcgaaggagt cg                                    32

<210> SEQ ID NO 304
<211> LENGTH: 32
<212> TYPE: DNA
<213> ORGANISM: Artificial
<220> FEATURE:
<223> OTHER INFORMATION: synthetic primer

<400> SEQUENCE: 304
gatcgccaca cccgtccatc tcgaaggagt cg                                    32

<210> SEQ ID NO 305
<211> LENGTH: 32
<212> TYPE: DNA
<213> ORGANISM: Artificial
<220> FEATURE:
<223> OTHER INFORMATION: synthetic primer

<400> SEQUENCE: 305
gttcagagca ggcgtccatc tcgaaggagt cg                                    32

<210> SEQ ID NO 306
<211> LENGTH: 32
<212> TYPE: DNA
<213> ORGANISM: Artificial
<220> FEATURE:
<223> OTHER INFORMATION: synthetic primer

<400> SEQUENCE: 306
caatgaggca cccgtccatc tcgaaggagt cg                                    32

<210> SEQ ID NO 307
<211> LENGTH: 32
<212> TYPE: DNA
<213> ORGANISM: Artificial
<220> FEATURE:
<223> OTHER INFORMATION: synthteic primer

<400> SEQUENCE: 307
atggatgcca cccgtccatc tcgaaggagt cg                                    32

<210> SEQ ID NO 308
<211> LENGTH: 32
<212> TYPE: DNA
<213> ORGANISM: Artificial
<220> FEATURE:
<223> OTHER INFORMATION: synthetic primer
```

<400> SEQUENCE: 308
tatacgtcac ttcgtccatc tcgaaggagt cg                32

<210> SEQ ID NO 309
<211> LENGTH: 32
<212> TYPE: DNA
<213> ORGANISM: Artificial
<220> FEATURE:
<223> OTHER INFORMATION: synthetic primer

<400> SEQUENCE: 309
cataacggaa ggcgtccatc tcgaaggagt cg                32

<210> SEQ ID NO 310
<211> LENGTH: 32
<212> TYPE: DNA
<213> ORGANISM: Artificial
<220> FEATURE:
<223> OTHER INFORMATION: synthetic primer

<400> SEQUENCE: 310
acttcgtgga cccgtccatc tcgaaggagt cg                32

<210> SEQ ID NO 311
<211> LENGTH: 32
<212> TYPE: DNA
<213> ORGANISM: Artificial
<220> FEATURE:
<223> OTHER INFORMATION: synthetic primer

<400> SEQUENCE: 311
tgctggtcac ggcgtccatc tcgaaggagt cg                32

<210> SEQ ID NO 312
<211> LENGTH: 32
<212> TYPE: DNA
<213> ORGANISM: Artificial
<220> FEATURE:
<223> OTHER INFORMATION: synthetic primer

<400> SEQUENCE: 312
acgtcgatcc ttcgtccatc tcgaaggagt cg                32

<210> SEQ ID NO 313
<211> LENGTH: 32
<212> TYPE: DNA
<213> ORGANISM: Artificial
<220> FEATURE:
<223> OTHER INFORMATION: synthetic primer

<400> SEQUENCE: 313
gcaggtaaga ggcgtccatc tcgaaggagt cg                32

<210> SEQ ID NO 314
<211> LENGTH: 32
<212> TYPE: DNA
<213> ORGANISM: Artificial
<220> FEATURE:
<223> OTHER INFORMATION: synthetic primer

<400> SEQUENCE: 314
gctctaggac aacgtccatc tcgaaggagt cg                32

<210> SEQ ID NO 315

```
<211> LENGTH: 32
<212> TYPE: DNA
<213> ORGANISM: Artificial
<220> FEATURE:
<223> OTHER INFORMATION: synthetic primer

<400> SEQUENCE: 315
agcgcatatc aacgtccatc tcgaaggagt cg                              32

<210> SEQ ID NO 316
<211> LENGTH: 32
<212> TYPE: DNA
<213> ORGANISM: Artificial
<220> FEATURE:
<223> OTHER INFORMATION: synthetic primer

<400> SEQUENCE: 316
acaccttaac aacgtccatc tcgaaggagt cg                              32

<210> SEQ ID NO 317
<211> LENGTH: 32
<212> TYPE: DNA
<213> ORGANISM: Artificial
<220> FEATURE:
<223> OTHER INFORMATION: synthetic primer

<400> SEQUENCE: 317
gattcactta cccgtccatc tcgaaggagt cg                              32

<210> SEQ ID NO 318
<211> LENGTH: 32
<212> TYPE: DNA
<213> ORGANISM: Artificial
<220> FEATURE:
<223> OTHER INFORMATION: synthetic primer

<400> SEQUENCE: 318
ggtccataga cccgtccatc tcgaaggagt cg                              32

<210> SEQ ID NO 319
<211> LENGTH: 32
<212> TYPE: DNA
<213> ORGANISM: Artificial
<220> FEATURE:
<223> OTHER INFORMATION: synthetic primer

<400> SEQUENCE: 319
tctaagatgg cccgtccatc tcgaaggagt cg                              32

<210> SEQ ID NO 320
<211> LENGTH: 32
<212> TYPE: DNA
<213> ORGANISM: Artificial
<220> FEATURE:
<223> OTHER INFORMATION: synthetic primer

<400> SEQUENCE: 320
aatgccgatc ttcgtccatc tcgaaggagt cg                              32

<210> SEQ ID NO 321
<211> LENGTH: 32
<212> TYPE: DNA
<213> ORGANISM: Artificial
<220> FEATURE:
<223> OTHER INFORMATION: synthetic primer

<400> SEQUENCE: 321
```
ccaggataga cccgtccatc tcgaaggagt cg                32

<210> SEQ ID NO 322
<211> LENGTH: 32
<212> TYPE: DNA
<213> ORGANISM: Artificial
<220> FEATURE:
<223> OTHER INFORMATION: synthetic primer

<400> SEQUENCE: 322
gttatgttcg aacgtccatc tcgaaggagt cg                32

<210> SEQ ID NO 323
<211> LENGTH: 32
<212> TYPE: DNA
<213> ORGANISM: Artificial
<220> FEATURE:
<223> OTHER INFORMATION: synthetic primer

<400> SEQUENCE: 323
ggctagtagg aacgtccatc tcgaaggagt cg                32

<210> SEQ ID NO 324
<211> LENGTH: 32
<212> TYPE: DNA
<213> ORGANISM: Artificial
<220> FEATURE:
<223> OTHER INFORMATION: synthetic primer

<400> SEQUENCE: 324
gtacgatatc ggcgtccatc tcgaaggagt cg                32

<210> SEQ ID NO 325
<211> LENGTH: 32
<212> TYPE: DNA
<213> ORGANISM: Artificial
<220> FEATURE:
<223> OTHER INFORMATION: synthetic primer

<400> SEQUENCE: 325
aaccacttaa cccgtccatc tcgaaggagt cg                32

<210> SEQ ID NO 326
<211> LENGTH: 32
<212> TYPE: DNA
<213> ORGANISM: Artificial
<220> FEATURE:
<223> OTHER INFORMATION: synthetic primer

<400> SEQUENCE: 326
tccgctatac ggcgtccatc tcgaaggagt cg                32

<210> SEQ ID NO 327
<211> LENGTH: 32
<212> TYPE: DNA
<213> ORGANISM: Artificial
<220> FEATURE:
<223> OTHER INFORMATION: synthetic primer

<400> SEQUENCE: 327
actctgagac ggcgtccatc tcgaaggagt cg                32

<210> SEQ ID NO 328
<211> LENGTH: 32
<212> TYPE: DNA

```
<213> ORGANISM: Artificial
<220> FEATURE:
<223> OTHER INFORMATION: synthetic primer

<400> SEQUENCE: 328
gcgtcggtag aacgtccatc tcgaaggagt cg                                    32

<210> SEQ ID NO 329
<211> LENGTH: 32
<212> TYPE: DNA
<213> ORGANISM: Artificial
<220> FEATURE:
<223> OTHER INFORMATION: synthetic primer

<400> SEQUENCE: 329
atatggtcac ttcgtccatc tcgaaggagt cg                                    32

<210> SEQ ID NO 330
<211> LENGTH: 32
<212> TYPE: DNA
<213> ORGANISM: Artificial
<220> FEATURE:
<223> OTHER INFORMATION: synthetic primer

<400> SEQUENCE: 330
ttaattaatc aacgtccatc tcgaaggagt cg                                    32

<210> SEQ ID NO 331
<211> LENGTH: 32
<212> TYPE: DNA
<213> ORGANISM: Artificial
<220> FEATURE:
<223> OTHER INFORMATION: synthetic primer

<400> SEQUENCE: 331
aagttgctca cccgtccatc tcgaaggagt cg                                    32

<210> SEQ ID NO 332
<211> LENGTH: 32
<212> TYPE: DNA
<213> ORGANISM: Artificial
<220> FEATURE:
<223> OTHER INFORMATION: synthetic primer

<400> SEQUENCE: 332
ggttatggag aacgtccatc tcgaaggagt cg                                    32

<210> SEQ ID NO 333
<211> LENGTH: 32
<212> TYPE: DNA
<213> ORGANISM: Artificial
<220> FEATURE:
<223> OTHER INFORMATION: synthetic primer

<400> SEQUENCE: 333
tagacgaata cccgtccatc tcgaaggagt cg                                    32

<210> SEQ ID NO 334
<211> LENGTH: 32
<212> TYPE: DNA
<213> ORGANISM: Artificial
<220> FEATURE:
<223> OTHER INFORMATION: synthetic primer

<400> SEQUENCE: 334
tctacataag aacgtccatc tcgaaggagt cg                                    32
```

```
<210> SEQ ID NO 335
<211> LENGTH: 32
<212> TYPE: DNA
<213> ORGANISM: Artificial
<220> FEATURE:
<223> OTHER INFORMATION: synthetic primer

<400> SEQUENCE: 335
cagaaccttc aacgtccatc tcgaaggagt cg                                     32

<210> SEQ ID NO 336
<211> LENGTH: 32
<212> TYPE: DNA
<213> ORGANISM: Artificial
<220> FEATURE:
<223> OTHER INFORMATION: synthetic primer

<400> SEQUENCE: 336
caaggctcag aacgtccatc tcgaaggagt cg                                     32

<210> SEQ ID NO 337
<211> LENGTH: 32
<212> TYPE: DNA
<213> ORGANISM: Artificial
<220> FEATURE:
<223> OTHER INFORMATION: synthetic primer

<400> SEQUENCE: 337
gactccacca cccgtccatc tcgaaggagt cg                                     32

<210> SEQ ID NO 338
<211> LENGTH: 32
<212> TYPE: DNA
<213> ORGANISM: Artificial
<220> FEATURE:
<223> OTHER INFORMATION: synthetic primer

<400> SEQUENCE: 338
aaccgtggag aacgtccatc tcgaaggagt cg                                     32

<210> SEQ ID NO 339
<211> LENGTH: 32
<212> TYPE: DNA
<213> ORGANISM: Artificial
<220> FEATURE:
<223> OTHER INFORMATION: synthetic primer

<400> SEQUENCE: 339
ggtccttaac ttcgtccatc tcgaaggagt cg                                     32

<210> SEQ ID NO 340
<211> LENGTH: 32
<212> TYPE: DNA
<213> ORGANISM: Artificial
<220> FEATURE:
<223> OTHER INFORMATION: synthetic primer

<400> SEQUENCE: 340
cgccacgccg aacgtccatc tcgaaggagt cg                                     32

<210> SEQ ID NO 341
<211> LENGTH: 32
<212> TYPE: DNA
<213> ORGANISM: Artificial
<220> FEATURE:
```

```
<223> OTHER INFORMATION: synthetic primer

<400> SEQUENCE: 341
acttatacgc ggcgtccatc tcgaaggagt cg                                    32

<210> SEQ ID NO 342
<211> LENGTH: 32
<212> TYPE: DNA
<213> ORGANISM: Artificial
<220> FEATURE:
<223> OTHER INFORMATION: synthetic primer

<400> SEQUENCE: 342
ctcctcagga ggcgtccatc tcgaaggagt cg                                    32

<210> SEQ ID NO 343
<211> LENGTH: 32
<212> TYPE: DNA
<213> ORGANISM: Artificial
<220> FEATURE:
<223> OTHER INFORMATION: synthetic primer

<400> SEQUENCE: 343
gtgaggtcca ggcgtccatc tcgaaggagt cg                                    32

<210> SEQ ID NO 344
<211> LENGTH: 32
<212> TYPE: DNA
<213> ORGANISM: Artificial
<220> FEATURE:
<223> OTHER INFORMATION: synthetic primer

<400> SEQUENCE: 344
cacatgcgcc ttcgtccatc tcgaaggagt cg                                    32

<210> SEQ ID NO 345
<211> LENGTH: 32
<212> TYPE: DNA
<213> ORGANISM: Artificial
<220> FEATURE:
<223> OTHER INFORMATION: synthetic primer

<400> SEQUENCE: 345
gtgcacttaa ggcgtccatc tcgaaggagt cg                                    32

<210> SEQ ID NO 346
<211> LENGTH: 32
<212> TYPE: DNA
<213> ORGANISM: Artificial
<220> FEATURE:
<223> OTHER INFORMATION: synthetic primer

<400> SEQUENCE: 346
ggcgtgacga ggcgtccatc tcgaaggagt cg                                    32

<210> SEQ ID NO 347
<211> LENGTH: 32
<212> TYPE: DNA
<213> ORGANISM: Artificial
<220> FEATURE:
<223> OTHER INFORMATION: synthetic primer

<400> SEQUENCE: 347
aatagtgtta cccgtccatc tcgaaggagt cg                                    32
```

```
<210> SEQ ID NO 348
<211> LENGTH: 32
<212> TYPE: DNA
<213> ORGANISM: Artificial
<220> FEATURE:
<223> OTHER INFORMATION: synthetic primer

<400> SEQUENCE: 348
cagaagctca ggcgtccatc tcgaaggagt cg                                 32

<210> SEQ ID NO 349
<211> LENGTH: 32
<212> TYPE: DNA
<213> ORGANISM: Artificial
<220> FEATURE:
<223> OTHER INFORMATION: synthetic primer

<400> SEQUENCE: 349
tagtggcaag aacgtccatc tcgaaggagt cg                                 32

<210> SEQ ID NO 350
<211> LENGTH: 32
<212> TYPE: DNA
<213> ORGANISM: Artificial
<220> FEATURE:
<223> OTHER INFORMATION: synthetic primer

<400> SEQUENCE: 350
acagactctc aacgtccatc tcgaaggagt cg                                 32

<210> SEQ ID NO 351
<211> LENGTH: 32
<212> TYPE: DNA
<213> ORGANISM: Artificial
<220> FEATURE:
<223> OTHER INFORMATION: synthetic primer

<400> SEQUENCE: 351
ggatgacacc ttcgtccatc tcgaaggagt cg                                 32

<210> SEQ ID NO 352
<211> LENGTH: 32
<212> TYPE: DNA
<213> ORGANISM: Artificial
<220> FEATURE:
<223> OTHER INFORMATION: synthetic primer

<400> SEQUENCE: 352
gtgagctctc aacgtccatc tcgaaggagt cg                                 32

<210> SEQ ID NO 353
<211> LENGTH: 32
<212> TYPE: DNA
<213> ORGANISM: Artificial
<220> FEATURE:
<223> OTHER INFORMATION: synthetic primer

<400> SEQUENCE: 353
actccgctca ggcgtccatc tcgaaggagt cg                                 32

<210> SEQ ID NO 354
<211> LENGTH: 32
<212> TYPE: DNA
<213> ORGANISM: Artificial
<220> FEATURE:
<223> OTHER INFORMATION: synthetic primer
```

<400> SEQUENCE: 354
atcgttgacc aacgtccatc tcgaaggagt cg                                      32

<210> SEQ ID NO 355
<211> LENGTH: 32
<212> TYPE: DNA
<213> ORGANISM: Artificial
<220> FEATURE:
<223> OTHER INFORMATION: synthetic primer

<400> SEQUENCE: 355
cagtgctata cccgtccatc tcgaaggagt cg                                      32

<210> SEQ ID NO 356
<211> LENGTH: 32
<212> TYPE: DNA
<213> ORGANISM: Artificial
<220> FEATURE:
<223> OTHER INFORMATION: synthetic primer

<400> SEQUENCE: 356
cagtcacgga ggcgtccatc tcgaaggagt cg                                      32

<210> SEQ ID NO 357
<211> LENGTH: 32
<212> TYPE: DNA
<213> ORGANISM: Artificial
<220> FEATURE:
<223> OTHER INFORMATION: synthetic primer

<400> SEQUENCE: 357
atacggcatc aacgtccatc tcgaaggagt cg                                      32

<210> SEQ ID NO 358
<211> LENGTH: 32
<212> TYPE: DNA
<213> ORGANISM: Artificial
<220> FEATURE:
<223> OTHER INFORMATION: synthetic primer

<400> SEQUENCE: 358
tgtaagaacg aacgtccatc tcgaaggagt cg                                      32

<210> SEQ ID NO 359
<211> LENGTH: 32
<212> TYPE: DNA
<213> ORGANISM: Artificial
<220> FEATURE:
<223> OTHER INFORMATION: synthetic primer

<400> SEQUENCE: 359
agctagcatc ttcgtccatc tcgaaggagt cg                                      32

<210> SEQ ID NO 360
<211> LENGTH: 32
<212> TYPE: DNA
<213> ORGANISM: Artificial
<220> FEATURE:
<223> OTHER INFORMATION: synthetic primer

<400> SEQUENCE: 360
ccaagtcctc aacgtccatc tcgaaggagt cg                                      32

<210> SEQ ID NO 361
<211> LENGTH: 32

<212> TYPE: DNA
<213> ORGANISM: Artificial
<220> FEATURE:
<223> OTHER INFORMATION: synthetic primer

<400> SEQUENCE: 361
caagtcagtc aacgtccatc tcgaaggagt cg                                32

<210> SEQ ID NO 362
<211> LENGTH: 32
<212> TYPE: DNA
<213> ORGANISM: Artificial
<220> FEATURE:
<223> OTHER INFORMATION: synthetic primer

<400> SEQUENCE: 362
tgcggcggaa ggcgtccatc tcgaaggagt cg                                32

<210> SEQ ID NO 363
<211> LENGTH: 32
<212> TYPE: DNA
<213> ORGANISM: Artificial
<220> FEATURE:
<223> OTHER INFORMATION: synthetic primer

<400> SEQUENCE: 363
ctcgcggcaa cccgtccatc tcgaaggagt cg                                32

<210> SEQ ID NO 364
<211> LENGTH: 32
<212> TYPE: DNA
<213> ORGANISM: Artificial
<220> FEATURE:
<223> OTHER INFORMATION: synthetic primer

<400> SEQUENCE: 364
tcacctaaga cccgtccatc tcgaaggagt cg                                32

<210> SEQ ID NO 365
<211> LENGTH: 32
<212> TYPE: DNA
<213> ORGANISM: Artificial
<220> FEATURE:
<223> OTHER INFORMATION: synthetic primer

<400> SEQUENCE: 365
ccgctagtcc ttcgtccatc tcgaaggagt cg                                32

<210> SEQ ID NO 366
<211> LENGTH: 32
<212> TYPE: DNA
<213> ORGANISM: Artificial
<220> FEATURE:
<223> OTHER INFORMATION: synthetic primer

<400> SEQUENCE: 366
agcggccggc ttcgtccatc tcgaaggagt cg                                32

<210> SEQ ID NO 367
<211> LENGTH: 32
<212> TYPE: DNA
<213> ORGANISM: Artificial
<220> FEATURE:
<223> OTHER INFORMATION: synthetic primer

<400> SEQUENCE: 367
tccgttcgca ggcgtccatc tcgaaggagt cg                                         32

<210> SEQ ID NO 368
<211> LENGTH: 32
<212> TYPE: DNA
<213> ORGANISM: Artificial
<220> FEATURE:
<223> OTHER INFORMATION: synthetic primer

<400> SEQUENCE: 368
ccgacagcga cccgtccatc tcgaaggagt cg                                         32

<210> SEQ ID NO 369
<211> LENGTH: 32
<212> TYPE: DNA
<213> ORGANISM: Artificial
<220> FEATURE:
<223> OTHER INFORMATION: synthetic primer

<400> SEQUENCE: 369
ccaacgttgc ttcgtccatc tcgaaggagt cg                                         32

<210> SEQ ID NO 370
<211> LENGTH: 32
<212> TYPE: DNA
<213> ORGANISM: Artificial
<220> FEATURE:
<223> OTHER INFORMATION: synthetic primer

<400> SEQUENCE: 370
ctgaatcacg aacgtccatc tcgaaggagt cg                                         32

<210> SEQ ID NO 371
<211> LENGTH: 32
<212> TYPE: DNA
<213> ORGANISM: Artificial
<220> FEATURE:
<223> OTHER INFORMATION: synthetic primer

<400> SEQUENCE: 371
aggacgtgtc ttcgtccatc tcgaaggagt cg                                         32

<210> SEQ ID NO 372
<211> LENGTH: 32
<212> TYPE: DNA
<213> ORGANISM: Artificial
<220> FEATURE:
<223> OTHER INFORMATION: synthetic primer

<400> SEQUENCE: 372
taatagctac ttcgtccatc tcgaaggagt cg                                         32

<210> SEQ ID NO 373
<211> LENGTH: 32
<212> TYPE: DNA
<213> ORGANISM: Artificial
<220> FEATURE:
<223> OTHER INFORMATION: synthetic primer

<400> SEQUENCE: 373
gtaggaaggc ttcgtccatc tcgaaggagt cg                                         32

<210> SEQ ID NO 374
<211> LENGTH: 32
<212> TYPE: DNA
<213> ORGANISM: Artificial

<220> FEATURE:
<223> OTHER INFORMATION: synthetic primer

<400> SEQUENCE: 374
gtaatacagg aacgtccatc tcgaaggagt cg      32

<210> SEQ ID NO 375
<211> LENGTH: 32
<212> TYPE: DNA
<213> ORGANISM: Artificial
<220> FEATURE:
<223> OTHER INFORMATION: synthetic primer

<400> SEQUENCE: 375
gccgcgctac ttcgtccatc tcgaaggagt cg      32

<210> SEQ ID NO 376
<211> LENGTH: 32
<212> TYPE: DNA
<213> ORGANISM: Artificial
<220> FEATURE:
<223> OTHER INFORMATION: synthetic primer

<400> SEQUENCE: 376
cgactctgac ggcgtccatc tcgaaggagt cg      32

<210> SEQ ID NO 377
<211> LENGTH: 32
<212> TYPE: DNA
<213> ORGANISM: Artificial
<220> FEATURE:
<223> OTHER INFORMATION: synthetic primer

<400> SEQUENCE: 377
ctcatgccgc ggcgtccatc tcgaaggagt cg      32

<210> SEQ ID NO 378
<211> LENGTH: 32
<212> TYPE: DNA
<213> ORGANISM: Artificial
<220> FEATURE:
<223> OTHER INFORMATION: synthetic primer

<400> SEQUENCE: 378
tcctggtgtc ttcgtccatc tcgaaggagt cg      32

<210> SEQ ID NO 379
<211> LENGTH: 32
<212> TYPE: DNA
<213> ORGANISM: Artificial
<220> FEATURE:
<223> OTHER INFORMATION: synthetic primer

<400> SEQUENCE: 379
cagcggccgc aacgtccatc tcgaaggagt cg      32

<210> SEQ ID NO 380
<211> LENGTH: 32
<212> TYPE: DNA
<213> ORGANISM: Artificial
<220> FEATURE:
<223> OTHER INFORMATION: synthetic primer

<400> SEQUENCE: 380
taacgcgtac ggcgtccatc tcgaaggagt cg      32

```
<210> SEQ ID NO 381
<211> LENGTH: 32
<212> TYPE: DNA
<213> ORGANISM: Artificial
<220> FEATURE:
<223> OTHER INFORMATION: synthetic primer

<400> SEQUENCE: 381
ctaggatgaa ggcgtccatc tcgaaggagt cg                                 32

<210> SEQ ID NO 382
<211> LENGTH: 32
<212> TYPE: DNA
<213> ORGANISM: Artificial
<220> FEATURE:
<223> OTHER INFORMATION: synthetic primer

<400> SEQUENCE: 382
gcattcgaga cccgtccatc tcgaaggagt cg                                 32

<210> SEQ ID NO 383
<211> LENGTH: 32
<212> TYPE: DNA
<213> ORGANISM: Artificial
<220> FEATURE:
<223> OTHER INFORMATION: synthetic primer

<400> SEQUENCE: 383
tatcgtaatc ggcgtccatc tcgaaggagt cg                                 32

<210> SEQ ID NO 384
<211> LENGTH: 32
<212> TYPE: DNA
<213> ORGANISM: Artificial
<220> FEATURE:
<223> OTHER INFORMATION: synthetic primer

<400> SEQUENCE: 384
agtcatgtgc aacgtccatc tcgaaggagt cg                                 32
```

METHODS AND KITS FOR DETECTING CONTAMINATION AND SAMPLE MISIDENTIFICATION

CLAIM OF PRIORITY

This application claims priority under 35 USC § 119(e) to U.S. Patent Application Ser. No. 62/630,942, filed on Feb. 15, 2018, the entire contents of which are hereby incorporated by reference.

BACKGROUND

Molecular biology workflows, particularly those comprising one or more nucleic acid amplification steps and those using multiple samples in the workflow, for example simultaneously or sequentially performed reactions performed in parallel or in multiplex, are prone to cross-contamination from one sample to another and/or misidentification of samples. Data generated from contaminated and/or misidentified samples can lead to confusion, wasted time, and erroneous conclusions at best. The use of data derived from clinical samples that have unknowingly become contaminated or mislabeled can lead to misdiagnosis, improper treatment regimens, or worse.

SUMMARY

The current teachings provide various methods and kits for identifying a contaminated or mislabeled sample.

Provided herein are methods for determining whether a sample has been contaminated, comprising forming a reaction composition in a partition comprising at least one spike in control, at least one adapter, and a sample; generating sample fragments; ligating the at least one adapter to the sample fragments to generate ligation products; amplifying the reaction composition to generate a multiplicity of amplification products comprising a multiplicity of ligation product amplicons and a multiplicity of spike in control amplicons; and sequencing the spike in control amplicons, wherein the presence of an amplified spike in control not associated with the reaction composition indicates the sample has been contaminated. In some embodiments, the reaction composition comprises at least two different spike in controls and at least two different adapters. In some embodiments, a concentration of the spike in control depends on the nucleic acid concentration of the sample. In some embodiments, the adapter comprises at least one of a primer binding site and a barcode. In some embodiments, the adapter comprises both a primer binding site and a barcode. In some embodiments, the presence of an amplified barcode not associated with the reaction composition indicates the sample has been contaminated.

Provided herein are methods for improving library sequencing quality comprising: forming a reaction composition in a partition comprising at least one spike in control, at least one adapter, and a sample; generating sample fragments; ligating the at least one adapter to the sample fragments to generate ligation products; amplifying the reaction composition to generate a multiplicity of amplification products comprising a multiplicity of ligation product amplicons and a multiplicity of spike in control amplicons; quantifying the library fragment products for sequencing; and excluding contaminated library fragment products from sequencing, wherein contaminated library fragment products include an amplified spike in control not associated with the reaction composition, and wherein excluding the contaminated library fragment products improves the library sequencing quality. In some embodiments, the library comprises at least one of a DNA library, an RNA library, or combinations thereof. In some embodiments, the reaction composition comprises at least two different spike in controls and at least two different adapters. In some embodiments, a concentration of the spike in control depends on the nucleic acid concentration of the sample. In some embodiments, the adapter comprises at least one of a primer binding site and a barcode. In some embodiments, the adapter comprises both a primer binding site and a barcode. In some embodiments, the presence of an amplified barcode not associated with the reaction composition indicates the sample has been contaminated.

Provided herein are also kits comprising a multiplicity of spike-in control species and a multiplicity of adapters. Some kit embodiments further comprise at least one ligase, at least one polymerase, or combinations thereof.

BRIEF DESCRIPTION OF THE FIGURES

The novel features of the disclosure are set forth with particularity in the appended claims. A better understanding of the features and advantages will be obtained by reference to the following detailed description that sets forth illustrative embodiments and accompanying drawings ("Figure" or "FIG." herein), or which:

FIG. 2 shows a Bioanalyzer trace generated with a sample comprising a unique set of control nucleotides that were combined with that sample prior to shearing the sample. Arrow A indicates the peak corresponding to the 200 base pair (bp) control nucleotide, arrow B indicates the peak corresponding to the 400 bp control nucleotide, and arrow C indicates the 600 bp control nucleotide that were added to the sample. The X-axis in FIGS. 2-4 is base pairs (bp) and the Y-axis is fluorescence units (FU).

FIG. 3 shows a Bioanalyzer trace of the same sample and set of control nucleotides as shown in FIG. 2, but the sample and control sets were sonically sheared. Arrow A indicates the nucleotide peak comprising the 200 bp control nucleotide; arrow B indicates the nucleotide peak comprising the 400 bp control nucleotide; and arrow C indicates the nucleotide peak comprising the 600 bp control nucleotide.

FIG. 4 shows a Bioanalyzer trace of the same sample and set of control nucleotides as shown in FIG. 2, but the sample and control sets were sonically sheared and the sheared nucleic acid was amplified to generate a sequencing library. Arrow A' indicates a nucleotide peak at approximately 320 bp, corresponding to the 200 bp control nucleotide that has been increased in size by 120 bp during amplification; arrow B' indicates a nucleotide peak at approximately 520 bp, corresponding to the 400 bp control nucleotide that has been increased in size by 120 bp during amplification; and arrow C' indicates a nucleotide peak at approximately 720 bp, corresponding to the 600 bp control nucleotide that has been increased in size by 120 bp during amplification.

FIGS. 5A&B show data indicative of contaminated samples, with expected contamination level shown by the dashed lines. Experimentally determined contamination obtained using a sonically-sheared (Covaris®) sample is represented by the diamond-dashed line (FIG. 5A) or solid line (FIG. 5B) and experimentally determined contamination obtained using an enzymatically-sheared sample is represented by the black line (FIG. 5A) or the black-dashed line (FIG. 5B). The x-axis represents the percent observed contaminant barcodes and the y-axis represents the percent expected contaminant barcodes in the corresponding sequencing libraries.

DETAILED DESCRIPTION

Figure 1:
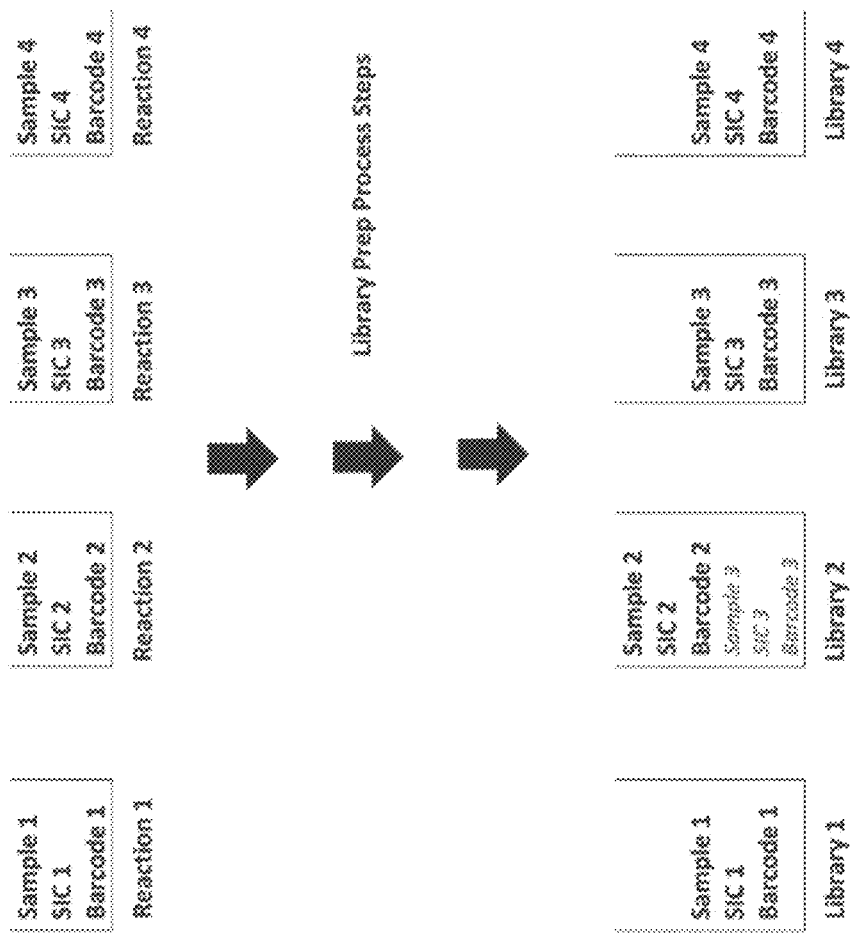
FIG. 1 shows an overview of certain aspects of exemplary method embodiments. SIC=spike-in control.

While various embodiments have been described herein, it will be evident to those skilled in the art that such embodiments are provided by way of example only. Numerous variations, changes, and substitutions may occur to those skilled in the art without departing from the disclosure. It should be understood that various alternatives to the embodiments of the disclosure described herein might be employed.

Where values are described as ranges, it will be understood that such disclosure includes the disclosure of all possible sub-ranges within such ranges, as well as specific numerical values that fall within such ranges irrespective of whether a specific numerical value or specific sub-range is expressly stated.

Where the specification includes possible combinations of such particular features, the feature can also be used, to the extent possible, in combination with and/or in the context of other particular embodiments, and in the current teachings in general.

Where reference is made to a method comprising two or more combined steps, the defined steps can be performed in any order or simultaneously (except where the context excludes that possibility), and the method includes one or more other steps which are carried out before any of the defined steps, between two of the defined steps, or after all of the defined steps (except where the context excludes that possibility).

Definitions

As used herein, the term "genome" generally refers to genomic information from a subject, which can be, for example, at least a portion or an entirety of a subject's hereditary information. A genome can comprise coding regions (e.g., that code for proteins) as well as non-coding regions. A genome can include the sequence of all chromosomes together in an organism.

As used herein, the term "subject" generally refers to an animal, such as a mammal, avian, or other organism, such as a plant. Exemplary subjects include, but are not limited to, a mammal such as a rodent, mouse, rat, rabbit, guinea pig, ungulate, horse, sheep, pig, goat, cow, cat, dog, primate; a plant such as *Arabidopsis thaliana*, corn, sorghum, oat, wheat, rice, canola, or soybean; an algae such as *Chlamydomonas reinhardtii*; a nematode such as *Caenorhabditis elegans*; an insect such as *Drosophila melanogaster*, mosquito, fruit fly, honey bee or spider; a fish such as zebrafish; a reptile; an amphibian such as a frog or *Xenopus laevis*; a Dictyostelium discoideum; a fungi such as *Pneumocystis carinii, Takifugu rubripes*, yeast, *Saccharomyces cerevisiae* or *Schizosaccharomyces pombe*; or a *Plasmodium falciparum*. A subject can also include samples obtained or derived from a prokaryote such as a bacterium, such as, *Escherichia coli*, Staphylococci or *Mycoplasma pneumoniae*; an archae; a virus such as Hepatitis C virus or human immunodeficiency virus; or a viroid.

As used herein, the term "hybridizing", "hybridize", "annealing", or "anneal" are used interchangeably to refer to the pairing of complementary nucleic acids using any process by which a strand of nucleic acid joins with a complementary strand through base pairing to form a hybridization complex. Hybridization and the strength of hybridization is impacted by such factors as the degree of complementarity between the nucleic acids, stringency of the conditions involved, the melting temperature (T) of the formed hybrid, and the G:C ratio within the nucleic acids. Conditions for hybridization in the methods disclosed herein are generally high stringency conditions as known in the art, although different stringency conditions can be used. Stringency conditions have been described, for example, in Green and Sambrook, (2012) Molecular Cloning: A Laboratory Manual, 4th edition (Cold Spring Harbor Laboratory Press); or the series Ausubel et al. eds., (2012) Current Protocols in Molecular Biology, (John Wiley & Sons, Inc.), incorporated herein by reference. High stringency conditions favor increased fidelity in hybridization, whereas reduced stringency permit lower fidelity. Stringent conditions are sequence-dependent and will be different in different circumstances. Longer sequences hybridize specifically at higher temperatures. An extensive guide to the hybridization of nucleic acids is found in Tijssen, "Overview of principles of hybridization and the strategy of nucleic acid assays" in Techniques in Biochemistry and Molecular Biology—Hybridization with Nucleic Acid Probes (1993), incorporated herein by reference.

As used herein, the term "primer extension" refers to any method wherein two nucleic acid sequences link by an overlap of their respective terminal complementary nucleic acid sequences. Such linking can be followed by an enzymatic extension of one, or both termini using the other nucleic acid sequence as a template for extension. The enzymatic extension may be performed by an enzyme including, but not limited to, a polymerase and/or a reverse transcriptase.

As used herein, the term "sequencing" generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA). Sequencing can be performed by various systems currently available, such as, without limitation, a sequencing system by Illumina®, Rocher®, Pacific Biosciences (PacBio®), Oxford Nanopore®, or Life Technologies (Ion Torrent®). Alternatively or in addition, sequencing can be performed using nucleic acid amplification, polymerase chain reaction (PCR) (e.g., digital PCR, quantitative PCR, or real time PCR), or isothermal amplification. Such systems can provide a plurality of raw genetic data corresponding to the genetic information of a subject (e.g., human), as generated by the systems from a sample provided by the subject. In some embodiments, such systems provide sequencing reads. A read can include a string of nucleic acid bases corresponding to a sequence of a nucleic acid molecule that has been sequenced.

Sample

As used herein, the term "sample" generally refers to a biological sample obtained from a subject. The biological sample can be a tissue sample, such as a biopsy, core biopsy, needle aspirate, or fine needle aspirate. The sample can be a fluid sample, such as a blood sample, urine sample, or saliva sample. The sample can be a skin sample. The sample can be a cheek swab. The sample can be a histology sample. The sample can be a histopathology sample. The sample can be a tumor sample. The sample can be fixed. The sample can be frozen. The sample can be fresh. The sample can be a plasma or serum sample. The sample can be a cell-free or cell free sample. A cell-free sample can include extracellular polynucleotides. Extracellular polynucleotides can be isolated from a bodily sample, e.g., blood, plasma, serum, urine, saliva, mucosal excretions, sputum, stool and tears. Biological samples can be derived from a homogeneous culture or population of the subjects or organisms mentioned herein or alternatively from a collection of several different organisms, for example, in a community or ecosystem.

The biological sample can comprise any number of macromolecules, for example, cellular macromolecules. In some embodiments, the cellular macromolecules refer to a nucleic acid. In some embodiments, macromolecular constituent comprises DNA. In some embodiments, the DNA is single strand DNA. In some embodiments, the DNA is double stranded DNA. In some embodiments, macromolecular constituent comprises RNA. The RNA can be coding or non-coding RNA. The RNA can be e.g., messenger RNA (mRNA), ribosomal RNA (rRNA), transfer RNA (tRNA), or microRNA (miRNA). The RNA can be a transcript. The RNA can be small RNA that are less than 200 nucleic acid bases in length, or large RNA that are greater than 200 nucleic acid bases in length. Small RNAs mainly include 5.8S ribosomal RNA (rRNA), 5S rRNA, transfer RNA (tRNA), microRNA (miRNA), small interfering RNA (siRNA), small nucleolar RNA (snoRNAs), Piwi-interacting RNA (piRNA), tRNA-derived small RNA (tsRNA) and small rDNA-derived RNA (srRNA). The RNA can be double-stranded RNA or single-stranded RNA. The RNA can be circular RNA.

Spike In Controls

The term "spike-in control", or SIC as used herein, refers to a polynucleotide of known length and sequence. The spike-in controls are designed or selected to represent unique sequences relative to the sample(s). Typically a pre-determined concentration of a spike-in control is combined with a sample, for example 1% SIC per sample. In multiplex workflows, different samples are combined with a unique SIC, which serves as an indicator of sample contamination or misidentification during the workflow. For example, sample 1 may be combined with SIC 1, sample 2 with SIC 2, sample 3 with SIC 3, and so forth. When the workflow if completed and, for example the libraries are sequenced, the presence of SIC 1 sequences in the sample 2 sequencing data indicates that sample 2 has been contaminated with sample 1 or potentially sample 2 has been mislabeled or otherwise misidentified.

In certain embodiments, the spike-in control is a single unique double-stranded oligonucleotide of known length. In some embodiments, the spike in control comprises a 50 bp fragment, a 50 bp fragment, a 100 bp fragment, a 150 bp fragment, a 200 bp fragment, a 250 bp fragment, a 300 bp fragment, a 350 bp fragment, a 400 bp fragment, a 450 bp fragment, a 500 bp fragment, a 550 bp fragment, a 600 bp fragment, a 650 bp fragment, a 700 bp fragment, a 750 bp fragment, a 800 bp fragment, a 850 bp fragment, a 900 bp fragment, a 950 bp fragment, or a 1000 bp fragment. In some embodiments, the spike in control is a known length that less than 1000 bp, 950 bp, 900 bp, 850 bp, 800 bp, 750 bp, 700 bp, 650 bp, 600 bp, 550 bp, 500 bp, 450 bp, 400 bp, 350 bp, 300 bp, 250 bp, 200 bp, 150 bp, 100 bp, or 50 bp. In some embodiments, the spike in control is between 10 bp and 1000 bp, 20 bp and 900 bp, 30 bp and 800 bp, 40 bp and 700 bp, or 50 bp and 600 bp.

In other embodiments, the spike-in control comprises two or more unique oligonucleotides of known but differing length, for example, a set comprising a 200 bp fragment, a 400 bp fragment, and a 600 bp fragment. Those in the art will appreciate that the size and number of spike-in control(s) may vary depending on the workflow in which they will be employed. For example, if the sequencing libraries generated from a multiplicity of samples according to a workflow includes a size separation step, the SICs used in that workflow should include at least one fragment that will be retained in the desired sample size. Thus a 200 bp fragment and/or a 400 bp fragment might be appropriate to include in a workflow where the end-product is a sequencing library comprising fragments of 500 bp or smaller. Likewise, a SIC set comprising a 223 bp fragment and a 408 bp fragment, for example, would also be appropriate for an exemplary workflow comprising a size selection cutoff of about 500 bp.

Nucleic Acid Fragments

In some embodiments, the sample can be manipulated in order to fragment the nucleic acids sequences contained within the sample. In some embodiments, the fragmenting is physical fragmentation. For example, a nucleic acid sample can be acoustically sheared, sonicated, or hydrodynamically sheared. Covaris® is an ultra-sonicator which is used to break DNA into 100-5 kb bp. The Bioruptor is a sonication device used for shearing chromatin, DNA, and disrupting tissues into fragments of 150-1 kb bp. Nebulizers can also be used to atomize liquid using compressed air, shearing DNA into 100-3 kb fragments. In some embodiments, the fragmenting is enzymatic. For example, restriction endonucleases, such as DNase I, non-specific nucleases, or transposases. The combination of a non-specific nuclease and T7 Endo produce non-specific nicks and counter nicks that cause the nucleic acids to disassociate. Tagmentation uses a transposase to simultaneously fragment and insert adapters onto dsDNA. RNAse III cleaves RNA into small fragments. In some embodiments, the fragmenting is a chemical fragmentation. For example, heat digestion of RNA with a divalent metal cation (magnesium or zinc) can cleave the sample into fragments.

In some embodiments, lysis agents are used to disrupt the cell. Examples of lysis agents include bioactive reagents, such as lysis enzymes that are used for lysis of different cell types, e.g., gram positive or negative bacteria, plants, yeast, mammalian, etc., such as lysozymes, achromopeptidase, lysostaphin, labiase, kitalase, lyticase, as well as other commercially available lysis enzymes. In some cases, lysis solutions can include non-ionic surfactants such as, for example, Triton™ X-100 and Tween® 20. In some cases, lysis solutions can include ionic surfactants such as, for example, sarcosyl and sodium dodecyl sulfate (SDS). Electroporation, thermal, acoustic, or mechanical cellular disruption can also be used in certain cases, where any pore size of the encapsulate is sufficiently small to retain nucleic acid fragments of a given size, following cellular disruption.

In addition to lysis agents, other reagents can be added to interact with the sample, including, for example, DNase and RNase inactivating agents or inhibitors, such as proteinase K, chelating agents, such as EDTA, and other reagents employed in removing or otherwise reducing negative activity or impact of different cell lysate components on subsequent processing of nucleic acids. In addition, in the case of encapsulated biological particles, the biological particles can be exposed to an appropriate stimulus to release the nucleic acids. Additional reagents can also include reverse transcriptase enzymes, including enzymes with terminal transferase activity, primers and oligonucleotides.

Additional reagents can also be added, such as endonucleases to fragment DNA, DNA polymerase enzymes, and dNTPs used to amplify the nucleic acid and to attach the barcode to the amplified fragments. Other enzymes can be used, including without limitation, polymerase, transposase, ligase, proteinase K, DNAse, etc. Additional reagents can also include reverse transcriptase enzymes, including enzymes with terminal transferase activity, primers and oligonucleotides.

Spike in Control Primers

In some embodiments, the methods and kits described herein comprise spike in control primers. In some embodiments, spike-in control (SIC) primer sets consist of at least one forward and at least one reverse primer. Exemplary primer sets of the Figures correspond to 200 bp, 400 bp, and 600 bp amplicons from cpX 174 gDNA. Each amplicon comprises a 12 nucleotide tag that is unique to the amplicons generated from that primer set. In some embodiments, the spike in control primers comprise one or more of the exemplary sequences of Table 1.

TABLE 1

| SEQ ID NO | EXEMPLARY SEQUENCE |
|---|---|
| 1 | GGCGCGCATCGGGGCTTGCGTTTATGGTACGC |
| 2 | CCTAGCTGACAAGGCTTGCGTTTATGGTACGC |
| 3 | ACACCATAGAGGGGCTTGCGTTTATGGTACGC |
| 4 | GGTCACATGCGGGGCTTGCGTTTATGGTACGC |
| 5 | CTACTCTTCCAAGGCTTGCGTTTATGGTACGC |
| 6 | TGCCACACACTTGGCTTGCGTTTATGGTACGC |
| 7 | TACCTAGCTCTTGGCTTGCGTTTATGGTACGC |
| 8 | CCTAGGTGGAGGGGCTTGCGTTTATGGTACGC |
| 9 | GTCCTGTGGACCGGCTTGCGTTTATGGTACGC |
| 10 | TGCGACTTCCGGGGCTTGCGTTTATGGTACGC |
| 11 | GAGCTCCGCGTTGGCTTGCGTTTATGGTACGC |
| 12 | TACAACCAACGGGGCTTGCGTTTATGGTACGC |
| 13 | TGAGTCGAAGAAGGCTTGCGTTTATGGTACGC |
| 14 | GACGTGATAACCGGCTTGCGTTTATGGTACGC |
| 15 | TGGAGAGAGCTTGGCTTGCGTTTATGGTACGC |
| 16 | GATCGCCACACCGGCTTGCGTTTATGGTACGC |
| 17 | GTTCAGAGCAGGGCTTGCGTTTATGGTACGC |
| 18 | CAATGAGGCACCGGCTTGCGTTTATGGTACGC |
| 19 | ATGGATGCCACCGGCTTGCGTTTATGGTACGC |
| 20 | TATACGTCACTTGGCTTGCGTTTATGGTACGC |
| 21 | CATAACGGAAGGGCTTGCGTTTATGGTACGC |
| 22 | ACTTCGTGGACCGGCTTGCGTTTATGGTACGC |
| 23 | TGCTGGTCACGGGCTTGCGTTTATGGTACGC |
| 24 | ACGTCGATCCTTGGCTTGCGTTTATGGTACGC |
| 25 | GCAGGTAAGAGGGCTTGCGTTTATGGTACGC |
| 26 | GCTCTAGGACAAGGCTTGCGTTTATGGTACGC |
| 27 | AGCGCATATCAAGGCTTGCGTTTATGGTACGC |
| 28 | ACACCTTAACAAGGCTTGCGTTTATGGTACGC |
| 29 | GATTCACTTACCGGCTTGCGTTTATGGTACGC |

TABLE 1-continued

| SEQ ID NO | EXEMPLARY SEQUENCE |
|---|---|
| 30 | GGTCCATAGACCGGCTTGCGTTTATGGTACGC |
| 31 | TCTAAGATGGCCGGCTTGCGTTTATGGTACGC |
| 32 | AATGCCGATCTTGGCTTGCGTTTATGGTACGC |
| 33 | CCAGGATAGACCGGCTTGCGTTTATGGTACGC |
| 34 | GTTATGTTCGAAGGCTTGCGTTTATGGTACGC |
| 35 | GGCTAGTAGGAAGGCTTGCGTTTATGGTACGC |
| 36 | GTACGATATCGGGGCTTGCGTTTATGGTACGC |
| 37 | AACCACTTAACCGGCTTGCGTTTATGGTACGC |
| 38 | TCCGCTATACGGGGCTTGCGTTTATGGTACGC |
| 39 | ACTCTGAGACGGGGCTTGCGTTTATGGTACGC |
| 40 | GCGTCGGTAGAAGGCTTGCGTTTATGGTACGC |
| 41 | ATATGGTCACTTGGCTTGCGTTTATGGTACGC |
| 42 | TTAATTAATCAAGGCTTGCGTTTATGGTACGC |
| 43 | AAGTTGCTCACCGGCTTGCGTTTATGGTACGC |
| 44 | GGTTATGGAGAAGGCTTGCGTTTATGGTACGC |
| 45 | TAGACGAATACCGGCTTGCGTTTATGGTACGC |
| 46 | TCTACATAAGAAGGCTTGCGTTTATGGTACGC |
| 47 | CAGAACCTTCAAGGCTTGCGTTTATGGTACGC |
| 48 | CAAGGCTCAGAAGGCTTGCGTTTATGGTACGC |
| 49 | GACTCCACCACCGGCTTGCGTTTATGGTACGC |
| 50 | AACCGTGGAGAAGGCTTGCGTTTATGGTACGC |
| 51 | GGTCCTTAACTTGGCTTGCGTTTATGGTACGC |
| 52 | CGCCACGCCGAAGGCTTGCGTTTATGGTACGC |
| 53 | ACTTATACGCGGGGCTTGCGTTTATGGTACGC |
| 54 | CTCCTCAGGAGGGCTTGCGTTTATGGTACGC |
| 55 | GTGAGGTCCAGGGGCTTGCGTTTATGGTACGC |
| 56 | CACATGCGCCTTGGCTTGCGTTTATGGTACGC |
| 57 | GTGCACTTAAGGGCTTGCGTTTATGGTACGC |
| 58 | GGCGTGACGAGGGCTTGCGTTTATGGTACGC |
| 59 | AATAGTGTTACCGGCTTGCGTTTATGGTACGC |
| 60 | CAGAAGCTCAGGGGCTTGCGTTTATGGTACGC |
| 61 | TAGTGGCAAGAAGGCTTGCGTTTATGGTACGC |
| 62 | ACAGACTCTCAAGGCTTGCGTTTATGGTACGC |
| 63 | GGATGACACCTTGGCTTGCGTTTATGGTACGC |
| 64 | GTGAGCTCTCAAGGCTTGCGTTTATGGTACGC |
| 65 | ACTCCGCTCAGGGGCTTGCGTTTATGGTACGC |
| 66 | ATCGTTGACCAAGGCTTGCGTTTATGGTACGC |
| 67 | CAGTGCTATACCGGCTTGCGTTTATGGTACGC |
| 68 | CAGTCACGGAGGGCTTGCGTTTATGGTACGC |

TABLE 1-continued

| SEQ ID NO | EXEMPLARY SEQUENCE |
|---|---|
| 69 | ATACGGCATCAAGGCTTGCGTTTATGGTACGC |
| 70 | TGTAAGAACGAAGGCTTGCGTTTATGGTACGC |
| 71 | AGCTAGCATCTTGGCTTGCGTTTATGGTACGC |
| 72 | CCAAGTCCTCAAGGCTTGCGTTTATGGTACGC |
| 73 | CAAGTCAGTCAAGGCTTGCGTTTATGGTACGC |
| 74 | TGCGGCGGAAGGGGCTTGCGfTTTATGGTACGC |
| 75 | CTCGCGGCAACCGGCTTGCGTTTATGGTACGC |
| 76 | TCACCTAAGACCGGCTTGCGTTTATGGTACGC |
| 77 | CCGCTAGTCCTTGGCTTGCGTTTATGGTACGC |
| 78 | AGCGGCCGGCTTGGCTTGCGTTTATGGTACGC |
| 79 | TCCGTTCGCAGGGGCTTGCGTTTATGGTACGC |
| 80 | CCGACAGCGACCGGCTTGCGTTTATGGTACGC |
| 81 | CCAACGTTGCTTGGCTTGCGTTTATGGTACGC |
| 82 | CTGAATCACGAAGGCTTGCGTTTATGGTACGC |
| 83 | AGGACGTGTCTTGGCTTGCGTTTATGGTACGC |
| 84 | TAATAGCTACTTGGCTTGCGTTTATGGTACGC |
| 85 | GTAGGAAGGCTTGGCTTGCGTTTATGGTACGC |
| 86 | GTAATACAGGAAGGCTTGCGTTTATGGTACGC |
| 87 | GCCGCGCTACTTGGCTTGCGTTTATGGTACGC |
| 88 | CGACTCTGACGGGGCTTGCGTTTATGGTACGC |
| 89 | CTCATGCCGCGGGGCTTGCGTTTATGGTACGC |
| 90 | TCCTGGTGTCTTGGCTTGCGTTTATGGTACGC |
| 91 | CAGCGGCCGCAAGGCTTGCGTTTATGGTACGC |
| 92 | TAACGCGTACGGGGCTTGCGTTTATGGTACGC |
| 93 | CTAGGATGAAGGGGCTTGCGTTTATGGTACGC |
| 94 | GCATTCGAGACCGGCTTGCGTTTATGGTACGC |
| 95 | TATCGTAATCGGGGCTTGCGTTTATGGTACGC |
| 96 | AGTCATGTGCAAGGCTTGCGTTTATGGTACGC |
| 97 | GGCGCGCATCGGGCTTTAACCGGACGCTCG |
| 98 | CCTAGCTGACAAGCTTTAACCGGACGCTCG |
| 99 | ACACCATAGAGGGCTTTAACCGGACGCTCG |
| 100 | GGTCACATGCGGGCTTTAACCGGACGCTCG |
| 101 | CTACTCTTCCAAGCTTTAACCGGACGCTCG |
| 102 | TGCCACACACTTGCTTTAACCGGACGCTCG |
| 103 | TACCTAGCTCTTGCTTTAACCGGACGCTCG |
| 104 | CCTAGGTGGAGGGCTTTAACCGGACGCTCG |
| 105 | GTCCTGTGGACCGCTTTAACCGGACGCTCG |
| 106 | TGCGACTTCCGGGCTTTAACCGGACGCTCG |
| 107 | GAGCTCCGCGTTGCTTTAACCGGACGCTCG |
| 108 | TACAACCAACGGGCTTTAACCGGACGCTCG |
| 109 | TGAGTCGAAGAAGCTTTAACCGGACGCTCG |
| 110 | GACGTGATAACCGCTTTAACCGGACGCTCG |
| 111 | TGGAGAGAGCTTGCTTTAACCGGACGCTCG |
| 112 | GATCGCCACACCGCTTTAACCGGACGCTCG |
| 113 | GTTCAGAGCAGGGCTTTAACCGGACGCTCG |
| 114 | CAATGAGGCACCGCTTTAACCGGACGCTCG |
| 115 | ATGGATGCCACCGCTTTAACCGGACGCTCG |
| 116 | TATACGTCACTTGCTTTAACCGGACGCTCG |
| 117 | CATAACGGAAGGGCTTTAACCGGACGCTCG |
| 118 | ACTTCGTGGACCGCTTTAACCGGACGCTCG |
| 119 | TGCTGGTCACGGGCTTTAACCGGACGCTCG |
| 120 | ACGTCGATCCTTGCTTTAACCGGACGCTCG |
| 121 | GCAGGTAAGAGGGCTTTAACCGGACGCTCG |
| 122 | GCTCTAGGACAAGCTTTAACCGGACGCTCG |
| 123 | AGCGCATATCAAGCTTTAACCGGACGCTCG |
| 124 | ACACCTTAACAAGCTTTAACCGGACGCTCG |
| 125 | GATTCACTTACCGCTTTAACCGGACGCTCG |
| 126 | GGTCCATAGACCGCTTTAACCGGACGCTCG |
| 127 | TCTAAGATGGCCGCTTTAACCGGACGCTCG |
| 128 | AATGCCGATCTTGCTTTAACCGGACGCTCG |
| 129 | CCAGGATAGACCGCTTTAACCGGACGCTCG |
| 130 | GTTATGTTCGAAGCTTTAACCGGACGCTCG |
| 131 | GGCTAGTAGGAAGCTTTAACCGGACGCTCG |
| 132 | GTACGATATCGGGCTTTAACCGGACGCTCG |
| 133 | AACCACTTAACCGCTTTAACCGGACGCTCG |
| 134 | TCCGCTATACGGCTTTAACCGGACGCTCG |
| 135 | ACTCTGAGACGGGCTTTAACCGGACGCTCG |
| 136 | GCGTCGGTAGAAGCTTTAACCGGACGCTCG |
| 137 | ATATGGTCACTTGCTTTAACCGGACGCTCG |
| 138 | TTAATTAATCAAGCTTTAACCGGACGCTCG |
| 139 | AAGTTGCTCACCGCTTTAACCGGACGCTCG |
| 140 | GGTTATGGAGAAGCTTTAACCGGACGCTCG |
| 141 | TAGACGAATACCGCTTTAACCGGACGCTCG |
| 142 | TCTACATAAGAAGCTTTAACCGGACGCTCG |
| 143 | CAGAACCTCAAGCTTTAACCGGACGCTCG |
| 144 | CAAGGCTCAGAAGCTTTAACCGGACGCTCG |
| 145 | GACTCCACCACCGCTTTAACCGGACGCTCG |
| 146 | AACCGTGGAGAAGCTTTAACCGGACGCTCG |

TABLE 1-continued

| SEQ ID NO | EXEMPLARY SEQUENCE |
|---|---|
| 147 | GGTCCTTAACTTGCTTTAACCGGACGCTCG |
| 148 | CGCCACGCCGAAGCTTTAACCGGACGCTCG |
| 149 | ACTTATACGCGGGCTTTAACCGGACGCTCG |
| 150 | CTCCTCAGGAGGGCTTTAACCGGACGCTCG |
| 151 | GTGAGGTCCAGGGCTTTAACCGGACGCTCG |
| 152 | CACATGCGCCTTGCTTTAACCGGACGCTCG |
| 153 | GTGCACTTAAGGGCTTTAACCGGACGCTCG |
| 154 | GGCGTGACGAGGGCTTTAACCGGACGCTCG |
| 155 | AATAGTGTTACCGCTTTAACCGGACGCTCG |
| 156 | CAGAAGCTCAGGGCTTTAACCGGACGCTCG |
| 157 | TAGTGGCAAGAAGCTTTAACCGGACGCTCG |
| 158 | ACAGACTCTCAAGCTTTAACCGGACGCTCG |
| 159 | GGATGACACCTTGCTTTAACCGGACGCTCG |
| 160 | GTGAGCTCTCAAGCTTTAACCGGACGCTCG |
| 161 | ACTCCGCTCAGGGCTTTAACCGGACGCTCG |
| 162 | ATCGTTGACCAAGCTTTAACCGGACGCTCG |
| 163 | CAGTGCTATACCGCTTTAACCGGACGCTCG |
| 164 | CAGTCACGGAGGGCTTTAACCGGACGCTCG |
| 165 | ATACGGCATCAAGCTTTAACCGGACGCTCG |
| 166 | TGTAAGAACGAAGCTTTAACCGGACGCTCG |
| 167 | AGCTAGCATCTTGCTTTAACCGGACGCTCG |
| 168 | CCAAGTCCTCAAGCTTTAACCGGACGCTCG |
| 169 | CAAGTCAGTCAAGCTTTAACCGGACGCTCG |
| 170 | TGCGGCGGAAGGGCTTTAACCGGACGCTCG |
| 171 | CTCGCGGCAACCGCTTTAACCGGACGCTCG |
| 172 | TCACCTAAGACCGCTTTAACCGGACGCTCG |
| 173 | CCGCTAGTCCTTGCTTTAACCGGACGCTCG |
| 174 | AGCGGCCGGCTTGCTTTAACCGGACGCTCG |
| 175 | TCCGTTCGCAGGGCTTTAACCGGACGCTCG |
| 176 | CCGACAGCGACCGCTTTAACCGGACGCTCG |
| 177 | CCAACGTTGCTTGCTTTAACCGGACGCTCG |
| 178 | CTGAATCACGAAGCTTTAACCGGACGCTCG |
| 179 | AGGACGTGTCTTGCTTTAACCGGACGCTCG |
| 180 | TAATAGCTACTTGCTTTAACCGGACGCTCG |
| 181 | GTAGGAAGGCTTGCTTTAACCGGACGCTCG |
| 182 | GTAATACAGGAAGCTTTAACCGGACGCTCG |
| 183 | GCCGCGCTACTTGCTTTAACCGGACGCTCG |
| 184 | CGACTCTGACGGGCTTTAACCGGACGCTCG |
| 185 | CTCATGCCGCGGGCTTTAACCGGACGCTCG |

TABLE 1-continued

| SEQ ID NO | EXEMPLARY SEQUENCE |
|---|---|
| 186 | TCCTGGTGTCTTGCTTTAACCGGACGCTCG |
| 187 | CAGCGGCCGCAAGCTTTAACCGGACGCTCG |
| 188 | TAACGCGTACGGGCTTTAACCGGACGCTCG |
| 189 | CTAGGATGAAGGGCTTTAACCGGACGCTCG |
| 190 | GCATTCGAGACCGCTTTAACCGGACGCTCG |
| 191 | TATCGTAATCGGGCTTTAACCGGACGCTCG |
| 192 | AGTCATGTGCAAGCTTTAACCGGACGCTCG |
| 193 | GGCGCGCATCGGCAAAGACGAGCGCCTTTACG |
| 194 | CCTAGCTGACAACAAAGACGAGCGCCTTTACG |
| 195 | ACACCATAGAGGCAAAGACGAGCGCCTTTACG |
| 196 | GGTCACATGCGGCAAAGACGAGCGCCTTTACG |
| 197 | CTACTCTTCCAACAAAGACGAGCGCCTTTACG |
| 198 | TGCCACACACTTCAAAGACGAGCGCCTTTACG |
| 199 | TACCTAGCTCTTCAAAGACGAGCGCCTTTACG |
| 200 | CCTAGGTGGAGGCAAAGACGAGCGCCTTTACG |
| 201 | GTCCTGTGGACCCAAAGACGAGCGCCTTTACG |
| 202 | TGCGACTTCCGGCAAAGACGAGCGCCTTTACG |
| 203 | GAGCTCCGCGTTCAAAGACGAGCGCCTTTACG |
| 204 | TACAACCAACGGCAAAGACGAGCGCCTTTACG |
| 205 | TGAGTCGAAGAACAAAGACGAGCGCCTTTACG |
| 206 | GACGTGATAACCCAAAGACGAGCGCCTTTACG |
| 207 | TGGAGAGAGCTTCAAAGACGAGCGCCTTTACG |
| 208 | GATCGCCACACCCAAAGACGAGCGCCTTTACG |
| 209 | GTTCAGAGCAGGCAAAGACGAGCGCCTTTACG |
| 210 | CAATGAGGCACCCAAAGACGAGCGCCTTTACG |
| 211 | ATGGATGCCACCCAAAGACGAGCGCCTTTACG |
| 212 | TATACGTCACTTCAAAGACGAGCGCCTTTACG |
| 213 | CATAACGGAAGGCAAAGACGAGCGCCTTTACG |
| 214 | ACTTCGTGGACCCAAAGACGAGCGCCTTTACG |
| 215 | TGCTGGTCACGGCAAAGACGAGCGCCTTTACG |
| 216 | ACGTCGATCCTTCAAAGACGAGCGCCTTTACG |
| 217 | GCAGGTAAGAGGCAAAGACGAGCGCCTTTACG |
| 218 | GCTCTAGGACAACAAAGACGAGCGCCTTTACG |
| 219 | AGCGCATATCAACAAAGACGAGCGCCTTTACG |
| 220 | ACACCTTAACAACAAAGACGAGCGCCTTTACG |
| 221 | GATTCACTTACCCAAAGACGAGCGCCTTTACG |
| 222 | GGTCCATAGACCCAAAGACGAGCGCCTTTACG |
| 223 | TCTAAGATGCCCAAAGACGAGCGCCTTTACG |
| 224 | AATGCCGATCTTCAAAGACGAGCGCCTTTACG |

TABLE 1-continued

| SEQ ID NO | EXEMPLARY SEQUENCE |
|---|---|
| 225 | CCAGGATAGACCCAAAGACGAGCGCCTTTACG |
| 226 | GTTATGTTCGAACAAAGACGAGCGCCTTTACG |
| 227 | GGCTAGTAGGAACAAAGACGAGCGCCTTTACG |
| 228 | GTACGATATCGGCAAAGACGAGCGCCTTTACG |
| 229 | AACCACTTAACCCAAAGACGAGCGCCTTTACG |
| 230 | TCCGCTATACGGCAAAGACGAGCGCCTTTACG |
| 231 | ACTCTGAGACGGCAAAGACGAGCGCCTTTACG |
| 232 | GCGTCGGTAGAACAAAGACGAGCGCCTTTACG |
| 233 | ATATGGTCACTTCAAAGACGAGCGCCTTTACG |
| 234 | TTAATTAATCAACAAAGACGAGCGCCTTTACG |
| 235 | AAGTTGCTCACCCAAAGACGAGCGCCTTTACG |
| 236 | GGTTATGGAGAACAAAGACGAGCGCCTTTACG |
| 237 | TAGACGAATACCCAAAGACGAGCGCCTTTACG |
| 238 | TCTACATAAGAACAAAGACGAGCGCCTTTACG |
| 239 | CAGAACCTTCAACAAAGACGAGCGCCTTTACG |
| 240 | CAAGGCTCAGAACAAAGACGAGCGCCTTTACG |
| 241 | GACTCCACCACCCAAAGACGAGCGCCTTTACG |
| 242 | AACCGTGGAGAACAAAGACGAGCGCCTTTACG |
| 243 | GGTCCTTAACTTCAAAGACGAGCGCCTTTACG |
| 244 | CGCCACGCCGAACAAAGACGAGCGCCTTTACG |
| 245 | ACTTATACGCGGCAAAGACGAGCGCCTTTACG |
| 246 | CTCCTCAGGAGGCAAAGACGAGCGCCTTTACG |
| 247 | GTGAGGTCCAGGCAAAGACGAGCGCCTTTACG |
| 248 | CACATGCGCCTTCAAAGACGAGCGCCTTTACG |
| 249 | GTGCACTTAAGGCAAAGACGAGCGCCTTTACG |
| 250 | GGCGTGACGAGGCAAAGACGAGCGCCTTTACG |
| 251 | AATAGTGTTACCCAAAGACGAGCGCCTTTACG |
| 252 | CAGAAGCTCAGGCAAAGACGAGCGCCTTTACG |
| 253 | TAGTGGCAAGAACAAAGACGAGCGCCTTTACG |
| 254 | ACAGACTCTCAACAAAGACGAGCGCCTTTACG |
| 255 | GGATGACACCTTCAAAGACGAGCGCCTTTACG |
| 256 | GTGAGCTCTCAACAAAGACGAGCGCCTTTACG |
| 257 | ACTCCGCTCAGGCAAAGACGAGCGCCTTTACG |
| 258 | ATCGTTGACCAACAAAGACGAGCGCCTTTACG |
| 259 | CAGTGCTATACCCAAAGACGAGCGCCTTTACG |
| 260 | CAGTCACGGAGGCAAAGACGAGCGCCTTTACG |
| 261 | ATACGGCATCAACAAAGACGAGCGCCTTTACG |
| 262 | TGTAAGAACGAACAAAGACGAGCGCCTTTACG |
| 263 | AGCTAGCATCTTCAAAGACGAGCGCCTTTACG |
| 264 | CCAAGTCCTCAACAAAGACGAGCGCCTTTACG |
| 265 | CAAGTCAGTCAACAAAGACGAGCGCCTTTACG |
| 266 | TGCGGCGGAAGGCAAAGACGAGCGCCTTTACG |
| 267 | CTCGCGGCAACCCAAAGACGAGCGCCTTTACG |
| 268 | TCACCTAAGACCCAAAGACGAGCGCCTTTACG |
| 269 | CCGCTAGTCCTTCAAAGACGAGCGCCTTTACG |
| 270 | AGCGGCCGGCTTCAAAGACGAGCGCCTTTACG |
| 271 | TCCGTTCGCAGGCAAAGACGAGCGCCTTTACG |
| 272 | CCGACAGCGACCCAAAGACGAGCGCCTTTACG |
| 273 | CCAACGTTGCTTCAAAGACGAGCGCCTTTACG |
| 274 | CTGAATCACGAACAAAGACGAGCGCCTTTACG |
| 275 | AGGACGTGTCTTCAAAGACGAGCGCCTTTACG |
| 276 | TAATAGCTACTTCAAAGACGAGCGCCTTTACG |
| 277 | GTAGGAAGGCTTCAAAGACGAGCGCCTTTACG |
| 278 | GTAATACAGGAACAAAGACGAGCGCCTTTACG |
| 279 | GCCGCGCTACTTCAAAGACGAGCGCCTTTACG |
| 280 | CGACTCTGACGGCAAAGACGAGCGCCTTTACG |
| 281 | CTCATGCCGCGGCAAAGACGAGCGCCTTTACG |
| 282 | TCCTGGTGTCTTCAAAGACGAGCGCCTTTACG |
| 283 | CAGCGGCCGCAACAAAGACGAGCGCCTTTACG |
| 284 | TAACGCGTACGGCAAAGACGAGCGCCTTTACG |
| 285 | CTAGGATGAAGGCAAAGACGAGCGCCTTTACG |
| 286 | GCATTCGAGACCCAAAGACGAGCGCCTTTACG |
| 287 | TATCGTAATCGGCAAAGACGAGCGCCTTTACG |
| 288 | AGTCATGTGCAACAAAGACGAGCGCCTTTACG |
| 289 | GGCGCGCATCGGCGTCCATCTCGAAGGAGTCG |
| 290 | CCTAGCTGACAACGTCCATCTCGAAGGAGTCG |
| 291 | ACACCATAGAGGCGTCCATCTCGAAGGAGTCG |
| 292 | GGTCACATGCGGCGTCCATCTCGAAGGAGTCG |
| 293 | CTACTCTTCCAACGTCCATCTCGAAGGAGTCG |
| 294 | TGCCACACACTTCGTCCATCTCGAAGGAGTCG |
| 295 | TACCTAGCTCTTCGTCCATCTCGAAGGAGTCG |
| 296 | CCTAGGTGGAGGCGTCCATCTCGAAGGAGTCG |
| 297 | GTCCTGTGGACCCGTCCATCTCGAAGGAGTCG |
| 298 | TGCGACTTCCGGCGTCCATCTCGAAGGAGTCG |
| 299 | GAGCTCCGCGTTCGTCCATCTCGAAGGAGTCG |
| 300 | TACAACCAACGGCGTCCATCTCGAAGGAGTCG |
| 301 | TGAGTCGAAGAACGTCCATCTCGAAGGAGTCG |
| 302 | GACGTGATAACCCGTCCATCTCGAAGGAGTCG |

TABLE 1-continued

| SEQ ID NO | EXEMPLARY SEQUENCE |
|---|---|
| 303 | TGGAGAGAGCTTCGTCCATCTCGAAGGAGTCG |
| 304 | GATCGCCACACCCGTCCATCTCGAAGGAGTCG |
| 305 | GTTCAGAGCAGGCGTCCATCTCGAAGGAGTCG |
| 306 | CAATGAGGCACCCGTCCATCTCGAAGGAGTCG |
| 307 | ATGGATGCCACCCGTCCATCTCGAAGGAGTCG |
| 308 | TATACGTCACTTCGTCCATCTCGAAGGAGTCG |
| 309 | CATAACGGAAGGCGTCCATCTCGAAGGAGTCG |
| 310 | ACTTCGTGGACCCGTCCATCTCGAAGGAGTCG |
| 311 | TGCTGGTCACGGCGTCCATCTCGAAGGAGTCG |
| 312 | ACGTCGATCCTTCGTCCATCTCGAAGGAGTCG |
| 313 | GCAGGTAAGAGGCGTCCATCTCGAAGGAGTCG |
| 314 | GCTCTAGGACAACGTCCATCTCGAAGGAGTCG |
| 315 | AGCGCATATCAACGTCCATCTCGAAGGAGTCG |
| 316 | ACACCTTAACAACGTCCATCTCGAAGGAGTCG |
| 317 | GATTCACTTACCCGTCCATCTCGAAGGAGTCG |
| 318 | GGTCCATAGACCCGTCCATCTCGAAGGAGTCG |
| 319 | TCTAAGATGGCCCGTCCATCTCGAAGGAGTCG |
| 320 | AATGCCGATCTTCGTCCATCTCGAAGGAGTCG |
| 321 | CCAGGATAGACCCGTCCATCTCGAAGGAGTCG |
| 322 | GTTATGTTCGAACGTCCATCTCGAAGGAGTCG |
| 323 | GGCTAGTAGGAACGTCCATCTCGAAGGAGTCG |
| 324 | GTACGATATCGGCGTCCATCTCGAAGGAGTCG |
| 325 | AACCACTTAACCCGTCCATCTCGAAGGAGTCG |
| 326 | TCCGCTATACGGCGTCCATCTCGAAGGAGTCG |
| 327 | ACTCTGAGACGGCGTCCATCTCGAAGGAGTCG |
| 328 | GCGTCGGTAGAACGTCCATCTCGAAGGAGTCG |
| 329 | ATATGGTCACTTCGTCCATCTCGAAGGAGTCG |
| 330 | TTAATTAATCAACGTCCATCTCGAAGGAGTCG |
| 331 | AAGTTGCTCACCCGTCCATCTCGAAGGAGTCG |
| 332 | GGTTATGGAGAACGTCCATCTCGAAGGAGTCG |
| 333 | TAGACGAATACCCGTCCATCTCGAAGGAGTCG |
| 334 | TCTACATAAGAACGTCCATCTCGAAGGAGTCG |
| 335 | CAGAACCTTCAACGTCCATCTCGAAGGAGTCG |
| 336 | CAAGGCTCAGAACGTCCATCTCGAAGGAGTCG |
| 337 | GACTCCACCACCCGTCCATCTCGAAGGAGTCG |
| 338 | AACCGTGGAGAACGTCCATCTCGAAGGAGTCG |
| 339 | GGTCCTTAACTTCGTCCATCTCGAAGGAGTCG |
| 340 | CGCCACGCCGAACGTCCATCTCGAAGGAGTCG |
| 341 | ACTTATACGCGGCGTCCATCTCGAAGGAGTCG |

TABLE 1-continued

| SEQ ID NO | EXEMPLARY SEQUENCE |
|---|---|
| 342 | CTCCTCAGGAGGCGTCCATCTCGAAGGAGTCG |
| 343 | GTGAGGTCCAGGCGTCCATCTCGAAGGAGTCG |
| 344 | CACATGCGCCTTCGTCCATCTCGAAGGAGTCG |
| 345 | GTGCACTTAAGGCGTCCATCTCGAAGGAGTCG |
| 346 | GGCGTGACGAGGCGTCCATCTCGAAGGAGTCG |
| 347 | AATAGTGTTACCCGTCCATCTCGAAGGAGTCG |
| 348 | CAGAAGCTCAGGCGTCCATCTCGAAGGAGTCG |
| 349 | TAGTGGCAAGAACGTCCATCTCGAAGGAGTCG |
| 350 | ACAGACTCTCAACGTCCATCTCGAAGGAGTCG |
| 351 | GGATGACACCTTCGTCCATCTCGAAGGAGTCG |
| 352 | GTGAGCTCTCAACGTCCATCTCGAAGGAGTCG |
| 353 | ACTCCGCTCAGGCGTCCATCTCGAAGGAGTCG |
| 354 | ATCGTTGACCAACGTCCATCTCGAAGGAGTCG |
| 355 | CAGTGCTATACCCGTCCATCTCGAAGGAGTCG |
| 356 | CAGTCACGGAGGCGTCCATCTCGAAGGAGTCG |
| 357 | ATACGGCATCAACGTCCATCTCGAAGGAGTCG |
| 358 | TGTAAGAACGAACGTCCATCTCGAAGGAGTCG |
| 359 | AGCTAGCATCTTCGTCCATCTCGAAGGAGTCG |
| 360 | CCAAGTCCTCAACGTCCATCTCGAAGGAGTCG |
| 361 | CAAGTCAGTCAACGTCCATCTCGAAGGAGTCG |
| 362 | TGCGGCGGAAGGCGTCCATCTCGAAGGAGTCG |
| 363 | CTCGCGGCAACCCGTCCATCTCGAAGGAGTCG |
| 364 | TCACCTAAGACCCGTCCATCTCGAAGGAGTCG |
| 365 | CCGCTAGTCCTTCGTCCATCTCGAAGGAGTCG |
| 366 | AGCGGCCGGCTTCGTCCATCTCGAAGGAGTCG |
| 367 | TCCGTTCGCAGGCGTCCATCTCGAAGGAGTCG |
| 368 | CCGACAGCGACCCGTCCATCTCGAAGGAGTCG |
| 369 | CCAACGTTGCTTCGTCCATCTCGAAGGAGTCG |
| 370 | CTGAATCACGAACGTCCATCTCGAAGGAGTCG |
| 371 | AGGACGTGTCTTCGTCCATCTCGAAGGAGTCG |
| 372 | TAATAGCTACTTCGTCCATCTCGAAGGAGTCG |
| 373 | GTAGGAAGGCTTCGTCCATCTCGAAGGAGTCG |
| 374 | GTAATACAGGAACGTCCATCTCGAAGGAGTCG |
| 375 | GCCGCGCTACTTCGTCCATCTCGAAGGAGTCG |
| 376 | CGACTCTGACGGCGTCCATCTCGAAGGAGTCG |
| 377 | CTCATGCCGCGGCGTCCATCTCGAAGGAGTCG |
| 378 | TCCTGGTGTCTTCGTCCATCTCGAAGGAGTCG |
| 379 | CAGCGGCCGCAACGTCCATCTCGAAGGAGTCG |
| 380 | TAACGCGTACGGCGTCCATCTCGAAGGAGTCG |

TABLE 1-continued

| SEQ ID NO | EXEMPLARY SEQUENCE |
|---|---|
| 381 | CTAGGATGAAGGCGTCCATCTCGAAGGAGTCG |
| 382 | GCATTCGAGACCCGTCCATCTCGAAGGAGTCG |
| 383 | TATCGTAATCGGCGTCCATCTCGAAGGAGTCG |
| 384 | AGTCATGTGCAACGTCCATCTCGAAGGAGTCG |

Adapters

In some embodiments, the methods and kits described herein comprise adapters. In some embodiments, adapters are single-stranded or double-stranded oligonucleotides that can be ligated to the ends of DNA or RNA molecules. In some embodiments, adapters have blunt ends. In some embodiments, adapters have sticky ends. In some embodiments, adapters have one blunt end and one sticky end. In some embodiments, an adapter can be used to link the ends of two other nucleotide sequences. In some embodiments, an adapter can ligate nucleotide sequences into a plasmid. In some embodiments, an adapter can bind or be ligated to nucleotide fragments of unknown sequence. In some embodiments, adapters comprise a primer binding site. In some embodiments, adapters comprise a barcode. In some embodiments, adapters comprise a primer binding site and a barcode. In some embodiments, an adapter may be a universal adapter. In some embodiments, a universal adapter comprises a universal primer binding site and optionally a barcode.

Barcodes

As used herein, the term "barcode" refers to a label, or identifier, that conveys or is capable of conveying information about a sample. A barcode can be part of a sample. A barcode can be independent of a sample. A barcode can be a tag attached to a sample or a combination of the tag in addition to an endogenous characteristic of the sample (e.g., size of the sample or end sequence(s)). A barcode can be unique. Barcodes can have a variety of different formats. For example, barcodes can include polynucleotide barcodes, random nucleic acid, and/or synthetic nucleic acid sequences. A barcode can be attached to a sample in a reversible or irreversible manner. A barcode can be added to a fragment of a deoxyribonucleic acid (DNA) or ribonucleic acid (RNA) sample before, during, and/or after sequencing of the sample. Barcodes can allow for identification and/or quantification of individual sequencing-reads.

In some embodiments, an adapter comprises a barcode. In some embodiments, the barcode is attached to a primer binding site. A barcode sequence in a nucleic acid sequence can enable association of the biological sample from which the barcoded nucleic acid sequence was derived. For example, a barcode sequence in a nucleic acid sequence can enable the identification of the sample associated with the barcode.

Barcode sequences can include from about 6 to about 20 or more nucleotides within the sequence of the adapters. In some cases, the length of a barcode sequence can be about 6, 7, 8, 9, 10, 11, 12, 13, 14, 15, 16, 17, 18, 19, 20 nucleotides, or longer. In some cases, the length of a barcode sequence can be at least about 6, 7, 8, 9, 10, 11, 12, 13, 14, 15, 16, 17, 18, 19, 20 nucleotides, or longer. In some cases, the length of a barcode sequence can be at most about 6, 7, 8, 9, 10, 11, 12, 13, 14, 15, 16, 17, 18, 19, 20 nucleotides, or shorter.

In some embodiments, a barcode sequence is associated with a particular partition. In some embodiments, a barcode sequence is associated with a particular spike in control. In some embodiments, a barcode sequence associated with a particular partition is the same as another barcode sequence associated with a different partition. In some embodiments, a barcode sequence associated with a particular partition is different from every other barcode sequence and every other partition associated with a particular run, experiment, or sample set. In some embodiments, an adapter comprises more than one barcode binding site. In some embodiments, each barcode in a set is unique. For example, any two barcodes chosen out of a given set will differ in at least one nucleotide position. In some embodiments, a set includes at least one unique barcode for each sample desired to be processed in parallel. For example, if in a given instance it is desired to process 8, 16, 48, 96, 384, or more samples in parallel, then the corresponding set of barcodes will include at least 8, 16, 48, 96, 384, or more barcodes.

In some embodiments, the barcode is a nucleic acid sequence that does not substantially hybridize to analyte nucleic acid molecules in a sample. In some embodiments, complementarity is eliminated just to sequences expressed in particular cells, tissues, or organs of a sample. In some embodiments, the barcode has less than 80% sequence identity to the nucleic acid sequences in the sample. In some embodiments, the barcode has less than 70%, 60%, 50% or less than 40% sequence identity across a substantial part of the nucleic acids molecules in the sample. Sequence identity may be determined by any appropriate method known in the art, e.g. the using BLAST alignment algorithm.

Universal Primers

In some embodiments, the adapter comprises one or more universal primer binding sites. In some embodiments, universal primers anneal to many different types of nucleotide templates. In some embodiments, universal primers are related to nucleotide sequences that are commonly found in cloning vectors and DNA molecules, for example the 16S Ribosomal RNA region. In some embodiments, the one or more universal primer is used as an adapter sequence. In some embodiments, universal primers anneal to a denatured nucleotide template to provide an initiation site for the elongation of a new DNA molecule. In some embodiments, a primer set can contain one or more specific primers and one or more universal primers. In some embodiments, a primer set can contain two or more universal primers. In some embodiments, a primer set contains a specific forward primer and a universal reverse primer. In some embodiments, a primer set contains a universal forward primer and a specific reverse primer. In some embodiments, a primer set contains a universal forward primer and a universal reverse primer. In some embodiments, a universal primers are used in rolling circle amplification. In some embodiments, one or more universal primers may be used when amplification calls for one or more primers. In some embodiments, one or more universal primers are used to amplify the spike in controls. In some embodiments, one or more universal primers are used to amplify the sample fragments. In some embodiments, one or more universal primers are used to amplify the spike in controls and sample fragments.

Tag Tagging

As used herein, the term "tag" or "tagged" generally refers to a molecule capable of binding to a macromolecular constituent. The tag can bind to the macromolecular constituent with high affinity. The tag can bind to the macromolecular constituent with high specificity. The tag can comprise a nucleotide sequence. The tag can comprise a nucleic acid sequence. The nucleic acid sequence can be at least a portion or an entirety of the tag. The tag can be a nucleic acid molecule or can be part of a nucleic acid molecule. The tag can be an oligonucleotide or a polypeptide. The tag can be or comprise a primer. The tag can be a barcode.

PCR Amplification and Sequencing

An adapter or universal adapter can attach to the nucleic acid fragments by annealing, extension and amplification reaction, and/or ligation reactions. Extension and amplification reagents include DNA polymerase, nucleoside triphosphates, and buffers with co-factors (e.g. $Mg^{2+}$). The adapter can be attached at either one or both ends of the nucleic acid fragment to yield a barcoded nucleic acid fragment.

In some embodiments, captured genetic material is amplified. In some embodiments, the captured genetic material is amplified via PCR. The polymerase chain reaction (PCR) is well known in the art (described in U.S. Pat. Nos. 4,683,202; 4,683,195; 4,800,159; 4,965,188 and 5,512,462, the disclosures of which are herein incorporated by reference). In representative PCR amplification reactions, the reaction mixture includes the sample, an enzyme, one or more primers that are employed in the primer extension reaction, and reagents for the reaction. The oligonucleotide primers are of sufficient length to provide for hybridization to complementary template sample under annealing conditions. The length of the primers will depend on the length of the amplification domains, but will generally be at least 10 base pairs (bp), at least 11 bp, at least 12 bp, at least 13 bp, at least 14 bp, at least 15 bp, at least 16 bp, at least 17 bp, at least 18 bp, at least 19 bp, at least 20 bp, at least 25 bp, at least 30 bp, at least 35 bp, and may be as long as 40 bp or longer, where the length of the primers will generally range from 18 to 50 bp. In some cases, the primers are from about 20 to 35 bp. The template genetic material may be contacted with a single primer or a set of two primers (forward and reverse primers), depending on whether primer extension, linear or exponential amplification of the template sample is desired.

In some embodiments, the PCR amplification comprises the use of a DNA polymerase enzyme. The DNA polymerase activity may be provided by one or more distinct DNA polymerase enzymes. In some embodiments, the DNA polymerase enzyme is from a bacterium, e.g., the DNA polymerase enzyme is a bacterial DNA polymerase enzyme. For instance, the DNA polymerase may be from a bacterium of the genus *Escherichia, Bacillus, Thermophilus* or *Pyrococcus*.

Suitable non-limiting examples of DNA polymerases that can be used in accordance with materials and methods disclosed herein include: *E. coli* DNA polymerase I, Bsu DNA polymerase, Bst DNA polymerase, Taq DNA polymerase, VENT™ DNA polymerase, DEEPVENT™ DNA polymerase, LongAmp® Taq DNA polymerase, LongAmp® Hot Start Taq DNA polymerase, Crimson LongAmp® Taq DNA polymerase, Crimson Taq DNA polymerase, OneTaq® DNA polymerase, OneTaq® Quick-Load® DNA polymerase, Hemo KlenTaq® DNA polymerase, REDTaq® DNA polymerase, Phusion® DNA polymerase, Phusion® High-Fidelity DNA polymerase, Platinum Pfx DNA polymerase, Accuprime™ Pfx DNA polymerase, Phi29 DNA polymerase, Klenow fragment, Pwo DNA polymerase, Pfu DNA polymerase, T4 DNA polymerase and T7 DNA polymerase enzymes. As used herein, the term "DNA polymerase" includes not only naturally occurring enzymes but also all such modified derivatives, including also derivatives of naturally occurring DNA polymerase enzymes. For instance, in some embodiments, the DNA polymerase may have been modified to remove 5'-3' exonuclease activity.

Sequence-modified derivatives or mutants of DNA polymerase enzymes include, without limitation, mutants that retain at least some of the functional, e.g. DNA polymerase activity of the wild-type sequence. Mutations may affect the activity profile of the enzymes, e.g. enhance or reduce the rate of polymerization, under different reaction conditions, e.g. temperature, template concentration, primer concentration etc. Mutations or sequence-modifications may also affect the exonuclease activity and/or thermostability of the enzyme.

In some embodiments, the amplifying includes use of one or more amplifying techniques of a polymerase chain reaction (PCR), a strand-displacement amplification reaction, a rolling circle amplification reaction, a ligase chain reaction, a transcription-mediated amplification reaction, and/or a loop-mediated amplification reaction. In some embodiments, the amplifying includes a PCR using a single primer that is complementary to the 3' tag of target sample fragments. In some embodiments, the amplifying includes PCR using a first and a second primer, wherein at least a 3' end portion of the first primer is complementary to at least a portion of the 3' tag of the target sample fragments, and wherein at least a 3' end portion of the second primer exhibits the sequence of at least a portion of the 5' tag of the target sample fragments. In some embodiments, a 5' end portion of the first primer is non-complementary to the 3' tag of the target nucleic acid fragments, and a 5' end portion of the second primer does not exhibit the sequence of at least a portion of the 5' tag of the target sample fragments. In some embodiments, the first primer includes a first universal sequence, and/or wherein the second primer includes a second universal sequence. In some embodiments, the method further includes sequencing tagged sample fragments. In some embodiments, the sequencing of the sample includes use of one or more of sequencing by synthesis, bridge PCR, chain termination sequencing, sequencing by hybridization, nanopore sequencing, and sequencing by ligation.

In some embodiments (e.g., when the method is used to capture DNA), the amplification reaction comprises the use of a DNA ligase enzyme. The DNA ligase activity may be provided by one or more distinct DNA ligase enzymes. In some embodiments, the DNA ligase enzyme is from a bacterium, e.g., the DNA ligase enzyme is a bacterial DNA ligase enzyme. For instance, the DNA ligase may be T4 DNA ligase. Other enzymes appropriate for the ligation step are known in the art and include, without limitation, Tth DNA ligase, Taq DNA ligase, *Thermococcus* sp. (strain 9° N) DNA ligase (9°™ N DNA ligase, New England Biolabs), and Ampligase™ (Epicentre Biotechnologies). Derivatives, e.g. sequence-modified derivatives, or mutants thereof, may also find utility in the methods provided herein.

In some embodiments, the captured genetic material is amplified by reverse transcription polymerase chain reaction (RT-PCR). The desired reverse transcriptase activity may be provided by one or more distinct reverse transcriptase enzymes, wherein suitable examples are: M-MLV, MuLV, AMV, HIV, ArrayScript™, MultiScribe™, ThermoScript™ and SuperScript® I, II, III, and IV enzymes. As used herein, the term "reverse transcriptase" includes not only naturally occurring enzymes, but also all such modified derivatives including derivatives of naturally occurring reverse transcriptase enzymes.

Sequence-modified derivatives or mutants of M-MLV, MuLV, AMV and HIV reverse transcriptase enzymes include mutants that retain at least some of the functional, e.g. reverse transcriptase, activity of the wild-type sequence. Mutations may affect the activity profile of the enzymes, e.g. enhance or reduce the rate of polymerisation, under different reaction conditions, e.g. temperature, template concentration, primer concentration etc. Mutations or sequence-modifications may also affect the RNase activity and/or thermostability of the enzyme. The reverse transcriptase enzyme may be provided as part of a composition which comprises other components, e.g. stabilizing components, that enhance or improve the activity of the reverse transcriptase enzyme, such as RNase inhibitor(s), inhibitors of DNA-dependent DNA synthesis, e.g. actinomycin D. Many sequence-modified derivative or mutants of reverse transcriptase enzymes, e.g. M-MLV, and compositions comprising unmodified and modified enzymes are known in the art and are commercially available, e.g. ArrayScript™ MultiScribe™, ThermoScript™, and SuperScript® I, II, III and IV enzymes, and all such enzymes are considered to be useful in the methods of the invention.

It is established in the art that some reverse transcriptase enzymes (e.g. Avian Myeloblastosis Virus (AMV) Reverse Transcriptase and Moloney Murine Leukemia Virus (M-MuLV, MMLV) Reverse Transcriptase) can synthesize a complementary DNA strand using both RNA (cDNA synthesis) and single-stranded DNA (ssDNA) as a template. Thus, in some embodiments, the extension reaction may utilize an enzyme (reverse transcriptase) that is capable of using both RNA and ssDNA as the template for an extension reaction, e.g. an AMV or MMLV reverse transcriptase.

In some embodiments, the quantification of RNA and/or DNA is carried out by real time PCR (also known as quantitative PCR or qPCR), using techniques well known in the art, such as but not limited to "TAQMAN™" or "SYBR®", or on capillaries ("LightCycler® Capillaries"). Additional real time PCR techniques or methods are known in the art, and a person of ordinary skill in the art will be able to utilize them in accordance with the materials and methods provided herein. In some embodiments, the quantification of genetic material is determined by optical absorbance and with real time PCR. In some embodiments, the quantification of genetic material is determined by digital PCR. In some embodiments, the genes analyzed may be compared to a reference nucleic acid extract (DNA and RNA) corresponding to the expression (mRNA) and quantity (DNA) in order to compare expression levels of the target nucleic acids.

The term "sequencing," generally refers to methods and technologies for determining the sequence of nucleotide bases in one or more polynucleotides. The polynucleotides can be, for example, nucleic acid molecules such as deoxyribonucleic acid (DNA) or ribonucleic acid (RNA), including variants or derivatives thereof (e.g., single stranded DNA or ssDNA). Sequencing can be performed by any of a variety of various systems currently available, such as, without limitation, a sequencing system by Illumina®, Roche®, Pacific Biosciences (PacBio®), Oxford Nanopore®, or Life Technologies (Ion Torrent®). Alternatively or in addition, sequencing may be performed using nucleic acid amplification, polymerase chain reaction (PCR) (e.g., digital PCR, quantitative PCR, or real time PCR), or isothermal amplification. Such systems may provide a plurality of raw genetic data corresponding to the genetic information of a subject (e.g., human), as generated by the systems from a sample provided by the subject. In some examples, such systems provide sequencing reads (also "reads" herein). A read may include a string of nucleic acid bases corresponding to a sequence of a nucleic acid molecule that has been sequenced. In some situations, systems and methods provided herein may be used with proteomic information.

Any appropriate method can be used to sequence the sample. Non-limiting examples of methods for sequencing samples include PCR-based sequencing (such as multiplex PCR-based sequencing), DNA hybridization methods (e.g., Southern blotting), restriction enzyme digestion methods, PCR-based multiplex methods, digital PCR methods, droplet digital PCR (ddPCR) methods, PCR-based singleplex PCR methods, Sanger sequencing methods, next-generation sequencing methods (e.g., single-molecule real-time sequencing, nanopore sequencing, and Polony sequencing), quantitative PCR methods, ligation methods, and microarray methods. Further non-limiting examples of sequencing methods include targeted sequencing, single molecule real-time sequencing, exon sequencing, electron microscopy-based sequencing, panel sequencing, transistor-mediated sequencing, direct sequencing, random shotgun sequencing, Sanger dideoxy termination sequencing, whole-genome sequencing, sequencing by hybridization, pyrosequencing, capillary electrophoresis, gel electrophoresis, duplex sequencing, cycle sequencing, single-base extension sequencing, solid-phase sequencing, high-throughput sequencing, massively parallel signature sequencing, emulsion PCR, co-amplification at lower denaturation temperature-PCR (COLD-PCR), multiplex PCR, sequencing by reversible dye terminator, paired-end sequencing, near-term sequencing, exonuclease sequencing, sequencing by ligation, short-read sequencing, single-molecule sequencing, sequencing-by-synthesis, real-time sequencing, reverse-terminator sequencing, nanopore sequencing, 454 sequencing, Solexa Genome Analyzer sequencing, SOLiD™ sequencing, MS-PET sequencing, and any combinations thereof.

Sequence analysis of fragmented sample (including barcoded sample fragments or derivatives thereof) may be direct or indirect. Thus, the sequence analysis substrate (which may be viewed as the sample which is subjected to the sequence analysis step or process) may directly be a barcoded sample or it may be a sample which is derived therefrom. Thus, in the context of sequence analysis, the sequencing template may be the barcoded sample fragment or it may be a segment derived therefrom. For example, a first and/or second strand DNA molecule may be directly subjected to sequence analysis (e.g. sequencing), i.e. may directly take part in the sequence analysis reaction or process (e.g. the sequencing reaction or sequencing process, or be the sample which is sequenced or otherwise identified). Alternatively, the barcoded sample fragment may be subjected to a step of second strand synthesis or amplification before sequence analysis (e.g. sequencing or identification by other means). The sequence analysis substrate (e.g. template) may thus be an amplicon or a second strand of a barcoded sample fragment.

In some embodiments, sequence analysis comprises deep sequencing. Deep sequencing refers to aiming for a high number of unique reads of each region or fragment of a sequence. Deep sequencing of nucleotide fragments can be used to generate sample libraries with fewer sequencing errors.

Sequencing of barcoded sample fragments can provide sequencing reads comprising nucleic acid sequences. Such nucleic acid sequences can comprise the barcode sequences of the barcoded sample fragments, or complements thereof. For example, a plurality of sequencing reads corresponding to a given partition can be generated, in which a subset of the plurality of sequencing reads comprises the barcode sequence of the barcoded nucleic acid molecule or a complement thereof. The nucleic acid sequence can comprise a sequence corresponding to the barcodes in a partition and/or a sequence corresponding to the sample fragment in a partition.

In some embodiments, both strands of a double stranded molecule may be subjected to sequence analysis (e.g. sequenced). In some embodiments, single stranded samples (e.g. barcoded samples) may be analysed (e.g. sequenced). For example, various sequencing technologies may be used for single molecule sequencing, e.g. the Helicos or Pacbio technologies, or nanopore sequencing technologies which are in development. In some embodiments the barcoded sample fragment, e.g., the first strand of DNA, may be subjected to sequencing. The first strand DNA can be modified at the 3' end to enable single molecule sequencing. This may be done by procedures analogous to those for handling the second DNA strand. Such procedures are known in the art.

It will be apparent that any nucleic acid sequencing method may be utilised in accordance with materials and methods provided herein. In some embodiments, so-called "next generation sequencing" techniques may be used. Next generation sequencing generally employs high-throughput sequencing, enabling a large number of nucleic acids to be partially sequenced in a very short period of time. In some embodiments, the full-length of the barcoded sample fragment is sequenced.

As a representative example, the sequencing reaction may be based on reversible dye-terminators, such as used in the Illumina™ technology. For example, DNA molecules are first attached to primers on, e.g. a glass or silicon slide and amplified so that local clonal colonies are formed (bridge amplification). Four types of ddNTPs are added, and non-incorporated nucleotides are washed away. Unlike pyrosequencing, the DNA is only extended one nucleotide at a time. A camera takes images of the fluorescently labelled nucleotides then the dye along with the terminal 3' blocker is chemically removed from the DNA, allowing a next cycle. This may be repeated until the required sequence data is obtained. Using this technology, thousands of nucleic acids may be sequenced simultaneously on a single slide.

Other high-throughput sequencing techniques can also be used in accordance with materials and methods provided herein, e.g. pyrosequencing. In this method the DNA is amplified inside water droplets in an oil solution (emulsion PCR), with each droplet containing a single DNA template attached to a single primer-coated bead that then forms a clonal colony. The sequencing machine contains many picolitre-volume wells each containing a single bead and sequencing enzymes. Pyrosequencing uses luciferase to generate light for detection of the individual nucleotides added to the nascent DNA and the combined data are used to generate sequence read-outs.

In some embodiments, sequencing is performed by detection of hydrogen ions that are released during the polymerisation of DNA. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogen ions and a proportionally higher electronic signal.

A person of ordinary skill in the art will be aware of other sequencing technologies will be useful in accordance with materials and methods provided herein.

Methods

In some embodiments, methods for detecting a contaminated or misidentified sample comprises amplifying at least one nucleic acid fragment, for example a control nucleotide or a nucleic acid fragment. The skilled artisan will understand that a wide variety of nucleic acid amplification techniques known in the art in the art may be employed in the current teachings. Exemplary nucleic acid amplification techniques include reverse transcription (RT), polymerase chain reaction (PCR), real time or quantitative PCR (Q-PCR), and reverse transcription coupled with PCR (RT-PCR).

In some embodiments, each sample is initially combined with a known concentration of a unique spike-in control or a unique set of spike-in controls, and a primer set comprising a unique barcode or the complement of the barcode. The spike-in controls and primer set for each sample are unique in that the set of spike-in controls and the primer set comprising the barcode or its complement are used only once in that reaction and thus they correspond to only one sample. Thus, the presence of barcode or spike-in sequences in the output that do not correspond to the sample they correspond to indicates that the sample has been contaminated or misidentified.

In some embodiments, sample contamination is detected by analyzing the sequencing data generated from each initial sample. The detection and/or data analysis may be done manually or it may be part of an automated process. For example, predetermined rejection parameters may be programmed into an instrument that is used to analyze the sample data. The instrument would reject as contaminated any sample data that does not meet the parameters for inclusion.

In some embodiments, any number of samples are processed in parallel using the methods described herein. For example, four samples are processed in parallel to prepare four sequencing libraries which will be deep sequenced. Each of the four samples, are combined with a unique spike-in control and a primer set comprising a unique barcode or its complement. For example, reaction 1 comprises sample 1, spike-in control 1 (SIC 1), and Barcode 1 (the primer set that corresponds to and subsequently incorporates barcode 1 in the Sample 1 fragments during library preparation). Likewise, Reaction 2 comprises Sample 2, SIC 2, and Barcode 2 (the primer set that corresponds to and subsequently incorporates barcode 2 in the Sample 2 fragments during library preparation); and so forth. After the four reaction compositions are prepared, they are subjected to various library prep process steps. In some embodiments, one or more SICs and one or more barcodes are amplified in the reaction composition/partition associated with those particular SICs and/or barcodes. In some embodiments, one or more SICs or one or more barcodes are amplified in a partition that is not the reaction composition or partition with which the SIC or barcode is associated. For example, Reaction 2 has become contaminated with reaction material from the Reaction 3 composition during the process, so that the vessel containing Library 2 includes not only Sample 2 fragments comprising Barcode 2 and SIC 2, but also Sample 3 fragments comprising Barcode 3 and SIC 3 (see FIG. 1).

In some embodiments, the nucleic acid concentration of a sample is determined. Based on the nucleic acid concentration, a unique SIC and an adapter are combined with the sample in any order to form a reaction composition. The sample nucleic acid is fragmented, for example, by sonic fragmentation (e.g., Covaris® fragmentation) or enzymatically fragmented according to known methods. In some embodiments, fragments comprising single-stranded overhangs are converted to blunt end fragments that are also 5' phosphorylated and 3' adenylated. In the presence of a suitable ligase and under appropriate conditions, adapters are ligated to blunt-ended fragments. In certain embodiments, the adapters comprise a unique barcode sequence, a primer binding site, and may comprise other sequences that may be useful for, among other things, tagging or identifying fragments comprising the adapter. In such embodiments, when the adapter is ligated to the sample fragment, the ligation product comprises a barcode sequence. Thus, all fragments in the reaction composition will be barcoded when ligated to the adapter.

In other embodiments, a universal adapter lacking a barcode sequence is added to the reaction composition. Fragments that have been ligated to a universal adapter may be barcoded using a primer set comprising a barcode sequence or its complement which becomes incorporated in the amplification products obtained from that primer set. For library sequencing, the initial concentration of SIC employed with a particular sample depends on the nucleic acid concentration of the sample and the number of sequencing reads necessary to obtain the desired sample sequence information. The initial SIC concentration should be small enough that the majority of the sequencing reads correspond to sample fragments, but also large enough that a sufficient number of SIC sequence reads are detectable. In certain embodiments, SIC concentrations about 1% wt/wt of the sample may be appropriate. In some embodiments, the SIC concentration is 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% wt/wt of the sample. In some embodiments, the SIC concentration is between 0.1% and 2.0%, 0.2% and 1.9%, 0.3% and 1.8%, 0.4% and 1.7%, 0.5% and 1.6%, 0.6% and 1.5%, 0.7% and 1.4%, 0.8% and 1.3%, 0.9% and 1.2% wt/wt of the sample.

Kits

In some embodiments, kits are provided to expedite the performance of various disclosed methods. In some embodiments, kits for detecting a contaminated or misidentified sample comprise a multiplicity of spike-in controls and a multiplicity of adapters. In some embodiments, each adapter comprises a barcode sequence and a primer binding site. In some embodiments, the adapters do not comprise a barcode sequence. In some embodiments, kits comprise adapters that comprise a barcode sequence and universal adapters that do not comprise a barcode sequence. In some embodiments, kits further comprise at least one ligase, at least one polymerase, or combinations thereof. In some embodiments, the kits comprise the spike in control primers provided herein. Kits serve to expedite the performance of certain method embodiments by assembling two or more reagents and/or components used in carrying out certain methods. Kits may contain reagents in pre-measured unit amounts to minimize the need for measurements by end-users. Kits may also include instructions for performing one or more of the disclosed methods. In certain embodiments, at least some of the kit components are optimized to perform in conjunction with each other. Typically, kit reagents may be provided in solid, liquid, or gel form.

EXAMPLES

Example 1. Spike in Control Protocol for Detection of Contamination or Misidentification The following protocol is one embodiment of the methods described herein. The skilled artisan would understand that modifications to the protocol can be made within the scope of the disclosure.

Spike in controls of known size and sequence are added to quantitatively purified genomic DNA samples. The spike in control is generally added at 1% wt/wt of the purified genomic DNA. One spike in control is used per sample, and the spike in controls should be discarded after use to avoid contamination of the controls.

The genomic DNA samples containing the spike-in controls are fragmented. The DNA fragmentation should produce nucleotide fragments around a desired median size having heterogeneous ends. The fragmentation can be an enzymatic fragmentation or ultrasonic fragmentation, such as with a Covaris® focused-ultrasonicator system.

The sheared DNA can be combined with the components of a commercial kit to achieve blunting of fragmented DNA. The 3' ends are then adenylated to prevent the nucleotide fragments from ligating to one another during the adapter ligation reaction. Adapters can then be ligated to the adenylated nucleotide fragments. The ligation products can then be purified to remove any adapters that may have ligated to one another. Purification of ligation products can also be used to select a size-range for library sequencing.

Additional sequences can be added by primers during amplification. During amplification, PCR primers are used to enrich those DNA fragments that have adapter molecules on both ends. The final product can be purified. The final product should contain a unique spike-in control as well as a unique barcoded adapter to be used to identify samples when multiplexing. As a quality control measure, an aliquot of the library can be run on an Agilent Bioanalyzer. The Bioanalyzer can be used to identify spike in control fragments, and determine whether spike in controls from another sample contaminated the target sample.

Example 2. Construction of Exemplary Sequencing Libraries Comprising Unique Spike-In Controls Starting Material. Twenty four reaction compositions were set up comprising 100 ng of *E. coli* genomic DNA and 1% of a unique SIC for each of the 24 gDNA samples (#1-24). The samples were then intentionally cross contaminated as follows: 0% Contamination—#1-3, 13-15; 0.1% Contamination—#4 & 16, 5 & 17, 6 & 18; 1% Contamination—#7 and 19, 8 and 20, 9 and 21; and 10% Contamination—#10 and 22, 11 and 23, 12 and 24. All of the reaction compositions were fragmented using either a Covaris® fragmentation protocol (Covaris®) or the NEXTFLEX™ Enzymatic DNA Fragmentation Kit protocol (Bioo Scientific Corporation, Cat. #520999, Austin, TX). Covaris® fragmented samples were contaminated only with enzymatically fragmented samples and vice versa to avoid mistaking intentional contamination with accidental contamination. Reactions comprising Covaris® and enzymatically fragmented samples were prepared in separate plates throughout entire protocol.

DNA Fragmentation. Twelve samples, each comprising one of SICs #1-12, were fragmented by the Covaris® method, following the 50 µl 400 bp shear protocol. 32 µl of sheared sample was used as input for the Rapid library prep.

An additional twelve samples, each comprising one of PHiX SICs #13-24, were fragmented according to the NEXTFLEX™ Enzymatic DNA Fragmentation Kit Protocol. All 20 μl was used as input for the Rapid DNA Library Prep protocol.

Library Prep. The Rapid DNA Library Prep protocol was followed using 8 nt barcoded adapters diluted to 3 μM, and 7 cycles of PCR were performed. All libraries were visualized on an Agilent Bioanalyzer. Libraries were then pooled equimolarly for sequencing on the MiSeq Sequencing System (Illumina Corporation, San Diego, CA).

As shown in FIG. 2, when samples comprising SIC sets (each comprising 200 bp, 400 bp and 600 bp control fragments) were analyzed using an Agilent Bioanalyzer Instrument (Agilent Technologies, Santa Clara, CA), peaks corresponding to 200 bp fragments (arrow A), 400 bp fragments (arrow B) and 600 bp fragments (arrow C) were detected.

As shown in FIG. 3, when the samples were sheared as described, the Bioanalyzer profile of the sheared material also had detectable peaks corresponding to 200 bp fragments (arrow A), 400 bp fragments (arrow B) and 600 bp fragments (arrow C).

As shown in FIG. 4, when the sheared samples were used to prepare DNA libraries as described, the Bioanalyzer profile had detectable peaks corresponding to about 320 bp fragments (arrow A'), 520 bp fragments (arrow B') and about 720 bp fragments (arrow C'). Increased fragment sizes are when 200, 400, and 600 bp fragments are processed in the library protocol described above.

What is claimed is:

1. A method for determining a nucleic acid contamination in a sample, the method comprising:

forming a reaction composition in a partition, the reaction composition comprising:
at least one unique combination of a spike in control and corresponding at least one spike in control primer, the at least one spike in control primer comprising a synthetic, unique nucleotide barcode,
at least one nucleic acid adapter, and
the sample, the sample comprising a plurality of sample nucleic acids;

fragmenting the plurality of sample nucleic acids to generate sample nucleic acid fragments;

ligating the at least one nucleic acid adapter to the sample nucleic acid fragments to generate ligation products;

amplifying the reaction composition using the at least one spike in control primer to generate a multiplicity of amplification products comprising a multiplicity of ligation product amplicons and a multiplicity of spike in control amplicons, each spike in control amplicon comprising a nucleotide tag that is unique to the spike in control amplicons generated using the corresponding at least one spike in control primer;

sequencing the multiplicity of ligation product amplicons and the multiplicity of spike in control amplicons to generate sequencing data;

detecting nucleic acid contamination in the sample, the contamination comprising an amplified spike in control not associated with the reaction composition, if the sequencing data exceeds a predetermined rejection parameter value indicative of one or more contaminating nucleic acids; and rejecting the sample if nucleic acid contamination in the sample is determined, wherein a concentration of the at least one spike in control in the reaction composition is between 0.1% to 2.0% (weight/weight %) of the plurality of sample nucleic acids in the reaction composition.

2. The method of claim 1, wherein the reaction composition comprises at least two different spike in controls and at least two different nucleic acid adapters.

3. The method of claim 1, wherein the nucleic acid adapter comprises at least one of a primer binding site and a barcode.

4. The method of claim 1, wherein the nucleic acid adapter comprises both a primer binding site and a barcode.

5. A method for improving library sequencing quality in a sample, the method comprising:

forming a reaction composition in a partition, the reaction composition comprising:
  at least one unique combination of a spike in control and corresponding at least one spike in control primer, the at least one spike in control primer comprising a synthetic, unique nucleotide barcode,
  at least one nucleic acid adapter, and
  the sample, the sample comprising a plurality of sample nucleic acids;
fragmenting the plurality of sample nucleic acids to generate sample nucleic acid fragments;
ligating the at least one nucleic acid adapter to the sample nucleic acid fragments to generate ligation products;
amplifying the reaction composition using the at least one spike in control primer to generate a multiplicity of amplification products comprising a multiplicity of ligation product amplicons and a multiplicity of spike in control amplicons, each spike in control amplicon comprising a nucleotide tag that is unique to the spike in control amplicons generated using the corresponding at least one spike in control primer;
quantifying the ligation product amplicons and the spike in control amplicons for sequencing;
detecting nucleic acid contamination in the sample, the contamination comprising an amplified spike in control not associated with the reaction composition, if the sequencing data exceeds a predetermined rejection parameter value indicative of one or more contaminating nucleic acids; and
excluding contaminated library fragment products from sequencing, wherein contaminated library fragment products include an amplified spike in control not associated with the reaction composition, and wherein excluding the contaminated library fragment products improves the library sequencing quality.

6. The method of claim 5, wherein the library comprises at least one of a DNA library, an RNA library, or combinations thereof.

7. The method of claim 5, wherein the reaction composition comprises at least two different spike in controls and at least two different nucleic acid adapters.

8. The method of claim 5, wherein a concentration of the at least one spike in control in the reaction composition is between 0.1% to 2.0% (weight/weight %) of the plurality of sample nucleic acids in the reaction composition.

9. The method of claim 5, wherein the nucleic acid adapter comprises at least one of a primer binding site and a barcode.

10. The method of claim 5, wherein the nucleic acid adapter comprises both a primer binding site and a barcode.

11. The method of claim 10, further comprising determining the sample has been contaminated based on the presence of an amplified barcode not associated with the reaction composition.

* * * * *